US011319538B2

(12) United States Patent
Dallas et al.

(10) Patent No.: US 11,319,538 B2
(45) Date of Patent: *May 3, 2022

(54) METHODS AND COMPOSITIONS OF SHORT SMALL HAIRPIN RNAS AND MICRORNAS FOR WOUND HEALING

(71) Applicant: SOMAGENICS, INC., Santa Cruz, CA (US)

(72) Inventors: Anne Dallas, Santa Cruz, CA (US); Heini Ilves, Santa Cruz, CA (US); Sumedha Jayasena, Santa Cruz, CA (US); Brian H. Johnston, Santa Cruz, CA (US)

(73) Assignee: SOMAGENICS, INC., Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,118

(22) Filed: Sep. 5, 2019

(65) Prior Publication Data

US 2019/0390202 A1 Dec. 26, 2019

Related U.S. Application Data

(63) Continuation of application No. 15/752,182, filed as application No. PCT/US2016/046884 on Aug. 12, 2016, now Pat. No. 10,450,569.

(60) Provisional application No. 62/204,957, filed on Aug. 13, 2015.

(51) Int. Cl.
*C12N 15/113* (2010.01)
*A61K 31/713* (2006.01)
*C07H 21/02* (2006.01)
*A61K 45/06* (2006.01)
*A61P 17/02* (2006.01)

(52) U.S. Cl.
CPC ........ *C12N 15/1137* (2013.01); *A61K 31/713* (2013.01); *A61K 45/06* (2013.01); *A61P 17/02* (2018.01); *C07H 21/02* (2013.01); *C12N 15/1131* (2013.01); *C12N 2310/317* (2013.01); *C12N 2310/3231* (2013.01); *C12Y 114/11002* (2013.01)

(58) Field of Classification Search
None
See application file for complete search history.

(56) References Cited

U.S. PATENT DOCUMENTS

| | | | |
|---|---|---|---|
| 9,463,244 B2 | 10/2016 | Castleberry et al. | |
| 10,450,569 B2 | 10/2019 | Dallas et al. | |
| 2013/0143952 A1* | 6/2013 | Becker | A61P 9/00 514/44 R |
| 2013/0165500 A1 | 6/2013 | Ason et al. | |
| 2014/0304200 A1 | 10/2014 | Wall | |
| 2014/0336370 A1 | 11/2014 | Esau et al. | |
| 2014/0350086 A1 | 11/2014 | Brown et al. | |

FOREIGN PATENT DOCUMENTS

| | | |
|---|---|---|
| CN | 102164905 A | 8/2011 |
| CN | 104024227 A | 9/2014 |
| CN | 105209618 A | 12/2015 |
| CN | 105457039 A | 4/2016 |
| EP | 2281887 A1 | 2/2011 |

OTHER PUBLICATIONS

Ge et al. RNA 2010, vol. 16, pp. 106-117.*
Biswas, S. et al. Hypoxia inducible microRNA 210 attenuates keratinocyte proliferation and impairs closure in a murine model of ischemic wounds. PNAS 107(15); 6976-6981 (Aug. 13, 2010).
Cheloufi, S. et al. A Dicer-independent miRNA biogenesis pathway that requires Ago catalysis. Nature, vol. 465; pp. 584-590 (Jun. 3, 2010).
Chinese Patent Application No. 201680059575 Office Action dated Nov. 14, 2019.
Cifuentes, D. et al. A novel miRNA processing pathway independent of dicer requires argonaute2 catalytic activity. Science, vol. 328; 1694-1698 (Jun. 25, 2010).
Figure 1. Wound Healing-Background Text.
Genbank. Homo sapiens egl-9 family hypoxia inducible factor 1 (EGLN1), mRNA. NCBI Reference Sequence: NM_022051.2. 8 pages.
Genbank. Mus musculus egl-9 family hypoxia-inducible factor 1 (Egln1), transcript variant 1, mRNA. NCBI Reference Sequence: NM_053207.2. 6 pages.
International Application No. PCT/US2016/046884 International Preliminary Report on Patentability dated Feb. 22, 2018.
International Application No. PCT/US2016/046884 International Search Report and Written Opinion dated Dec. 30, 2016 .
Lennox, K., et al. Improved performance of anti-miRNA oligonucleotides using a novel non-nucleotide modifier, Molecular Therapy-Nucleic Acids, 2; pp. 1-19 (2013).
Rios et al. GNAS1 and PHD2 short-interfering RNA support bone regeneation in vitro and in an in vivo sheep model. Clinical Orthopaedics and Related Research, 470(9):2541-2553 (Jul. 26, 2012) .

(Continued)

*Primary Examiner* — Tracy Vivlemore
(74) *Attorney, Agent, or Firm* — Wilson Sonsini Goodrich & Rosati

(57) ABSTRACT

Wound healing is a complex homeostatic process in which several distinct types coordinate to repair a physical damage. Failure to close wounds contributes to the pathology of conditions like diabetes mellitus, particularly in the elderly. Presented herein are molecules, pharmaceutical compositions, and methods for applying small RNA oligonucleotide technology to wound healing. Small RNA oligonucleotide approaches as disclosed herein provide a therapeutic strategy for improving both basal and pathological wound healing.

20 Claims, 29 Drawing Sheets

Specification includes a Sequence Listing.

(56) References Cited

OTHER PUBLICATIONS

Thoms, et al. Inhibition of Hypoxia-inducible Factor-targeting Prolyl Hydroxylase Domain-containing Protein 2 (PHD2) Enhaces Matrix Synthesis by Human Chondrocytes. The Journal of Biological Chemistry, 285:20472-20480 (Apr. 19, 2010).
Yang, S. et al. Conserved vertebrate mir-451 provides a platform for Dicer-independent, Ago2-mediated mircoRNA biogenesis. PNAS 107(34); 15163-15168 (Aug. 24, 2010).
Castleberry et al., Nanolayered siRNA Dressing for Sustained Localized Knockdown. ACS Nano 7(6): 5251-5261 (2013).
Dallas et al., Acceleration of Diabetic Wound Healing with PHD2- and miR-210-Targeting Oligonucleotides. Tissue Engineering: Part A. 21 pages (2018).
Ivan, miR-210: Fine-Tuning the Hypoxic Response. Adv Exp Med Biol 772: 205-227 (2014).

\* cited by examiner

SG303 = SEQ ID NO. 9 and 10
SG302 = SEQ ID NO. 7

SG404 = SEQ ID NO. 30

SG404 = SEQ ID NO. 30

SG404 = SEQ ID NO. 30

SG302 = SEQ ID NO. 7

SEQ ID NO. 44

SEQ ID NO. 45

SEQ ID NO. 46

SEQ ID NO. 47

SEQ ID NO. 48

SEQUENCE LISTING

```
<160> NUMBER OF SEQ ID NOS: 329

<210> SEQ ID NO 1
<211> LENGTH: 7102
<212> TYPE: DNA
<213> ORGANISM: Homo sapiens

<400> SEQUENCE: 1 ttagggggcag aaaaacattt gtaataatta atggctttga gagacacaag gctttgtttg    60
ccccagagta ttagttaacc cacctagtgc tcctaatcat acaatattaa ggattgggag   120
ggacattcat tgcctcactc tctatttgtt tcaccttctg taaaattggt agaataatag   180
tacccacttc atagcattgt atgatgatta aattggttaa tattttaaa atgcttagaa    240 cacagattgg gcacataaca gcaagcacca catgtgttta taagataaat tcctttgtgt   300
tgccttccgt taaagtttaa ataagtaaat aaataaataa atacttgcat gacattttga   360
agtctctcta taacatctga gtaagtggcg gctgcgacaa tgctactgga gttccagaat   420
cgtgttggtg acaagattgt tcaccagcat atggtgtggt gaaaactcac taatttggaa   480
ttagttcaga ttattaagcc tgaataggtg aaaatcctga aatcaaggat ctttggaact   540
atttgaaatc agtattttat attttcctgt tgtattcatt aaagtgttgc aagtgttcta   600
tttgatggat taagtatatt taggatatac atgttcaatt tgtgattttg tatacttaat   660
tggaacaaga aagctaataa aggttttgat atggacatct attcttttaa gtaaacttca   720
atgaaaatat atgagtagag catatagaga tgtaaataat ttgtggacac accacagact   780
gaaatagcaa atttaaaaga aattgttgga agaatcaagt gtttgtggaa tgagtcctcc   840
tagtaaagtt cctgctcttg tgaataatta agcctcatgt ataattacta tagcaaaagg   900
aagcctaaga agtattagac tctacttgta tttaaattac atttacata atttatgtgt    960 atgaaaaatg ttttaaatgc ttatttcgt aagccatgag atagctcctt tatattttaa   1020
gaatttctga attaatttgc ttggatttta ttagtgcaaa tggcagagct agcaattcct  1080
```

```
ttttctgtgt tcccattcca tcctattcat ccctctttta ggaaactctg aactctggat    1140
tgtccttgtt tacatacctg cctcctgcat tggactatgt gtctctgagt gtagtatgac    1200
taattcattt gtttgtcaag gactctcaat gcatttgttg aacagcctaa ttagtaatgt    1260
ctgcaacaat gacattttac tgtatttaat aaagctctgg gaaagtagga tacacataag    1320
acaggtctag gtctaaattc tttacagaaa cttggatttt tagttcggtt tgaaatttga    1380
agatgtgagt atatttatct cagtttccca aaggacaagc taattggaat tatcatcctc    1440
tttcacttga ttggatcccc agaatgccat ttacgcatgc agcaggattt tataacagtt    1500
ttaaattctg tatatttgat gaagaggttt tatattttg gattcaagcc tcttttaaa     1560 cttctacaat atggtttaca ataattcctt atatcctgct tttgaaatac atattacaac    1620
tttttaagtt tggaaggcta tatttcaagg actgaagtta cagtatactc aagtgataca    1680
caagcctagc accccacttt ccacatagtg ttcgataaag attgataaac tcgaaatcac    1740
agacctttta attcttaaga caaatagcag cagaaagaaa catctttggc ttatttctgg    1800
taaggttttt atgctctgta aaacaaagaa ttgtattcat ccgcgcagca cagattctat    1860
taaaaataaa tgtgagagtc gttaatgtag tactgctcat ttaccatcaa aattcacttt    1920
tcaggaataa tcccatcagt ttaaattgga tattggaatg agcattgatt acatttaact    1980
tggtagccca aaatttcttc atggggtttt gaactcggcg ggatttcaaa ggttttaaaa    2040
atgagttttt gatttttttt aaaaccctca aatttcatta cctttaaact aggtcgaaac    2100
ggggcgcaag agattggatt aacaccatag taatacttat tttgttctta accatttcag    2160
ggcttcttga aatagaggct gtatggtgta atggaaaaaa cagccttgga atctgggagc    2220
ctgattcctg gattcagtcc cagttttgcg tgaccttggg caagttactt tacttctctg    2280
aatttccgtt tcctcctctg caaaatgagg atcgcaatag ccaccttgca accttgactg    2340
gagcgagcct cgcacacccc gcgccggcct ggaggaagag cagccatgat tacgccgcct    2400
tcgctccgct acccgcttgc ggctggcgcc ctcctccagc aggtgtaggc gctgccgcgc    2460
tgccccacgc ctttccgccg ctcgcgggcc tgcgcctcgg cgtccccgag gaggccgctg    2520
cgggctgagg tagcgcaccg gcctctcggc gtcccagtcc ggtcccgggc ggagggaaag    2580
cgggcgaccc acctccgagg cagaagccga ggcccggccc cgccgagtgc ggaggagcgc    2640
aggcagcccc cgcccctcgg ccctcccccc ggccctcccg gccctccctc cgccccctcc    2700
gccctcgcgc gccgcccgcc cgggtcgccg cggggccgtg gtgtacgtgc agagcgcgca    2760
gagcgagtgg cgcccgtatg ccctgcgctc ctccacagcc tgggccgggc cgcccgggac    2820
gctgaggcgg cggcggcggc cgaggggggcc ggtcttgcgc tccccaggcc cgcgcgcctg    2880
agcccaggtt gccattcgcc gcacaggccc tattctctca gccctcggcg gcgatgaggc    2940
gctgaggcgg ctgccggcgc tgcgccggag cttaggactc ggaagcggcc gggccgaggg    3000 cgtgggggtgc cggcctccct gaggcgaggg tagcgggtgc atggcgcagt aacggcccct    3060
atctctctcc ccgctcccca gcctcgggcg aggccgtccg gccgctaccc ctcctgctcg    3120
gccgccgcag tcgccgtcgc cgccgccgcc gccgccatgg ccaatgacag cggcgggccc    3180
ggcgggccga gccgagcga gcgagaccgg cagtactgcg agctgtgcgg gaagatggag    3240
aacctgctgc gctgcagccg ctgccgcagc tccttctact gctgcaagga gcaccagcgt    3300
caggactgga gaaagcacaa gctcgtgtgc caggggcagcg agggcgccct cggccacgga    3360
gtgggcccac accagcattc cggccccgcg ccgccggctg cagtgccgcc gcccagggcc    3420
ggggcccggg agcccaggaa ggcagcggcg cgccgggaca acgcctccgg ggacgcggcc    3480
```

```
aagggaaaag taaaggccaa gcccccggcc gacccagcgg cggccgcgtc gccgtgtcgt    3540
gcggccgccg gcggccaggg ctcggcggtg gctgccgaag ccgagcccgg caaggaggag    3600
ccgccggccc gctcatcgct gttccaggag aaggcgaacc tgtacccccc aagcaacacg    3660 cccgggatg cgctgagccc cggcggcggc ctgcggccca acgggcagac gaagcccctg    3720
ccggcgctga agctggcgct cgagtacatc gtgccgtgca tgaacaagca cggcatctgt    3780
gtggtggacg acttcctcgg caaggagacc ggacagcaga tcggcgacga ggtgcgcgcc    3840
ctgcacgaca ccgggaagtt cacggacggg cagctggtca gccagaagag tgactcgtcc    3900
aaggacatcc gagcgataa gatcacctgg atcgagggca aggagcccgg ctgcgaaacc    3960
attgggctgc tcatgagcag catggacgac ctgatacgcc actgtaacgg gaagctgggc    4020
agctacaaaa tcaatggccg gacgaaagcc atggttgctt gttatccggg caatggaacg    4080
ggttatgtac gtcatgttga taatccaaat ggagatggaa gatgtgtgac atgtatatat    4140
tatcttaata aagactggga tgccaaggta agtggaggta acttcgaat ttttccagaa    4200 ggcaaagccc agtttgctga cattgaaccc aaatttgata gactgctgtt tttctggtct    4260
gaccgtcgca accctcatga agtacaacca gcatatgcta caaggtacgc aataactgtt    4320
tggtattttg atgcagatga gagagcacga gctaaagtaa aatatctaac aggtgaaaaa    4380
ggtgtgaggg ttgaactcaa taaaccttca gattcggtcg gtaaagacgt cttctagagc    4440
ctttgatcca gcaatacccc acttcaccta caatattgtt aactatttgt taacttgtga    4500
atacgaataa atgggataaa gaaaaataga caaccagttc gcattttaat aaggaaacag    4560
aaacaacttt ttgtgttgca tcaaacagaa gattttgact gctgtgactt tgtactgcat    4620
gatcaacttc aaatctgtga ttgcttacag gaggaagata agctactaat tgaaaatggt    4680
ttttacatct ggatatgaaa taagtgccct gtgtagaatt ttttcattc ttatattttg    4740 ccagatctgt tatctagctg agttcatttc atctctccct tttttatatc aagtttgaat    4800
ttgggataat ttttctatat taggtacaat ttatctaaac tgaattgaga aaaaattaca    4860
gtattattcc tcaaaataac atcaatctat ttttgtaaac ctgttcatac tattaaattt    4920
tgccctaaaa gacctcttaa taatgattgt tgccagtgac tgatgattaa ttttattta    4980 cttaaaataa gaaaggagc actttaatta caactgaaaa atcagattgt tttgtagtcc    5040
ttccttacac taatttgaac tgttaaagat tgctgctttt ttttgacat tgtcaataac    5100 gaaacctaat tgtaaaacag tcaccattta ctaccaataa cttttagtta atgttttaca    5160
aggaaaaaga cacaagaaga gtttaaattt ttttgttttg ttttgttttt ttgagacagt    5220
cttgctctgt tacccaggct ggaggggagt ggtgcattct tggctcactg caacctccgc    5280
ctcccaggtt caagcaatcc tcccacctca gcctcccaac tagctgggac tgcaggcaca    5340
caccaccatg cctgactaat ttttgtatgt ttagtagaga cggggttttg ccatgttgcc    5400
taggctgggg tttaagttaa atttttttaaa aactaaagt gactggcact aagtgaactt    5460
gagattatcc tcagcttcaa gttcctaaga taagggcttt cttaagcttt caggtgtatg    5520
tatcctctag atgtagacaa taatgtccca tttctaagtc ttttcctttt gcttctcctt    5580
aaattgattg tacttccaaa tttgctgtta tgttttttc ctaatactgt gatctatctg    5640
atctgcagac aagaaccttg tctctgttga agagcatcaa ggggagatta tgtacacatt    5700
gaaactgaag tgtggtgtta ctgacggaat gtgcagtaac tcctcagata tctgttaagg    5760
catttcccag atgtgatgcc agccttctta cctgtactga aagatgctta gcttagaaaa    5820
```

```
aaacaaaaca gatgcaaaat cagataattt tattttgttt catgggttttt cttatttact    5880 ttttaaacaa ggaaggaata ttagaaaatc acacaaggcc tcacatacat gttatttaaa    5940
gaatgaattg ggacggatgt cttagacttc actttcctag gcttttttagc aaaacctaaa    6000 gggtggtatc catattttgc gtgaattatg ggtgtaagac cttgcccact taggttttct    6060
atctctgtcc ttgatcttct tgccaaaat gtgagtatac agaaattttc tgtatatttc    6120
aacttaagac attttttagca tctgtatagt ttgtattcaa tttgagacct tttctatggg    6180
aagctcagta attttttatta aaagattgcc attgctattc atgtaaaaca tggaaaaaaa    6240
ttgtgtagtg aagccaacag tggacttagg atgggattga atgttcagta tagtgatctc    6300
acttaggaga atttgcagga gaaagtgata gtttattgtt ttttcctcgc ccatattcag    6360
ttttgttcta cttcctcccc ttccttccag atgataacat cacatctcta cagtaagtgc    6420
ctctgccagc ccaacccagg agcgcaagtt gtctttgcca tctggtctat agtacagtgc    6480
gcggcgttag ccacaactc aaaagcatta tcttttttag ggttagtaga aattgtttta    6540
tgttgatggg aggtttgttt gattgtcaaa atgtacagcc acagcctttt aatttgggag    6600
cccctgttgt cattcaaatg tgtacctcta cagttgtaaa aagtattaga ttctactatc    6660
tgtgggttgt gcttgccaga caggtcttaa attgtatatt ttttggaaaa gtttatatac    6720
tctcttagga atcattgtga aaagatcaag aaatcaggat ggccatttat ttaatatcca    6780
ttcatttcat gttagtggga ctattaactt gtcaccaagc aggactctat ttcaaacaaa    6840
atttaaaact gtttgtggcc tatatgtgtt taatcctggt taaagataaa gcttcataat    6900
gctgttttta ttcaacacat taaccagctg taaaacacag acctttatca agagtaggca    6960
aagattttca ggattcatat acagatagac tataaagtca tgtaatttga aaagcagtgt    7020
ttcattatga aagagctctc aagttgcttg taaagctaat ctaattaaaa agatgtataa    7080
atgttgttga aacattaaaa aa                                              7102

<210> SEQ ID NO 2
<211> LENGTH: 3524
<212> TYPE: DNA
<213> ORGANISM: Mus sp.

<400> SEQUENCE: 2
ggctgggccc gcccgcccag ggcgctgtgc gccgcgcagg ccgcgctctc tccggcgcga      60
tgcggcgcta ggcggccccg ggcaaggcag gcgaggccag ggcgcgcgcg gcctcccgca     120
gcgggcggcg gccccgggcg ggcgccccga cggccccgcc gccgcccgc tcccggcccg     180 cggcccgccc tgccgcggcc atggccagtg acagcggcgg gccggcgtg ctgagcgcca     240 gcgagcgcga ccggcagtac tgcgagctgt gcgggaagat ggagaacctg ctgcgctgcg     300
gccgctgccg cagctccttc tactgctgca agagcaccac gcgccaggac tggaagaagc     360
acaagctggt gtgccaggc ggcgaggccc ccgcgcgca gccgcgccg gcgcagcccc     420 gcgtcgcgcc cccgcccggt ggggcccccg gagccgcgcg cgccggcggg gcggcccggc     480
gcggggacag cgcggcggcc tcgcgcgtac cgggcccgga ggacgcggcg caggcccgga     540
gcggccccgg cccagcagag cccggctccg aggatcctcc gcttagccgg tctccgggcc     600
ccgagcgcgc cagcctgtgc ccagcgggtg gcggccccgg ggaggcgctg agtcccggtg     660
gagggctgcg gcccaacggg cagaccaagc cgttgcccgc gttgaagctg gctctggagt     720
acatcgtgcc gtgcatgaac aagcacggca tctgcgtggt ggacgacttc ctgggcagg     780 agaccgggca gcagatcggc gatgaggtgc gcgccctgca cgacaccggc aagttcacgg     840
```

```
acgggcagct ggtcagccag aagagtgact cttccaagga catccggggg gaccagatca    900
cctggatcga gggcaaagag cccggctgcg aaaccatcgg cctgctcatg agcagcatgg    960
acgacctgat ccgccactgc agcgggaagc tgggcaacta caggataaac ggccgaacga   1020
aagccatggt tgcttgttac ccaggcaacg gaacaggcta tgtccgtcac gttgataacc   1080
caaatggaga tggaagatgc gtgacatgta tatattatct aaataaagac tgggacgcca   1140
aggtaagtgg aggtattctt cgaattttc cagaaggcaa agcccagttt gctgacattg   1200
aacccaaatt tgatagactg ctgttttct ggtctgaccg gcgtaaccct catgaagtac   1260
agccagcata cgccacaagg tacgcaataa ctgtttggta ttttgatgca gatgagcgag   1320
cgagagctaa agtaaaatat ctaacaggtg agaaggtgt gagggttgaa ctcaagccca   1380
attcagtcag caaagacgtc tagtggggcc ttgggtccgg cagtacccac gtcacctaca   1440
gcctctcagt tgccttctgt ggactcgtgg acaggatgga cagagagaca cctgcctggt   1500
atttcagctg ggagccaggc gacttcgccg ggtgtcatcc aacagagggc tccatctgct   1560
gggactgtac tgtggggtca gctccagatc tgtgactgct cttggctgct gacccaagag   1620
gagacgctgt cggaggagag tagcttttcc atctggacac gaaacaaggg cccttttgtag   1680 gaatttcttc agtcttctat tttgccagac ctgtcaccta actgagttca tttcatctct   1740
tttttatatc aagttttgaa ttcggggaat ttttgtatta ggtacaattt atcaaaactg   1800
aattaagaaa aaaaaattta cagtattatt ctcaaaataa catcaatcta tttttgtaaa   1860
cctcttcatg ctattaaatt ttgccctcaa ggcctcctgc gatgattgtt gccagtgagt   1920
gacgacgtgt tgcttctgcc tgaacgtaaa ggacgggcgg gcgctgtgtc ccagcccgag   1980
tgcacgaggt ttttcttggc ccgtctctca gtgattccaa cctgtaaagg tcactgctct   2040
cgcgcttcga ccgacctaac agtagatggt tgccactggc actcaactaa ctcaacatag   2100
ttacaagagg aaacaagcca caggagaggg tttgtctctt cagttaattt ttttaaagcg   2160
aagtgacggg cactaaatga actcggggct ctccctcagc ttcgggttcc tgagacaaag   2220
ggctttcttc tgcggcaggt ctagcctgcc tacagccgtg tcccactgcc gcaggtttcc   2280
ttgtggcttc tccgtagttt tgactgtgct tccagaccct tccaggtcag ggctgtgttc   2340
ttgtggcagg gcacctggtg gacccaggca cgtgaatgtg gtatgtggtt gtagcctcaa   2400
tcgtggccat cggctccttg gacagccacg agccattttc atacccaata atgaaagctg   2460
tgtgctagct tagaaatcaa agggggtgta aaagcacaca ttctttgttt tatgggtttt   2520 tctctttta gaggacagag ggacaaccac acgaggctgc cagactcctg tcacctctac   2580 agtccccta gaaagccaga gtttgcacag attgtgggta taactcctgt ccccttaggt   2640
gttctatctc cgaccttgat ctttgccaaa atgtgtgtat gcagaactat ttctgtgtat   2700
tttccttgac acccgtctta gcacctgtgt agtttgtatc cggttagaaa ccttttctat   2760
ggaaagctca gtaattctta ttaagagatt gctattgttc atgtaaaaca tgaaaacaac   2820
caagtagagc cgtgtgtgga tgagggccca ctcagcactg tgcttgcttg aggggctctc   2880
ggcaggaagt ctccttctga cccatatccg ctgaccacac ctctccagca agtgcctctg   2940
ccgctggcca gctcaaggtt tgcccacctg gccccgaagc accgtgtttc ggagttggga   3000
ggaactgttt ggcattgttg gcagaaggtg tgattgcctg gagcagcagc ctttaaaatt   3060
ctggagaccc tgtagtcctt tgtatctcag acctttactg atgtaccagg tcccagattc   3120
tgtggcaggg gatggggtgg ggtgtgcttg ccagacgaaa tttaaattat ctatcttttg   3180
```

```
ggaagtgtgt gctttcctgg aggtcactgt gaaaacaaac aaacaaatca ggaccgttaa    3240
ccccttaatg cccacttaaa ctcaatttca tgttaggact cttgtttaaa accatttgtg    3300
gcctgtatgt gttcatcctg gttagagaga aagctttatg acgctgtttc tgttcaacac    3360
attaaccagc tgtggaacag ccctttttgc acgacaggca gggcacttca ggattcgcag    3420
agagactcgt gtggtttgga agtggtattt cctatgaaag cctctcacgt tgcttgtaaa    3480
gctaatctaa ttaaaaagat gtataaatgt tcttgaaaaa aatc                    3524
```

<210> SEQ ID NO 3
<211> LENGTH: 22
<212> TYPE: RNA
<213> ORGANISM: Unknown
<220> FEATURE:
<223> OTHER INFORMATION: Description of Unknown:
      miR-210 oligonucleotide

<400> SEQUENCE: 3
cugugcgugu gacagcggcu ga                                              22

<210> SEQ ID NO 4
<211> LENGTH: 22
<212> TYPE: RNA
<213> ORGANISM: Unknown
<220> FEATURE:
<223> OTHER INFORMATION: Description of Unknown:
      miR-21 oligonucleotide

<400> SEQUENCE: 4
uagcuuauca gacugauguu ga                                              22

<210> SEQ ID NO 5
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cuuccuuuug cuauaguaau uuuacuauag caaaaggaag uu                        42

<210> SEQ ID NO 6
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uguugcagac auuacuaauu uauuaguaau gucugcaaca uu                        42

<210> SEQ ID NO 7
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uauaccucca cuuaccuugu ucaagguaag uggagguaua uu                        42

<210> SEQ ID NO 8

```
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uauaccucca cuuaccuugu caagguaag uggagguaua uu                             42

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uauaccucca cuuaccuugu u                                                   21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
caagguaagu ggagguauau u                                                   21

<210> SEQ ID NO 11
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
auucgaagua uaccuccacu uguggaggua uacuucgaau uu                            42

<210> SEQ ID NO 12
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cgaaguauac cuccacuuau uuaaguggag guauacuucg uu                            42

<210> SEQ ID NO 13
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aguauaccuc cacuuaccuu uagguaagug gagguauacu uu                            42

<210> SEQ ID NO 14
<211> LENGTH: 42
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uaccuccacu uaccuuggcu ugccaaggua aguggaggua uu                       42

<210> SEQ ID NO 15
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cuccacuuac cuuggcaucu ugaugccaag guaaguggag uu                       42

<210> SEQ ID NO 16
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cacuuaccuu ggcaucccau uugggaugcc aagguaagug uu                       42

<210> SEQ ID NO 17
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
agguucucca ucuucccgcu ugcgggaaga uggagaaccu uu                       42

<210> SEQ ID NO 18
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
augccgugcu uguucaugcu ugcaugaaca agcacggcau uu                       42

<210> SEQ ID NO 19
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ucacucuucu ggcugaccau uuggucagcc agaagaguga uu                       42

<210> SEQ ID NO 20
<211> LENGTH: 42
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 20
aucuuccauc uccauuuggu uccaaaugga gauggaagau uu                          42

<210> SEQ ID NO 21
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugugcuucuu ccaguccugu ucaggacugg aagaagcaca uu                          42

<210> SEQ ID NO 22
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aucaggucgu ccaugcugcu ugcagcaugg acgaccugau uu                          42

<210> SEQ ID NO 23
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auaccuccac uuaccuuggu uccaagguaa guggagguau uu                          42

<210> SEQ ID NO 24
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uggcguaugc uggcuguacu uguacagcca gcauacgcca uu                          42

<210> SEQ ID NO 25
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cucacaccuu ucucaccugu ucaggugaga aaggugugag uu                          42

<210> SEQ ID NO 26
<211> LENGTH: 42
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 26
cugaauuggg cuugaguucu ugaacucaag cccaauucag uu                          42

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
cugaauuggg cuugaguucu ugaacucaag cccaauucag tt                          42

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gaacucaagc ccaauucagu u                                                 21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cugaauuggg cuugaguucu u                                                 21

<210> SEQ ID NO 30
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cugaauuggg cuugaguucu ugaacucaag cccaauucag                             40

<210> SEQ ID NO 31
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cugaauuggg cuugaguucu gaacucaagc ccaauucag                              39

<210> SEQ ID NO 32
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucagccgcug ucacacgcac ag                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcagccgctg tcacacgcac ag                                              22

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ucagccgcug ucacacgcac ag                                              22

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gccgctgtca cacgcaca                                                   18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agagctccct tcaatccaaa                                                 20

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ucagccgcug ucacacgcac ag                                              22

<210> SEQ ID NO 38
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 38
ucagccgcug ucacacgcac ag                                              22

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucagccgcug ucacacgcac ag                                              22

<210> SEQ ID NO 40
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ucagccgcug ucacacgcac ag                                              22

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ucagccgcug ucacacgcac ag                                              22

<210> SEQ ID NO 42
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ucagccgcug ucacacgcac ag                                              22

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ucagccgcug ucacacgcac ag                                              22

<210> SEQ ID NO 44
<211> LENGTH: 59
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 44
uagcuuauca gacugauguu gacuguugaa ucucauggca acaccagucg augggcuuu     59

<210> SEQ ID NO 45
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uagcuuauca gacugauguu gacaucaguc ugauaagcuc                         40

<210> SEQ ID NO 46
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uagcuuauca gacugauguu gacaucaguc ugauaagcua uu                      42

<210> SEQ ID NO 47
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uagcuuauca gacugauguu gauuucaaca ucagucugau aagcuauu                48

<210> SEQ ID NO 48
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uagcuuauca gacugauguu gauuucaaca ucagucugau aagcuauu                48

<210> SEQ ID NO 49
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ccgggcccgc cgcugucauu uaugacagcg gcgggcccgg uu                      42

<210> SEQ ID NO 50
<211> LENGTH: 42
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 50
gccgggcccg ccgcugucau uugacagcgg cgggcccggc uu                            42

<210> SEQ ID NO 51
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cgccgggccc gccgcugucu ugacagcggc gggcccggcg uu                            42

<210> SEQ ID NO 52
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ccgccgggcc cgccgcuguu uacagcggcg ggcccggcgg uu                            42

<210> SEQ ID NO 53
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cucgcaguac ugccggucuu uagaccggca guacugcgag uu                            42

<210> SEQ ID NO 54
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gcucgcagua cugccggucu ugaccggcag uacugcgagc uu                            42

<210> SEQ ID NO 55
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
agcucgcagu acugccgguu uaccggcagu acugcgagcu uu                            42

<210> SEQ ID NO 56
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
cagcucgcag uacugccggu uccggcagua cugcgagcug uu                42

<210> SEQ ID NO 57
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
acagcucgca guacugccgu ucggcaguac ugcgagcugu uu                42

<210> SEQ ID NO 58
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
cacagcucgc aguacugccu uggcaguacu gcgagcugug uu                42

<210> SEQ ID NO 59
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
gcacagcucg caguacugcu ugcaguacug cgagcugugc uu                42

<210> SEQ ID NO 60
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cgcacagcuc gcaguacugu ucaguacugc gagcugugcg uu                42

<210> SEQ ID NO 61
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ccgcacagcu cgcaguacuu uaguacugcg agcugugcgg uu                42

<210> SEQ ID NO 62
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 62
cccgcacagc ucgcaguacu uguacugcga gcugugcggg uu                         42

<210> SEQ ID NO 63
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ucccgcacag cucgcaguau uuacugcgag cugugcggga uu                         42

<210> SEQ ID NO 64
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uucccgcaca gcucgcaguu uacugcgagc ugugcgggaa uu                         42

<210> SEQ ID NO 65
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cuucccgcac agcucgcagu ucugcgagcu gugcgggaag uu                         42

<210> SEQ ID NO 66
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ucuucccgca cagcucgcau uugcgagcug ugcgggaaga uu                         42

<210> SEQ ID NO 67
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aucuucccgc acagcucgcu ugcgagcugu gcgggaagau uu                         42

<210> SEQ ID NO 68
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 68
caucuucccg cacagcucgu ucgagcugug cgggaagaug uu                           42

<210> SEQ ID NO 69
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ccaucuuccc gcacagcucu ugagcugugc gggaagaugg uu                           42

<210> SEQ ID NO 70
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonuceotide

<400> SEQUENCE: 70
uccaucuucc cgcacagcuu uagcugugcg gaagaugga uu                            42

<210> SEQ ID NO 71
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cuccaucuuc ccgcacagcu ugcugugcgg gaagauggag uu                           42

<210> SEQ ID NO 72
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ucuccaucuu cccgcacagu ucugugcggg aagauggaga uu                           42

<210> SEQ ID NO 73
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uucuccaucu ucccgcacau uugugcggga agauggagaa uu                           42

<210> SEQ ID NO 74
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
```
guucuccauc uucccgcacu ugugcgggaa gauggagaac uu    42

<210> SEQ ID NO 75
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gguucuccau cuucccgcau uugcgggaag auggagaacc uu    42

<210> SEQ ID NO 76
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
agguucucca ucuucccgcu ugcgggaaga uggagaaccu uu    42

<210> SEQ ID NO 77
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
cagguucucc aucuucccgu ucgggaagau ggagaaccug uu    42

<210> SEQ ID NO 78
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gcagguucuc caucuucccu ugggaagaug gagaaccugc uu    42

<210> SEQ ID NO 79
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
agcagguucu ccaucuuccu uggaagaugg agaaccugcu uu    42

<210> SEQ ID NO 80
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cagcagguuc uccaucuucu ugaagaugga gaaccugcug uu                              42

<210> SEQ ID NO 81
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gcagcagguu cuccaucuuu aagauggag aaccugcugc uu                              42

<210> SEQ ID NO 82
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cgcagcaggu ucccaucuu uagauggaga accugcugcg uu                              42

<210> SEQ ID NO 83
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
gcgcagcagg uucuccaucu ugauggagaa ccugcugcgc uu                             42

<210> SEQ ID NO 84
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
agcgcagcag guucuccauu uauggagaac cugcugcgcu uu                             42

<210> SEQ ID NO 85
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
cagcgcagca gguucuccau uuggagaacc ugcugcgcug uu                             42

<210> SEQ ID NO 86
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gcagcgcagc agguucuccu uggagaaccu gcugcgcugc uu                             42

<210> SEQ ID NO 87
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ugcagcgcag cagguucucu ugagaaccug cugcgcugca uu                    42

<210> SEQ ID NO 88
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
aggagcugcg gcagcggcuu uagccgcugc cgcagcuccu uu                    42

<210> SEQ ID NO 89
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
aaggagcugc ggcagcggcu ugccgcugcc gcagcuccuu uu                    42

<210> SEQ ID NO 90
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
gaaggagcug cggcagcggu uccgcugccg cagcuccuuc uu                    42

<210> SEQ ID NO 91
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
agaaggagcu gcggcagcgu ucgcugccgc agcuccuucu uu                    42

<210> SEQ ID NO 92
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uagaaggagc ugcggcagcu ugcugccgca gccuucucua uu                    42

<210> SEQ ID NO 93
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 93
guagaaggag cugcggcagu ucugccgcag cuccuucuac uu          42

<210> SEQ ID NO 94
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 94
aguagaagga gcugcggcau ugccgcagc uccuucuacu uu          42

<210> SEQ ID NO 95
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 95
caguagaagg agcugcggcu ugccgcagcu ccuucuacug uu          42

<210> SEQ ID NO 96
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 96
gcaguagaag gagcugcggu uccgcagcuc cuucuacugc uu          42

<210> SEQ ID NO 97
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 97
agcaguagaa ggagcugcgu ucgcagcucc uucuacugcu uu          42

<210> SEQ ID NO 98
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
cagcaguaga aggagcugcu ugcagcuccu ucuacugcug uu          42

```
<210> SEQ ID NO 99
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gcagcaguag aaggagcugu ucagcuccuu cuacugcugc uu                    42

<210> SEQ ID NO 100
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ugcagcagua gaaggagcuu uagcuccuuc uacugcugca uu                    42

<210> SEQ ID NO 101
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uugcagcagu agaaggagcu ugcuccuucu acugcugcaa uu                    42

<210> SEQ ID NO 102
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
cuugcagcag uagaaggagu ucccuucua cugcugcaag uu                     42

<210> SEQ ID NO 103
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gugcuucuuc caguccugau uucaggacug gaagaagcac uu                    42

<210> SEQ ID NO 104
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ugugcuucuu ccaguccugu ucaggacugg aagaagcaca uu                    42

<210> SEQ ID NO 105
```

<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uugugcuucu uccaguccuu uaggacugga agaagcacaa uu                              42

<210> SEQ ID NO 106
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
cuugugcuuc uuccagnccu uggacuggaa gaagcacaag uu                              42

<210> SEQ ID NO 107
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gcuugugcuu cuccagucu ugacuggaag aagcacaagc uu                               42

<210> SEQ ID NO 108
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
agcuugugcu ucuuccaguu uacuggaaga agcacaagcu uu                              42

<210> SEQ ID NO 109
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gagcuugugc uucuuccagu ucuggaagaa gcacaagcuc uu                              42

<210> SEQ ID NO 110
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cugcccguug ggccgcaggu uccugcggcc caacgggcag uu                              42

<210> SEQ ID NO 111
<211> LENGTH: 42

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ucugcccguu gggccgcagu ucugcggccc aacgggcaga uu                            42

<210> SEQ ID NO 112
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gucugcccgu ugggccgcau uugcggccca acgggcagac uu                            42

<210> SEQ ID NO 113
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
cgucugcccg uugggccgcu ugcggcccaa cgggcagacg uu                            42

<210> SEQ ID NO 114
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gcacggcacg auguacucgu ucgaguacau cgugccgugc uu                            42

<210> SEQ ID NO 115
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ugcacggcac gauguacucu ugaguacauc gugccgugca uu                            42

<210> SEQ ID NO 116
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
augcacggca cgauguacuu uaguacaucg ugccgugcau uu                            42

<210> SEQ ID NO 117
<211> LENGTH: 42
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 117
caugcacggc acgauguacu uguacaucgu gccgugcaug uu                          42

<210> SEQ ID NO 118
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ucaugcacgg cacgauguau uuacaucgug ccgugcauga uu                          42

<210> SEQ ID NO 119
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uucaugcacg gcacgauguu uacaucgugc cgugcaugaa uu                          42

<210> SEQ ID NO 120
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
guucaugcac ggcacgaugu ucaucgugcc gugcaugaac uu                          42

<210> SEQ ID NO 121
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uguucaugca cggcacgauu uaucgugccg ugcaugaaca uu                          42

<210> SEQ ID NO 122
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uuguucaugc acggcacgau uucgugccgu gcaugaacaa uu                          42

<210> SEQ ID NO 123
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
cuuguucaug cacggcacgu ucgugccgug caugaacaag uu                42

<210> SEQ ID NO 124
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gcuuguucau gcacggcacu ugugccgugc augaacaagc uu                42

<210> SEQ ID NO 125
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ugcuuguuca ugcacggcau uugccgugca ugaacaagca uu                42

<210> SEQ ID NO 126
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gugcuuguuc augcacggcu ugccgugcau gaacaagcac uu                42

<210> SEQ ID NO 127
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
cgugcuuguu caugcacggu uccgugcaug aacaagcacg uu                42

<210> SEQ ID NO 128
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ccgugcuugu ucaugcacgu ucgugcauga acaagcacgg uu                42

<210> SEQ ID NO 129
<211> LENGTH: 42
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 129
gccgugcuug uucaugcacu gugcaugaa caagcacggc uu                                42

<210> SEQ ID NO 130
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ugccgugcuu guucaugcau uugcaugaac aagcacggca uu                               42

<210> SEQ ID NO 131
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
augccgugcu uguucaugcu ugcaugaaca agcacggcau uu                               42

<210> SEQ ID NO 132
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gaugccgugc uuguucaugu ucaugaacaa gcacggcauc uu                               42

<210> SEQ ID NO 133
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
agaugccgug cuuguucauu uaugaacaag cacggcaucu uu                               42

<210> SEQ ID NO 134
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
cagaugccgu gcuuguucau uugaacaagc acggcaucug uu                               42

<210> SEQ ID NO 135
<211> LENGTH: 42
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 135
acagaugccg ugcuuguucu ugaacaagca cggcaucugu uu          42

<210> SEQ ID NO 136
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gugcagggcg cgcaccucgu ucgaggugcg cgcccugcac uu          42

<210> SEQ ID NO 137
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
cgugcagggc gcgcaccucu ugaggugcgc gcccugcacg uu          42

<210> SEQ ID NO 138
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ucgugcaggg cgcgcaccuu uaggugcgcg cccugcacga uu          42

<210> SEQ ID NO 139
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gucgugcagg gcgcgcaccu uggugcgcgc ccugcacgac uu          42

<210> SEQ ID NO 140
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ugucgugcag ggcgcgcacu ugugcgcgcc cugcacgaca uu          42

<210> SEQ ID NO 141
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gugucgugca gggcgcgcau uugcgcgccc ugcacgacac uu            42

<210> SEQ ID NO 142
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ggugucgugc agggcgcgcu ugcgcgcccu gcacgacacc uu            42

<210> SEQ ID NO 143
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cggugucgug cagggcgcgu ucgcgcccug cacgacaccg uu            42

<210> SEQ ID NO 144
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ccggugucgu gcagggcgcu ugcgcccugc acgacaccgg uu            42

<210> SEQ ID NO 145
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
cccggugucg ugcagggcgu ucgcccugca cgacaccggg uu            42

<210> SEQ ID NO 146
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
cugcccgucc gugaacuucu ugaaguucac ggacgggcag uu            42

<210> SEQ ID NO 147
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gcugcccguc cgugaacuuu uaaguucacg gacgggcagc uu            42

<210> SEQ ID NO 148
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
agcugcccgu ccgugaacuu uaguucacgg acgggcagcu uu            42

<210> SEQ ID NO 149
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
cagcugcccg uccgugaacu uguucacgga cgggcagcug uu            42

<210> SEQ ID NO 150
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ccagcugccc guccgugaau uuucacggac gggcagcugg uu            42

<210> SEQ ID NO 151
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
accagcugcc cguccgugau uucacggacg ggcagcuggu uu            42

<210> SEQ ID NO 152
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gaccagcugc ccguccgugu ucacggacgg gcagcugguc uu            42

<210> SEQ ID NO 153
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ugaccagcug cccguccguu uacggacggg cagcugguca uu         42

<210> SEQ ID NO 154
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
cugaccagcu gcccguccgu ucggacgggc agcuggucag uu         42

<210> SEQ ID NO 155
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gcugaccagc ugcccguccu uggacgggca gcuggucagc uu         42

<210> SEQ ID NO 156
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ggcugaccag cugcccgucu ugacgggcag cuggucagcc uu         42

<210> SEQ ID NO 157
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uggcugacca gcugcccguu uacgggcagc uggucagcca uu         42

<210> SEQ ID NO 158
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
cuggcugacc agcugcccgu ucgggcagcu ggucagccag uu         42

<210> SEQ ID NO 159
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159

```
ucuggcugac cagcugcccu ugggcagcug gucagccaga uu        42
```

<210> SEQ ID NO 160
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160

```
uucuggcuga ccagcugccu uggcagcugg ucagccagaa uu        42
```

<210> SEQ ID NO 161
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161

```
cuucuggcug accagcugcu ugcagcuggu cagccagaag uu        42
```

<210> SEQ ID NO 162
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162

```
ucuucuggcu gaccagcugu ucagcugguc agccagaaga uu        42
```

<210> SEQ ID NO 163
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163

```
cucuucuggc ugaccagcuu uagcugguca gccagaagag uu        42
```

<210> SEQ ID NO 164
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164

```
acucuucugg cugaccagcu ugcuggucag ccagaagagu uu        42
```

<210> SEQ ID NO 165
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165

```
cacucuucug gcugaccagu ucuggucagc cagaagagug uu        42
```

<210> SEQ ID NO 166
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 166
ucacucuucu ggcugaccau uuggucagcc agaagaguga uu         42

<210> SEQ ID NO 167
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 167
gucacucuuc uggcugaccu uggucagcca gaagagugac uu         42

<210> SEQ ID NO 168
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 168
agucacucuu cuggcugacu ugucagccag aagagugacu uu         42

<210> SEQ ID NO 169
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 169
gagucacucu ucuggcugau uucagccaga agagugacuc uu         42

<210> SEQ ID NO 170
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 170
cgagucacuc uucuggcugu ucagccagaa gagugacucg uu         42

<210> SEQ ID NO 171
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 171
ccucgaucca ggugaucuuu uaagaucacc uggaucgagg uu         42

```
<210> SEQ ID NO 172
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
cccucgaucc aggugaucuu uagaucaccu ggaucgaggg uu                              42

<210> SEQ ID NO 173
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
gcccucgauc caggugaucu ugaucaccug gaucgagggc uu                              42

<210> SEQ ID NO 174
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ugcccucgau ccaggugauu uaucaccugg aucgagggca uu                              42

<210> SEQ ID NO 175
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uugcccucga uccaggugau uucaccugga ucgagggcaa uu                              42

<210> SEQ ID NO 176
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
cuugcccucg auccaggugu ucaccuggau cgagggcaag uu                              42

<210> SEQ ID NO 177
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
gguuucgcag ccgggcuccu uggagcccgg cugcgaaacc uu                              42
```

<210> SEQ ID NO 178
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 178
ugguuucgca gccgggcucu ugagcccggc ugcgaaacca uu                         42

<210> SEQ ID NO 179
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 179
augguuucgc agccgggcuu uagcccggcu gcgaaaccau uu                         42

<210> SEQ ID NO 180
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 180
aaugguuucg cagccgggcu ugcccggcug cgaaaccauu uu                         42

<210> SEQ ID NO 181
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 181
caugcugcuc augagcagcu ugcugcucau gagcagcaug uu                         42

<210> SEQ ID NO 182
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 182
ccaugcugcu caugagcagu ucugcucaug agcagcaugg uu                         42

<210> SEQ ID NO 183
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 183
uccaugcugc ucaugagcau uugcucauga gcagcaugga uu                         42

<210> SEQ ID NO 184

```
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
guccaugcug cucaugagcu ugcucaugag cagcauggac uu                              42

<210> SEQ ID NO 185
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
cguccaugcu gcucaugagu ucucaugagc agcauggacg uu                              42

<210> SEQ ID NO 186
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ucguccaugc ugcucaugau uucaugagca gcauggacga uu                              42

<210> SEQ ID NO 187
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gucguccaug cugcucaugu ucaugagcag cauggacgac uu                              42

<210> SEQ ID NO 188
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ggucguccau gcugcucauu uaugagcagc auggacgacc uu                              42

<210> SEQ ID NO 189
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
aggucgucca ugcugcucau uugagcagca uggacgaccu uu                              42

<210> SEQ ID NO 190
<211> LENGTH: 42
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
caggucgucc augcugcucu ugagcagcau ggacgaccug uu                            42

<210> SEQ ID NO 191
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ucaggucguc caugcugcuu uagcagcaug gacgaccuga uu                            42

<210> SEQ ID NO 192
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
aucaggucgu ccaugcugcu ugcagcaugg acgaccugau uu                            42

<210> SEQ ID NO 193
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uaucaggucg uccaugcugu ucagcaugga cgaccugaua uu                            42

<210> SEQ ID NO 194
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
agcaaccaug gcuuucgucu ugacgaaagc caugguugcu uu                            42

<210> SEQ ID NO 195
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
aagcaaccau ggcuuucguu uacgaaagcc augguugcuu uu                            42

<210> SEQ ID NO 196
<211> LENGTH: 42
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 196
caagcaacca uggcuuucgu ucgaaagcca gguugcuug uu                              42

<210> SEQ ID NO 197
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
acaagcaacc auggcuuucu ugaaagccau gguugcuugu uu                             42

<210> SEQ ID NO 198
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
aacaagcaac cauggcuuuu uaaagccaug guugcuuguu uu                             42

<210> SEQ ID NO 199
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uaacaagcaa ccauggcuuu uaagccaugg uugcuuguua uu                             42

<210> SEQ ID NO 200
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
auaacaagca accauggcuu uagccauggu ugcuuguuau uu                             42

<210> SEQ ID NO 201
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ucuuccaucu ccauuuggau uuccaaaugg agauggaaga uu                             42

<210> SEQ ID NO 202
<211> LENGTH: 42
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 202
aucuuccauc uccauuuggu uccaaaugga gauggaagau uu                          42

<210> SEQ ID NO 203
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
caucuuccau cuccauuugu ucaaauggag auggaagaug uu                          42

<210> SEQ ID NO 204
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
acaucuucca ucccauuuu uaaauggaga uggaagaugu uu                           42

<210> SEQ ID NO 205
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
auaauauaua caugucacau uugugacaug uauauauuau uu                          42

<210> SEQ ID NO 206
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
gauaauauau acaugucacu ugugacaugu auauauuauc uu                          42

<210> SEQ ID NO 207
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
agauaauaua uacaugucau uugacaugua uauauuaucu uu                          42

<210> SEQ ID NO 208
<211> LENGTH: 42
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 208 aagauaaauau auacaugucu ugacauguau auauuaucuu uu                    42

<210> SEQ ID NO 209
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
accuccacuu accuuggcau uugccaaggu aaguggaggu uu                     42

<210> SEQ ID NO 210
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
uaccuccacu uaccuuggcu ugccaaggua aguggaggua uu                     42

<210> SEQ ID NO 211
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
auaccuccac uuaccuuggu uccaagguaa guggagguau uu                     42

<210> SEQ ID NO 212
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uauaccucca cuuaccuugu ucaagguaag uggagguaua uu                     42

<210> SEQ ID NO 213
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
uucuggaaaa auucgaaguu uacuucgaau uuuccagaa uu                      42

<210> SEQ ID NO 214
<211> LENGTH: 42
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 214
cuucuggaaa aauucgaagu ucuucgaauu uuccagaag uu              42

<210> SEQ ID NO 215
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
ccuucuggaa aaauucgaau uuucgaauuu uccagaagg uu              42

<210> SEQ ID NO 216
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gccuucugga aaaauucgau uucgaauuuu ccagaaggc uu              42

<210> SEQ ID NO 217
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ugccuucugg aaaaauucgu ucgauuuuu ccagaaggca uu              42

<210> SEQ ID NO 218
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
uugccuucug gaaaaauucu ugaauuuuuc cagaaggcaa uu              42

<210> SEQ ID NO 219
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uuugccuucu ggaaaaauuu uaauuuuucc agaaggcaaa uu              42

<210> SEQ ID NO 220
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cuuugccuuc uggaaaaauu uauuuuucca gaaggcaaag uu            42

<210> SEQ ID NO 221
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gcuuugccuu cuggaaaaau uuuuuccag aaggcaaagc uu             42

<210> SEQ ID NO 222
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ggcuuugccu ucuggaaaau uuuuccaga aggcaaagcc uu             42

<210> SEQ ID NO 223
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gggcuuugcc uucuggaaau uuuuccagaa ggcaaagccc uu            42

<210> SEQ ID NO 224
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ugggcuuugc cuucuggaau uuuccagaag gcaaagccca uu            42

<210> SEQ ID NO 225
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cugggcuuug ccuucuggau uuccagaagg caaagcccag uu            42

<210> SEQ ID NO 226
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 226
acugggcuuu gccuucuggu uccagaaggc aaagcccagu uu                              42

<210> SEQ ID NO 227
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
aacugggcuu ugccuucugu ucagaaggca agcccaguu uu                              42

<210> SEQ ID NO 228
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aaacugggcu ugccuucuu uagaaggcaa agcccaguuu uu                              42

<210> SEQ ID NO 229
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
caaacugggc uuugccuucu ugaaggcaaa gcccaguuug uu                              42

<210> SEQ ID NO 230
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
gcaaacuggg cuuugccuuu uaaggcaaag cccaguuugc uu                              42

<210> SEQ ID NO 231
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
agcaaacugg gcuuugccuu uaggcaaagc ccaguuugcu uu                              42

<210> SEQ ID NO 232
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
```
cagcaaacug ggcuuugccu uggcaaagcc caguuugcug uu            42

<210> SEQ ID NO 233
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ucagcaaacu gggcuuugcu ugcaaagccc aguuugcuga uu            42

<210> SEQ ID NO 234
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gucagcaaac ugggcuuugu ucaaagccca guuugcugac uu            42

<210> SEQ ID NO 235
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ugucagcaaa cugggcuuuu uaaagcccag uuugcugaca uu            42

<210> SEQ ID NO 236
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
augucagcaa acugggcuuu uaagcccagu uugcugacau uu            42

<210> SEQ ID NO 237
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
aaugucagca acugggcuu uagcccaguu ugcugacauu uu            42

<210> SEQ ID NO 238
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238

```
caaugucagc aaacugggcu ugcccaguuu gcugacauug uu                    42

<210> SEQ ID NO 239
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
ucaaugucag caaacugggu ucccaguuug cugacauuga uu                    42

<210> SEQ ID NO 240
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uucaauguca gcaaacuggu uccaguuugc ugacauugaa uu                    42

<210> SEQ ID NO 241
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
guucaauguc agcaaacugu ucaguuugcu gacauugaac uu                    42

<210> SEQ ID NO 242
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gguucaaugu cagcaaacuu uaguuugcug acauugaacc uu                    42

<210> SEQ ID NO 243
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ggguucaaug ucagcaaacu uguuugcuga cauugaaccc uu                    42

<210> SEQ ID NO 244
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uggguucaau gucagcaaau uuuugcugac auugaaccca uu                    42
```

<210> SEQ ID NO 245
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uuggguucaa ugucagcaau uuugcugaca uugaacccaa uu                              42

<210> SEQ ID NO 246
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uuugggunca augucagcau uugcugacau ugaacccaaa uu                              42

<210> SEQ ID NO 247
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
auuuggguuc aaugucagcu ugcugacauu gaacccaaau uu                              42

<210> SEQ ID NO 248
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
aauuuggguu caaugucagu ucugacauug aacccaaauu uu                              42

<210> SEQ ID NO 249
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
aaauuugggu ucaaugucau uugacauuga acccaaauuu uu                              42

<210> SEQ ID NO 250
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
caaauuuggg uucaaugucu ugacauugaa cccaaauuug uu                              42

```
<210> SEQ ID NO 251
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ucaaauuugg guucaauguu uacauugaac ccaaauuuga uu                               42

<210> SEQ ID NO 252
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
aucaaauuug gguucaaugu ucauugaacc caaauuugau uu                               42

<210> SEQ ID NO 253
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uaucaaauuu ggguucaauu uauugaaccc aaauuugaua uu                               42

<210> SEQ ID NO 254
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
cuaucaaauu uggguucaau uuugaaccca aauuugauag uu                               42

<210> SEQ ID NO 255
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ucuaucaaau uuggguucau uugaacccaa auuugauaga uu                               42

<210> SEQ ID NO 256
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gucuaucaaa uuggguucu ugaacccaaa uuugauagac uu                                42
```

<210> SEQ ID NO 257
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
agucuaucaa auuuggguuu uaacccaaau uugauagacu uu                     42

<210> SEQ ID NO 258
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
cagucuauca aauuuggguu uacccaaauu ugauagacug uu                     42

<210> SEQ ID NO 259
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gcagucuauc aaauuugggu ucccaaauuu gauagacugc uu                     42

<210> SEQ ID NO 260
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
agcagucuau caaauuuggu uccaaauuug auagacugcu uu                     42

<210> SEQ ID NO 261
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
cagcagucua ucaaauuugu ucaaauuuga uagacugcug uu                     42

<210> SEQ ID NO 262
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
acagcagucu aucaaauuuu uaaauuugau agacugcugu uu                     42

<210> SEQ ID NO 263

```
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
aacagcaguc uaucaaauuu uaauugaua gacugcuguu uu                          42

<210> SEQ ID NO 264
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
aaacagcagu cuaucaaauu uauuugauag acugcuguuu uu                         42

<210> SEQ ID NO 265
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
aaaacagcag ucuaucaaau uuugauaga cugcuguuuu uu                          42

<210> SEQ ID NO 266
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
aaaaacagca gucuaucaau uuugauagac ugcuguuuuu uu                         42

<210> SEQ ID NO 267
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gaaaaacagc agucuaucau uugauagacu gcuguuuuc uu                          42

<210> SEQ ID NO 268
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
agaaaaacag cagucuaucu ugauagacug cuguuuuucu uu                         42

<210> SEQ ID NO 269
<211> LENGTH: 42
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
cagaaaaaca gcagucuauu uauagacugc uguuuuucug uu                             42

<210> SEQ ID NO 270
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ccagaaaaac agcagucuau uuagacugcu guuuuucugg uu                             42

<210> SEQ ID NO 271
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
accagaaaaa cagcagucuu uagacugcug uuuuucuggu uu                             42

<210> SEQ ID NO 272
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gaccagaaaa acagcagucu ugacugcugu uuucuggucu uu                             42

<210> SEQ ID NO 273
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
agaccagaaa aacagcaguu uacugcuguu uuucuggucu uu                             42

<210> SEQ ID NO 274
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
cagaccagaa aaacagcagu ucugcuguuu uucuggucug uu                             42

<210> SEQ ID NO 275
<211> LENGTH: 42
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 275
ucagaccaga aaaacagcau ugcuguuuu ucuggucuga uu                        42

<210> SEQ ID NO 276
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
gucagaccag aaaaacagcu ugcuguuuuu cuggucugac uu                       42

<210> SEQ ID NO 277
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
ggucagacca gaaaaacagu ucuguuuuuc uggucugacc uu                       42

<210> SEQ ID NO 278
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
cggucagacc agaaaaacau uguuuuucu ggucugaccg uu                        42

<210> SEQ ID NO 279
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
acggucagac cagaaaaacu uguuuuucug gucugaccgu uu                       42

<210> SEQ ID NO 280
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uuguacuuca ugaggguugu caacccuca ugaaguacaa uu                        42

<210> SEQ ID NO 281
<211> LENGTH: 42
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 281
aguuauugcg uaccuuguau uuacaaggua cgcaauaacu uu                              42

<210> SEQ ID NO 282
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
caguuauugc guaccuuguu uacaagguac gcaauaacug uu                              42

<210> SEQ ID NO 283
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
acaguuauug cguaccuugu ucaagguacg caauaacugu uu                              42

<210> SEQ ID NO 284
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
aacaguuauu gcguaccuuu uaagguacgc aauaacuguu uu                              42

<210> SEQ ID NO 285
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
aaacaguuau ugcguaccuu uagguacgca auaacuguuu uu                              42

<210> SEQ ID NO 286
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
caaacaguua uugcguaccu ugguacgcaa uaacuguuug uu                              42

<210> SEQ ID NO 287
<211> LENGTH: 42
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 287
ccaaacaguu auugcguacu uguacgcaau aacuguuugg uu                    42

<210> SEQ ID NO 288
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
accaaacagu auugcguau uuacgcaaua acuguuuggu uu                     42

<210> SEQ ID NO 289
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
uaccaaacag uuauugcguu uacgcaauaa cuguuuggua uu                    42

<210> SEQ ID NO 290
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
auaccaaaca guuauugcgu ucgcaauaac uguuugguau uu                    42

<210> SEQ ID NO 291
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
aauaccaaac aguuauugcu ugcaauaacu guuugguauu uu                    42

<210> SEQ ID NO 292
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
aaauaccaaa caguuauugu ucaauaacug uuugguauuu uu                    42

<210> SEQ ID NO 293
<211> LENGTH: 42
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 293
aaaauaccaa acaguuauuu uaauaacugu uugguauuuu uu     42

<210> SEQ ID NO 294
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
caaaauacca aacaguuauu uauaacuguu ugguauuuug uu     42

<210> SEQ ID NO 295
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
ucaaaauacc aaacaguuau uuaacuguuu gguauuuuga uu     42

<210> SEQ ID NO 296
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aucaaaauac caaacaguuu uaacuguuug guauuuugau uu     42

<210> SEQ ID NO 297
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
caucaaaaua ccaaacaguu uacuguuugg uauuuugaug uu     42

<210> SEQ ID NO 298
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
gcaucaaaau accaaacagu ucuguuuggu auuuugaugc uu     42

<210> SEQ ID NO 299
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ugcaucaaaa uaccaaacau uguuuggua uuuugaugca uu            42

<210> SEQ ID NO 300
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
cugcaucaaa auaccaaacu uguuugguau uuugaugcag uu            42

<210> SEQ ID NO 301
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ucugcaucaa aauaccaaau uuuggguauu uugaugcaga uu            42

<210> SEQ ID NO 302
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
aucugcauca aaauaccaau uuugguauuu ugaugcagau uu            42

<210> SEQ ID NO 303
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
caucugcauc aaaauaccau uugguauuuu gaugcagaug uu            42

<210> SEQ ID NO 304
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ucaucugcau caaaauaccu ugguauuuug augcagauga uu            42

<210> SEQ ID NO 305
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 305
cucaucugca ucaaaauacu uguauuuga ugcagaugag uu                    42

<210> SEQ ID NO 306
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ucucaucugc aucaaaauau uuauuugau gcagaugaga uu                    42

<210> SEQ ID NO 307
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gauauuuuac uuuagcucgu ucgagcuaaa guaaaauauc uu                   42

<210> SEQ ID NO 308
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
agauauuuua cuuuagcucu ugagcuaaag uaaaauaucu uu                   42

<210> SEQ ID NO 309
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uagauauuuu acuuuagcuu uagcuaaagu aaaauaucua uu                   42

<210> SEQ ID NO 310
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uuagauauuu uacuuuagcu ugcuaaagua aaauaucuaa uu                   42

<210> SEQ ID NO 311
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
```

```
guuagauauu uuacuuuagu ucuaaaguaa aauaucuaac uu                    42

<210> SEQ ID NO 312
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uguuagauau uuuacuuuau uuaaaguaaa auaucuaaca uu                    42

<210> SEQ ID NO 313
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
cuguuagaua uuuuacuuuu uaaaguaaaa uaucuaacag uu                    42

<210> SEQ ID NO 314
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ccuguuagau auuuuacuuu uaaguaaaau aucuaacagg uu                    42

<210> SEQ ID NO 315
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
accuguuaga uauuuuacuu uaguaaaaua ucuaacaggu uu                    42

<210> SEQ ID NO 316
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
caccuguuag auauuuuacu uguaaaauau cuaacaggug uu                    42

<210> SEQ ID NO 317
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
```
ucaccuguua gauauuuuau uuaaaauauc uaacagguga uu                              42

<210> SEQ ID NO 318
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uucaccuguu agauauuuuu uaaaauaucu aacaggugaa uu                              42

<210> SEQ ID NO 319
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uucaacccuc acaccuuuuu uaaaaggugu gaggguugaa uu                              42

<210> SEQ ID NO 320
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
guucaacccu cacaccuuuu uaaaggugug aggguugaac uu                              42

<210> SEQ ID NO 321
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
aguucaaccc ucacaccuuu uaagguguga ggguugaacu uu                              42

<210> SEQ ID NO 322
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
gaguucaacc cucacaccuu uaggugugag gguugaacuc uu                              42

<210> SEQ ID NO 323
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
ugaguucaac ccucacaccu uggugugagg guugaacuca uu                              42

<210> SEQ ID NO 324
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uugaguucaa cccucacacu ugugugaggg uugaacucaa uu                           42

<210> SEQ ID NO 325
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
auugaguuca acccucacau uugugagggu ugaacucaau uu                           42

<210> SEQ ID NO 326
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ucagccgcug ucacacgcac ag                                                 22

<210> SEQ ID NO 327
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
gcugtcacac gcaca                                                         15

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
cagccgcugu cacacgcaca                                                    20

<210> SEQ ID NO 329
<211> LENGTH: 22
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 329
ucagccgcug ucacacgcac ag                                              22
```

METHODS AND COMPOSITIONS OF SHORT SMALL HAIRPIN RNAS AND MICRORNAS FOR WOUND HEALING

This application is a Continuation of U.S. application Ser. No. 15/752,182, filed Feb. 12, 2018, which is a U.S. National Stage Entry of PCT/US2016/046884, filed Aug. 12, 2016, which claims the benefit of U.S. Provisional Application No. 62/204,957, filed Aug. 13, 2015, each of which are incorporated herein by reference in their entirety.

STATEMENT REGARDING FEDERALLY SPONSORED RESEARCH

This invention was made in part during work supported by grant R43GM101725 and R44GM101725 (BHJ) from the National Institutes of Health. The government has certain rights in the invention.

CROSS-REFERENCE TO RELATED APPLICATIONS

This application claims the benefit of priority to U.S. Provisional Application No. 62/204,957 filed on Aug. 13, 2015, which incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 10, 2016, is named 40220710301 SL.txt and is 91,835 bytes in size.

BACKGROUND

Wound healing is an orchestrated physiological process in which multiple cell types interact to close a physical insult. Dysregulation of wound healing contributes to the pathology of various diseases. New approaches are needed to ameliorate wound healing in these pathological settings.

SUMMARY OF THE INVENTION

Disclosed herein, in certain embodiments, is a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs. In some embodiments, the RNA transcript is encoded by an Egl nine homolog 1 (EGLN1) gene, wherein the EGLN1 gene, minus introns, is represented by a sequence selected from SEQ ID NO. 1 and SEQ ID NO. 2. In some embodiments, RNA transcript is a transcript corresponding to human PHD2 (SEQ ID NO. 1). In some embodiments, RNA transcript is a transcript corresponding to mouse Phd2 (SEQ ID NO. 2). In some embodiments, the sshRNA targets both human PHD2 (SEQ ID NO. 1) and mouse Phd2 (SEQ ID NO. 2). In some embodiments, the sshRNA consists of the antisense sequence, the sense sequence, the loop region, an optional overhang sequence, and an optional conjugate moiety. In some embodiments, loop region is selected from a direct connection, 1 nucleotide and 2 nucleotides in length. In some embodiments, the overhang sequence is from about 1 nucleotide to about 2 nucleotides. In some embodiments, the conjugate moiety is a detectable label. In some embodiments, the antisense sequence is from about 15 nucleotides to about 19 nucleotides in length. In some embodiments, the antisense sequence is from about 16 nucleotides to about 19 nucleotides in length. In some embodiments, the antisense sequence is from about 60% complementary to 100% complementary to the PHD2 transcript. In some embodiments, the antisense sequence is from about 80% complementary to 100% complementary to the PHD2 transcript. In some embodiments, the sense sequence is from about 10 nucleotides to about 19 nucleotides in length. In some embodiments, the sense sequence is from about 11 nucleotides to about 19 nucleotides in length. In some embodiments, the sense sequence is from about 80% complementary to 100% complementary to the antisense sequence. In some embodiments, at least one nucleotide comprises a chemical modification. In some embodiments, the chemical modification increases the stability of the shRNA in a biological fluid at least about 20%. In some embodiments, the chemical modification increases the stability of the shRNA in a biological fluid about 1% to about 10000%. In some embodiments, the chemical modification is a sugar modification. In some embodiments, the sugar modification is chosen from: 2'-O-methyl, 2'-H, and 2'-F. In some embodiments, the sshRNA is represented by a sequence selected from SEQ ID NOS: 5-8, 11-31, 49-325.

Disclosed herein, in certain embodiments, is a microRNA (miRNA) antagonist comprising an antisense strand capable of hybridizing to and inhibiting miR-210. In some embodiments, the miR-210 is represented by SEQ ID NO. 3. In some embodiments, the miRNA antagonist comprises a sequence from about 60% to 100% complementary to the miR-210 that is represented by SEQ ID NO. 3. In some embodiments, the miRNA antagonist reduces an amount or an activity of the miR-210 from about 1% to about 99.9%. In some embodiments, the miRNA antagonist reduces an amount or an activity of the miR-210 from about 10% to about 99.9%. In some embodiments, at least one ribonucleotide comprises a chemical modification. In some embodiments, every ribonucleotide comprises a chemical modification. In some embodiments, the chemical modification is a sugar modification. In some embodiments, the sugar modification comprises a 2'-O-methyl modification, a LNA modification, a DNA modification, or a 2'-F modification. In some embodiments, the sugar modification comprises a 2'-O-methyl modification, a 2'-H, a LNA modification, a DNA modification, or a 2'-F modification. In some embodiments, the sugar modification is a 2'-O-methyl modification. In some embodiments, the sugar modification is a LNA modification. In some embodiments, the miRNA antagonist comprises phosphorothioate internucleotide linkages. In some embodiments, the miRNA antagonist comprises a backbone modification. In some embodiments, backbone modification is selected from a C3 spacer or ZEN. In some embodiments, the miRNA antagonist comprises a 2'-O-methyl modification at every position and three phosphorothioate internucleotide linkages at consecutive residues at both the 5'- and 3'-end. In some embodiments, the miRNA antagonist comprises phosphorothioate linkages at every position and 2'-O-methyl modifications at positions 1, 3, 4, 6, 7, 9, 10, 12, 13, and 15 and LNA modifications at positions 2, 5, 8, 11, and 14. In some embodiments, the miRNA antagonist comprises 2'-O-methyl modifications at every position and ZEN modifications between position 1 and 2 and also at the 3'-end. In some embodiments, the modification reduces miRNA inhibitory activity from about 0.0000000001% to about 50%. In some embodiments, the miRNA antagonist is represented by a sequence selected from SEQ ID NOS: 32-43, 326-328.

Disclosed herein, in certain embodiments, is a pre-miRNA mimic for increasing a steady state level of a mature miR-21 comprising: (a) a sense sequence; (b) an antisense sequence; and (c) a loop region, wherein the length of the loop region is the length of 2 nucleotides or less. In some embodiments, the mature miR-21 is represented by SEQ ID NO.4. In some embodiments, the sense and antisense sequences are from about 60% to 100% complementary. In some embodiments, the loop region consists of a direct connection, or consists of 1-2 nucleotides or nucleotide moieties. In some embodiments, the pre-miRNA mimic further comprises an overhang region from about 1 nucleotide to about 2 nucleotides. In some embodiments, the pre-miRNA mimic has at least one nucleotide modified. In some embodiments, the modification reduces miRNA-mediated repressive activity from about 0.0000000001% to about 50%. In some embodiments, the pre-miRNA mimic increases a steady-state level of the mature miRNA from about 1% to about 10000%. In some embodiments, the pre-miRNA mimic is represented by a sequence selected from SEQ ID NOS: 44-48.

Disclosed herein, in certain embodiments, is a pharmaceutical composition comprising a pharmaceutically-acceptable substrate, carrier or salt, and at least one RNA selected from: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a pharmaceutical composition comprising a pharmaceutically-acceptable substrate, carrier or salt, and a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2. Disclosed herein, in certain embodiments, is a pharmaceutical composition comprising a pharmaceutically-acceptable substrate, carrier or salt, and a microRNA (miRNA) antagonist comprising an antisense strand capable of hybridizing to and inhibiting miR-210. Disclosed herein, in certain embodiments, is a pharmaceutical composition comprising a pharmaceutically-acceptable substrate, carrier or salt, and a pre-miRNA mimic for increasing a steady state level of a mature miR-21 comprising: (a) a sense sequence; (b) an antisense sequence; and (c) a loop region, wherein the length of the loop region is the length of 2 nucleotides or less. In some embodiments, the short small hairpin RNA (sshRNA) has an antisense sequence that is from about 60% complementary to 100% complementary to the PHD2 transcript. In some embodiments, the miRNA antagonist comprises a sequence from about 60% to 100% complementary to the miR-210 that is represented by SEQ ID NO. 3. In some embodiments, the pre-miRNA mimic has the sense and antisense sequences that are from about 60% to 100% complementary. In some embodiments, the pharmaceutically-acceptable substrate is a mesh or a dressing. In some embodiments, the mesh is a layered mesh.

Disclosed herein, in certain embodiments, is a pharmaceutical composition comprising a pharmaceutically-acceptable substrate, carrier or salt, and a combination of RNAs selected from: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a pharmaceutical composition comprising a pharmaceutically-acceptable substrate, carrier or salt, and a combination of RNAs comprising: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; and (b) a microRNA (miRNA) antagonist comprising an antisense strand capable of hybridizing to and inhibiting miR-210. Disclosed herein, in certain embodiments, is a pharmaceutical composition comprising a pharmaceutically-acceptable substrate, carrier or salt, and a combination of RNAs comprising: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a pharmaceutical composition comprising a pharmaceutically-acceptable substrate, carrier or salt, and a combination of RNAs comprising: (b) a microRNA (miRNA) antagonist comprising an antisense strand capable of hybridizing to and inhibiting miR-210 and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a pharmaceutical composition comprising a pharmaceutically-acceptable substrate, carrier or salt, and a combination of RNAs comprising: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. In some embodiments, the short small hairpin RNA (sshRNA) has an antisense sequence that is from about 60% complementary to 100% complementary to the PHD2 transcript. In some embodiments, the miRNA antagonist comprises a sequence from about 60% to 100% complementary to the miR-210 that is represented by SEQ ID NO. 3. In some embodiments, the pre-miRNA mimic has the sense and antisense sequences that are from about 60% to 100% complementary. In some embodiments, the pharmaceutically-acceptable substrate is a mesh or a dressing. In some embodiments, the composition is formulated for topical administration.

In some embodiments, the mesh is a layered mesh. In some embodiments, the pharmaceutically-acceptable substrate is formed by layer-by-layer (LbL) fabrication. LbL deposition creates a thin film, formed by alternating layers of oppositely charged materials. Formation of layers may comprise a technique selected from immersion, spin, spray, electromagnetism or fluidics. In some embodiments, the composition is formulated for topical administration. In some embodiments, the layered mesh may be degradable in an aqueous environment. The layered mesh may conform to a wound. In some embodiments, the layer-by-layer film comprises a LayerForm™ coating. The LayerForm™ coating may be chosen from coatings with various release profiles, to release the oligonucleotides disclosed herein at an optimal rate for the subject.

Disclosed herein, in certain embodiments, is a method for treating a wound in a subject in need thereof comprising administering a therapeutically effective amount of a composition selected from: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less; and a combination thereof. In some embodiments, the wound is a chronic wound. In some embodiments, the wound is a non-healing wound. In some embodiments, the subject has diabetes mellitus. In some embodiments, the wound is a skin wound. In some embodiments, the method comprises administering the composition topically. In some embodiments, the method comprises a dressing, wherein the dressing comprises the composition.

Disclosed herein, in certain embodiments, is an RNA selected from: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less; and any combination thereof, for use in a method of treating a wound in an animal or human. In some embodiments, disclosed herein, is a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs, for use in a method of treating a wound in an animal or human. In some embodiments, disclosed herein, is a microRNA (miRNA) antagonist comprising an antisense strand capable of hybridizing to and inhibiting miR-210, for use in a method of treating a wound in an animal or human. In some embodiments, disclosed herein, is a pre-miRNA mimic for increasing a steady state level of a mature miR-21 comprising: (a) a sense sequence; (b) an antisense sequence; and (c) a loop region, wherein the length of the loop region is the length of 2 nucleotides or less, for use in a method of treating a wound in an animal or human.

Disclosed herein, in certain embodiments, is an RNA selected from: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less; and any combination thereof, for treatment of a wound in a subject. In some embodiments, disclosed herein, is a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs, for treatment of a wound in a subject. In some embodiments, disclosed herein, is a microRNA (miRNA) antagonist comprising an antisense strand capable of hybridizing to and inhibiting miR-210, for treatment of a wound in a subject. In some embodiments, disclosed herein, is a pre-miRNA mimic for increasing a steady state level of a mature miR-21 comprising: (a) a sense sequence; (b) an antisense sequence; and (c) a loop region, wherein the length of the loop region is the length of 2 nucleotides or less, for treatment of a wound in a subject.

Disclosed herein, in certain embodiments, is a kit comprising: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less.

Disclosed herein, in certain embodiments, is a method for treating a wound in a subject in need thereof comprising contacting a cell with a therapeutically effective amount of a composition selected from: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less; and a combination thereof. Disclosed herein, in certain embodiments, is a method for treating a wound in a subject in need thereof comprising contacting a cell with a therapeutically effective amount of a composition comprising a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2. Disclosed herein, in certain embodiments, is a method for treating a wound in a subject in need thereof comprising contacting a cell with a therapeutically effective amount of a composition comprising a microRNA (miRNA) antagonist comprising an antisense strand capable of hybridizing to and inhibiting miR-210. Disclosed herein, in certain embodiments, is a method for treating a wound in a subject in need thereof comprising contacting a cell with a therapeutically effective amount of a composition comprising a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a method for treating a wound in a subject in need thereof comprising contacting a cell with a therapeutically effective amount of a composition comprising (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; and (b) a microRNA (miRNA) antagonist comprising an antisense strand capable of hybridizing to and inhibiting miR-210. Disclosed herein, in certain embodiments, is a method for treating a wound in a subject in need thereof comprising contacting a cell with a therapeutically effective amount of a composition comprising (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a method for treating a wound in a subject in need thereof comprising contacting a cell with a therapeutically effective amount of a composition comprising (b) a microRNA (miRNA) antagonist comprising an antisense strand capable of hybridizing to and inhibiting miR-210; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. Disclosed herein, in certain embodiments, is a method for treating a wound in a subject in need thereof comprising contacting a cell with a therapeutically effective amount of a composition comprising: (a) a short small hairpin RNA (sshRNA) for inhibiting prolyl hydroxylase domain-containing protein 2 (PHD2) comprising: (a) an antisense sequence that is capable of hybridizing to an RNA transcript encoding prolyl hydroxylase domain-containing protein 2; and (b) a sense sequence, wherein the sense and antisense sequences form a stem having a length of less than or equal to 19 base pairs; (b) a microRNA (miRNA) antagonist comprising an antisense strand capable of hybridizing to and inhibiting miR-210; and (c) a pre-miRNA mimic for increasing a steady state level of a mature miR-21 comprising: (a) a sense sequence; (b) an antisense sequence; and (c) a loop region, wherein the length of the loop region is the length of 2 nucleotides or less. In some embodiments, the short small hairpin RNA (sshRNA) has an antisense sequence that is from about 60% complementary to 100% complementary to the PHD2 transcript. In some embodiments, the miRNA antagonist comprises a sequence from about 60% to 100% complementary to the miR-210 that is represented by SEQ ID NO. 3. In some embodiments, the pre-miRNA mimic has the sense and antisense sequences that are from about 60% to 100% complementary. In some embodiments, the wound is a chronic wound. In some embodiments, the wound is a non-healing wound. In some embodiments, the subject has diabetes mellitus. In some embodiments, the wound is a skin wound. In some embodiments, the cell is a keratinocyte. In some embodiments, the cell is a fibroblast. In some embodiments, the method comprises administering the composition topically. In some embodiments, the method comprises a dressing, wherein the dressing comprises the composition.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which principles of the invention are utilized, and the accompanying figures of which:

FIG. 2A illustrates the expression of human PHD2 in human embryonic kidney 293FT cells transfected with increasing amounts of sshRNA (SG302) or siRNA (SG303) targeting PHD2 or a control sshRNA (SG221c). FIG. 2B illustrates the expression of mouse PHD2 in mouse NIH3T3 fibroblasts transfected with increasing amounts of PHD2-targeting sshRNAs (SG400 and SG402), PHD2-targeting siRNA (SG403) or a control sshRNA (SG221c).

FIG. 3A illustrates results of a luciferase reporter assay in human embryonic kidney 293FT cells co-transfected with a plasmid of firefly luciferase (f-Luc) under the control of a promoter containing HIF-1α responsive elements or a plasmid that constitutively expresses Renilla luciferase (r-Luc) and individual sshRNAs targeting PHD2 (SG300, SG301, or SG302) or with a control sshRNA (NSC sshRNA). FIG. 3B illustrates Western blotting studies of HIF-1α and Lamin protein in Human embryonic kidney 293FT cells. FIG. 3C illustrates qRT-PCR of VEGF (lanes 1, 4, 7, 10, 13, 16, and 19), HSP90 (lanes 2, 5, 8, 11, 14, 17, and 20), and HSP70 (lanes 3, 6, 9, 12, 15, 18, and 21) in human embryonic kidney 293FT cells transfected with increasing amounts of SG302.

FIG. 4A illustrates qRT-PCR of human PHD2 transcript in human primary normal human epidermal keratinocytes (NHEK) transfected with increasing amounts of SG302 or a modified sshRNA targeting PHD2 (SG302m1). FIG. 4B illustrates qRT-PCR of mouse Phd2 transcript in mouse NIH3T3 fibroblasts transfected with increasing amounts of SG402, a modified sshRNA targeting PHD2 (SG402m1), or a scrambled control sshRNA (SG402-scr).

FIG. 4C illustrates qRT-PCR of mouse PHD2 (mPHD2) transcript in mouse NIH3T3 fibroblasts transfected with increasing amounts of an unmodified sshRNA targeting PHD2 (SG404) or SG402m1.

FIG. 5A illustrates qRT-PCR assays for IFN-β in cells treated with no inhibitor, poly-inosine/cytosine (polyI:C), SG302, or SG302m1. FIG. 5B illustrates qRT-PCR assays for IL-6 in cells treated with no inhibitor, polyI:C, SG302, or SG302m1. FIG. 5C illustrates qRT-PCR assays for TNF-α in cells treated with no inhibitor, polyI:C, SG302, or SG302m1. FIG. 5D illustrates qRT-PCR for IFN-β in cells treated with no inhibitor, polyI:C, SG402, SG402m1, or SG404. FIG. 5E illustrates qRT-PCR assays for IL-6 in cells treated with no inhibitor, polyI:C, SG402, SG402m1, or SG404. FIG. 5F illustrates qRT-PCR assays for TNF-α in cells treated with no inhibitor, polyI:C, SG402, SG402m1, or SG404.

FIG. 7A illustrates possible modification patterns for a miR-210 miRNA antagonist. FIG. 7A discloses SEQ ID NOS 3 and 329, respectively, in order of appearance. FIG. 7B illustrates qRT-PCR of human PHD2 transcript in human HaCaT keratinocytes transfected with the following: no inhibitor; an sshRNA targeting human PHD2 (SG302); a control sshRNA (ssh-NSC); SG302 and a LNA-modified miR-210, miRNA antagonist (SG302+LNA210); SG302 and a 2'-O-methyl-modified miR-210 miRNA antagonist (SG302+2'-O-methyl 210); ssh-NSC and a LNA-modified control miRNA antagonist (ssh-NSC+LNA-NSC); LNA210; 2'-O-methyl 210; and LNA-NSC. FIG. 7C illustrates miRNA qRT-PCR (miR-qRT-PCR) of miR-210 miRNA in human HaCaT keratinocytes transfected with the following: no inhibitor; SG302; ssh-NSC; SG302+LNA210; SG302+2'-O-methyl 210; ssh-NSC+LNA-NSC; LNA210; 2'-O-methyl 210; and LNA-NSC. FIG. 7D illustrates a luciferase assay with a miR-210 reporter in human HaCaT keratinocytes transfected with no inhibitor or a miR-210 mimic. FIG. 7E illustrates a luciferase assay with a miR-210 reporter in human HaCaT keratinocytes treated with the following: no inhibitor (column 1); $CoCl_2$ (column 2); $CoCl_2$ and increasing concentrations of DNA modified miR-210 miRNA antagonist (DNA210; columns 3-6); $CoCl_2$ and increasing concentrations of miR-210 miRNA antagonist (RNA210; columns 7-10); $CoCl_2$ and increasing concentrations of 2'-O-methyl modified miR-210 miRNA antagonist (2'-O-methyl 210; columns 11-14); $CoCl_2$ and increasing concentrations of LNA modified miR-210 miRNA antagonist (LNA210; columns 15-18); and $CoCl_2$ and increasing concentrations of a control miRNA antagonist (NSC; columns 19-22). FIG. 7F illustrates qRT-PCR of human PHD2 transcript in human primary keratinocytes transfected with increasing amounts of an sshRNA targeting human PHD2 (SG302) and a control sshRNA (SG221c). FIG. 7G illustrates qRT-PCR of miR-210 in human primary keratinocytes transfected with increasing amounts of an sshRNA targeting human PHD2 (SG302) and a control sshRNA (SG221c). FIG. 7H illustrates qRT-PCR of mouse PHD2 transcript in NIH-3T3 cells transfected with increasing amounts of an sshRNA targeting mouse PHD2 (SG404). FIG. 7I illustrates qRT-PCR of miR-210 in NIH-3T3 cells transfected with increasing amounts of an sshRNA targeting mouse PHD2 (SG404). FIG. 7J illustrates relative expression of PHD2 and miR-210 both alone and in combination with PHD2-targeting SG302 sshRNA and antimiR-210 (SG603) in HaCaT cells.

FIG. 8A illustrates qRT-PCR for IFN-β in MRC-5 lung fibroblasts treated with: no inhibitor; polyI:C; a DNA modified miR-210 miRNA antagonist (210 DNA anti); a miR-210 miRNA antagonist (210 RNA anti); a 2'-O-methyl modified miR-210 miRNA antagonist (210 2'-O-methyl anti); a LNA modified miR-210 miRNA antagonist (210 LNA anti); and a LNA modified control miRNA antagonist (210 NSC (LNA)). FIG. 8B illustrates qRT-PCR for IL-6 in cells treated with: no inhibitor; polyI:C; 210 DNA anti; 210 RNA anti; 210 2'-O-methyl anti; 210 LNA anti; and 210 NSC (LNA). FIG. 8C illustrates qRT-PCR for TNF-α in cells treated with: no inhibitor; polyI:C; 210 DNA anti; 210 RNA anti; 210 2'-O-methyl anti; 210 LNA anti; and 210 NSC (LNA).

FIG. 10A illustrates the percentage of original wound area over 25 days in the Layer by Layer group (LbL), A6K, HiPerFect, and Control treatment groups. FIG. 10B illustrates the days until the wound closed in the LbL, A6K, HiPerFect, and Control treatment groups. FIG. 10C illustrates the percentage of original wound area over 25 days in the Untreated, SG404, SG603, and SG221c treatment groups. FIG. 10D illustrates the days until the wound closed in each treatment group. FIG. 10E illustrates representative images of fluorescence staining at day 7 for untreated or LbL topical treatment of control sshRNAs (SG221c) or SG404 sshRNA treatment group. FIG. 10F illustrates computed values (integrated density) of vWF staining for each treatment group.

FIG. 11A illustrates qRT-PCR of human PHD2 transcript in human kidney 293FT cells transfected with either 1 nM or 10 nM of the following: no inhibitor; sshRNAs designed to target human PHD2 (SG302, SG304-SG309); and sshRNAs designed to target mouse PHD2 (SG400-SG402); and a control sshRNA (NSC). FIG. 11B illustrates qRT-PCR of mouse PHD2 (mPHD2) transcript in mouse NIH3T3 fibroblasts transfected with increasing amounts of sshRNAs designed to target mouse PHD2 (SG404) or a modified sshRNA designed to target human PHD2 (SG302m1). FIG. 11C illustrates qRT-PCR of human PHD2 (hPHD2) transcript in human HaCaT keratinocytes transfected with increasing amounts of sshRNAs designed to target either human PHD2 or mouse PHD2 (SG312, and SG314-SG316) or a modified sshRNA designed to target human PHD2 (SG302m1). FIG. 11D illustrates qRT-PCR of mouse PHD2 (mPHD2) transcript in mouse NIH3T3 fibroblasts transfected with increasing amounts of sshRNAs designed to target either human PHD2 or mouse PHD2 (SG312, and SG314-SG316) or a modified sshRNA designed to target human PHD2 (SG302m1).

FIG. 12A illustrates the percent scratch closure at 24 hours (24 h), 48 h, and 72 h of human HaCaT keratinocytes transfected with the following: an sshRNA targeting human PHD2 (SG302) and a LNA-modified miR-210 miRNA antagonist (SG302+LNA210); SG302 and a 2'-O-methyl-modified miR-210 miRNA antagonist (SG302+2'-O-methyl 210); and a control sshRNA (ssh-NSC) and a LNA-modified control miRNA antagonist (ssh-NSC+LNA-NSC). FIG. 12B provides representative images of the scratch wounds at 0 hours (0 h), 24 h, and 48 h of human HaCaT keratinocytes transfected with SG302+LNA210, SG302+2'-O-methyl 210, and ssh-NSC+LNA-NSC.

FIG. 13A-FIG. 13E illustrate designs for pre-miRNA mimics of miR-21 and disclose SEQ ID NOS 44-48, respectively. FIG. 13F illustrates a luciferase assay with a miR-21 reporter in human 293FT cells treated with increasing concentrations of the following: SG701 (FIG. 13A), SG702 (FIG. 13B), SG703 (FIG. 13C), SG703 (replicate 2) (FIG. 13C), SG704 (FIG. 13D), miRIDIAN miR-21mimic (Dharmacon, positive control) and cel-67 mimic (Dharmacon, miRIDIAN miRNA mimic negative control #1).

FIG. 14A illustrates the average (Ave) number of Oct4-GFP-positive colonies in the mock, miRIDIAN, and Somagenics groups at 10, 12, 14, and 16 days after transfection. FIG. 14B illustrates a percentage of GFP-positive cells relative to cells transfected with a control vector over a time course in the seed mutant, MiRIDIAN, and Somagenics treatment groups.

DETAILED DESCRIPTION OF THE INVENTION

Figure 1:
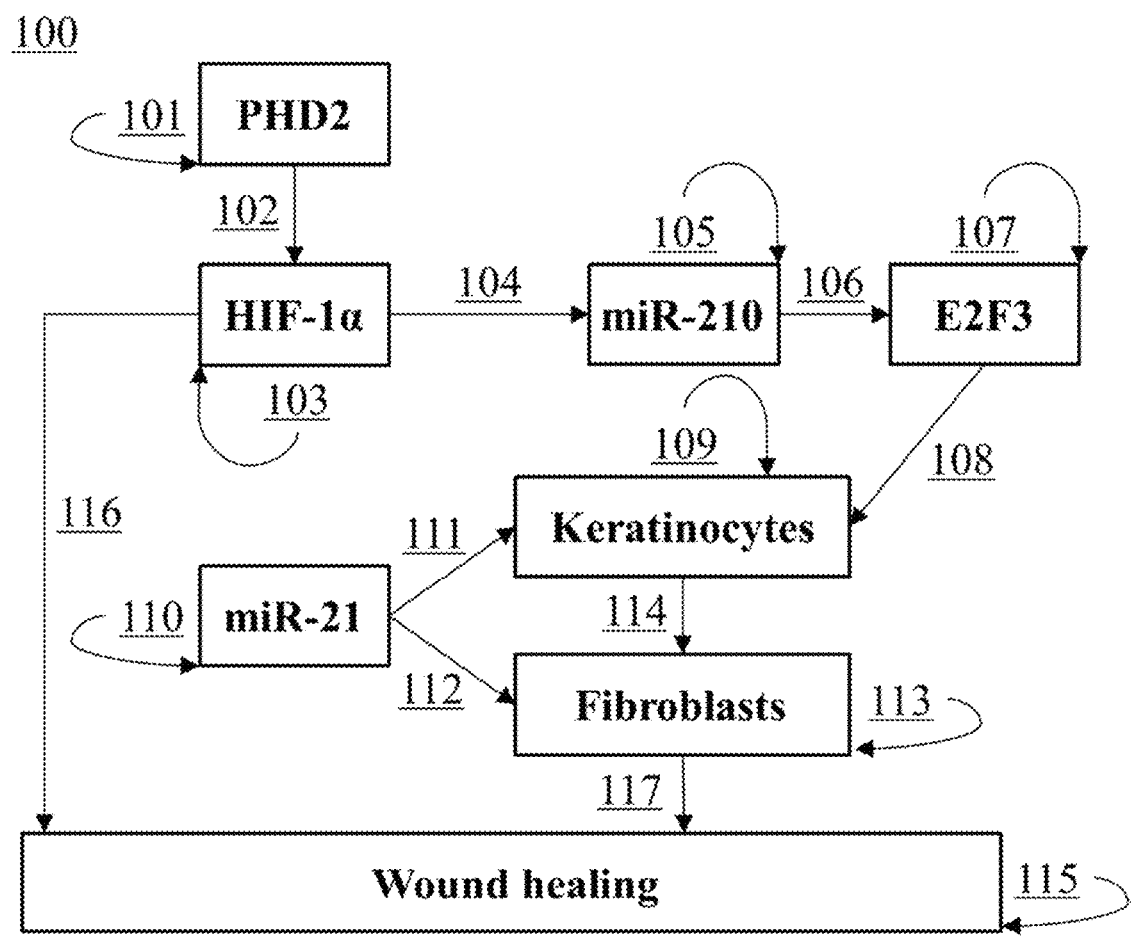
FIG. 1 diagrams an exemplary HIF-1α wound healing network.

Disclosed herein are oligonucleotides for use alone or in combination in the treatment of wounds in a subject in need thereof. Oligonucleotides disclosed herein include short small hairpin RNAs (sshRNAs), micro-RNA (miRNA) antagonists and pre-miRNA mimics. These oligonucleotides modify the activity and/or expression of RNAs.

Wound healing is an orchestrated physiological process in which multiple cell types interact to close a physical insult. Dysregulation of wound healing contributes to the pathology of various diseases. Wound management and healing is currently a great concern for human patients suffering from diabetes mellitus (DM). Due to peripheral neuropathy, a complication of DM, wounds, such as foot ulcers, may often go unnoticed by the diabetic patient. New approaches are needed to ameliorate wound healing in these pathological settings.

Wound healing is a complex and dynamic biological process with a least three overlapping phases: 1) an inflammatory phase, characterized by vasoconstriction, platelet aggregation, clot formation and phagocytosis, which usually occurs in the first 2-5 days of initial insult or injury; 2) a proliferative phase, characterized by granulation (e.g., fibroblasts lay a collagen bed), angiogenesis (e.g., new vessel growth), contraction (e.g., edges of wounds pull together) and epithelialization, which usually occurs from 2 days-3 weeks of initial insult or injury; and 3) a remodeling phase, in which new collagen forms to provide tensile strength across the wound (3 weeks-2 years from initial insult or injury). A successful wound management strategy should seek rapid wound closure through effective inflammatory and proliferative phases, leading to a productive remodeling phase with minimized risk of infection.

There are several biological pathways and mechanisms involved in wound healing, any of which may be targeted by the oligonucleotides disclosed herein. However, exemplified herein, is the pathway involving prolyl hydroxylase domain-containing protein 2 (PHD2), an enzyme encoded by the Egl nine homolog 1 (EGLN1) gene. It is also known as hypoxia-inducible factor prolyl hydroxylase 2 (HIF-PH2). PHD2 is critical for targeting hypoxia-inducible factor 1 alpha (HIF-1α) for polyubiquitylation and subsequent degradation. Under normoxia, PHD2 hydroxylates specific proline residues in cytoplasmic HIF-1α that are recognized by VHL, a signal for ubiquitylation to introduce Ubiquitin residues. Ubiquitylated HIF-1α is rapidly degraded through the proteasome pathway. Under hypoxia, PHD2 stays inactive and as a result, HIF-1α becomes stabilized and translocates to the nucleus. It dimerizes with ARNT to bind HRE elements in promoters of a large number of genes. Upon binding to HRE, HIF-1α/ARNT complex recruits CBP/p300 to activate gene expression. A knockdown of PHD2 results in an increase in levels of HIF-1α under normoxic conditions. HIF-1α activates multiple factors that enhance overall wound healing through stimulating cell survival, motility and proliferation, angiogenesis, progenitor cell recruitment and re-epithelialization, including, but not limited to, VEGF, EPO, PDGF, PLGF, VEGF-r1, ANG-1, ANG-2, iNOS, IGF2, TGF-beta, PAI-1, SDF-1, TFR, and TF-r.

Effective wound healing requires that multiple factors play their individual roles in a time- and tissue-specific manner. Failure of any element in this process can hamper healing. For example, under normal wound healing settings, HSPs, PDGF, FGF and VEGF are induced within 24 h of skin injury and eventually decline from this elevated level of protein synthesis to a basal level in 7-14 days. However, in chronic wounds, the expression of these proteins is delayed or inhibited. As such, the induction or increased activity of these factors may be beneficial. During the course of wound healing, a variety of HSPs are expressed in a specific temporal and spatial manner. The biological induction of a broad spectrum of HSPs may be a better approach to promoting wound healing than providing just a single HSP. Because wound healing involves several key molecular pathways and cell types, a multi-pronged approach is used to modulate a range of biological molecules and processes to promote an overall increase in wound-healing activity.

The present invention is directed to oligonucleotides, pharmaceutical compositions, polynucleotide vectors, and methods for performing RNA interference (RNAi), miRNA-mediated inhibition, and inhibition of miRNAs. Non-limiting examples of oligonucleotides include short interfering RNAs (siRNAs), small hairpin RNAs (shRNAs), short small hairpin RNAs (sshRNAs), pre-miRNA mimics, miRNA antagonists. In some embodiments, the oligonucleotide is an RNAi agent. Non-limiting examples of RNAi agents include short interfering RNAs (siRNAs), short hairpin RNAs (shRNAs), short small hairpin RNAs (sshRNAs), and RNAi duplexes, such as pre-miRNA mimics.

Oligonucleotides

Disclosed herein are oligonucleotides, both alone and in combination, for use in the treatment of wounds in a subject in need thereof. These oligonucleotides may modify the activity and/or expression of RNAs by various mechanisms of action. Oligonucleotides disclosed herein include RNAi agents, such as short small hairpin RNAs (sshRNAs) and pre-miRNA mimics, as well as RNAi antagonists, such as micro-RNA (miRNA) antagonists.

Short small hairpin RNAs (sshRNAs) differ from traditional shRNAs in that they have a stem sufficiently short, 19 base pairs or less, to disqualify them as a Dicer substrates. Since sshRNAs cannot be processed by Dicer in contrast to ordinary shRNAs, they, therefore, must be processed by a Dicer-independent mechanism. sshRNAs also differ from ordinary shRNAs in that the loop length can be much shorter, which confers stability without loss of activity. sshRNAs are predominantly loaded as intact molecules into Argonaute (Ago)-containing complexes without prior processing by Dicer and are activated by Ago2-mediated cleavage of the passenger arm of the hairpin without prior cleavage of the loop. Advantages of sshRNAs over traditional shRNAs may include, but are not limited to, reduced manufacturing cost, fewer off-target effects of passenger strand, increased stability and resistance to endonucleases, lower immunostimulatory activity, and increased potency. sshRNAs disclosed herein may be chemically synthesized. Chemically synthesized sshRNAs may also be referred to as "synthetic sshRNAs" or "synthetic shRNAs" or "short synthetic shRNAs." sshRNAs that are chemically synthesized can contain modified nucleotides and or backbones in precise modification patterns that enhance efficacy with diminished immune stimulation potential.

While sshRNAs typically inhibit the expression or activity of messenger RNAs and are duplex RNA, miRNA antagonists typically inhibit the expression or activity of endogenous miRNA and are single-stranded.

Pre-miRNA mimics are synthetic miRNA precursors, meaning they have not yet been processed into mature miRNA. Pre-miRNA mimics are hairpin, duplex (double-stranded) RNAs. Pre-miRNA mimics disclosed herein may have a shorter stem and/or a smaller loop region than naturally-occurring miRNA precursors. This may make the pre-miRNA mimics less susceptible to degradation by endonucleases. For instance, generally, naturally-occurring miRNAs and their precursors have a loop region of 4 nucleotides or more. Pre-miRNA mimics disclosed herein may have a loop region of 2 nucleotides or fewer. Pre-miRNA mimics disclosed herein may have a loop region consisting of 2 nucleotides or 1 nucleotide. Pre-miRNA mimics disclosed herein may have a loop region consisting of 2 nucleotides or 1 nucleotide. Pre-miRNA mimics disclosed herein may have a loop region consisting of a direct connection. Pre-miRNA mimics disclosed herein may have a loop region with a length of 2 nucleotides, 1 nucleotide, or zero nucleotides. Pre-miRNA mimics disclosed herein may have a single stem, wherein the stem is 19 bp in length or less. Pre-miRNA mimics disclosed herein may have a single stem, wherein the stem is 10 bp to 19 bp in length. Pre-miRNA mimics disclosed herein may comprise an overhang region on either the end of the sense strand or end of the antisense strand that is not adjacent to the loop region. Pre-miRNA mimics disclosed herein may comprise only a single overhang region.

It has been found that introducing pre-miRNA mimics to cells, rather than the mature miRNAs, is more efficient for boosting the RNAi activity of endogenous miRNA. Thus, the oligonucleotides disclosed herein provide means to both inhibit (via sshRNAs and pre-miRNA mimics) and boost (via miRNA antagonists) messenger RNA expression and activity.

While the oligonucleotides disclosed herein mainly comprise RNA, these oligonucleotides may also comprise some modified ribonucleotides or substitutions for ribonucleotides, such that other nucleic acids are incorporated as well. These modified ribonucleotides may also be referred to as ribonucleotides with chemical modifications. Modified ribonucleotides include deoxyribonucleic acids (DNA), locked nucleic acids (LNA), and peptide nucleic acids (PNA), non-nucleic acids, or any combination thereof.

Although the oligonucleotides disclosed herein may comprise modifications, substitutions, non-nucleotides, nucleotide moieties, conjugate moieties, etc., the majority of the nucleotides or nucleotide moieties in the oligonucleotides disclosed herein may be unmodified ribonucleotides. In some embodiments, at least 30% of the oligonucleotide consists of unmodified ribonucleotides. In some embodiments, at least 35% of the oligonucleotide consists of unmodified ribonucleotides. In some embodiments, at least 40% of the oligonucleotide consists of unmodified ribonucleotides. In some embodiments, at least 45% of the oligonucleotide consists of unmodified ribonucleotides. In some embodiments, at least 50% of the oligonucleotide consists of unmodified ribonucleotides. In some embodiments, at least 51% of the oligonucleotide consists of unmodified ribonucleotides. In some embodiments, at least 55% of the oligonucleotide consists of unmodified ribonucleotides. In some embodiments, at least 60% of the oligonucleotide consists of unmodified ribonucleotides. In some embodiments, at least 65% of the oligonucleotide consists of unmodified ribonucleotides. In some embodiments, at least 70% of the oligonucleotide consists of unmodified ribonucleotides. In some embodiments, at least 75% of the oligonucleotide consists of unmodified ribonucleotides.

In some embodiments, the oligonucleotide is at least 55% RNA. In some embodiments, the oligonucleotide is at least 60% RNA. In some embodiments, the oligonucleotide is at least 70% RNA. In some embodiments, the oligonucleotide is at least 80% RNA. In some embodiments, the oligonucleotide is at least 90% RNA. In some embodiments, the oligonucleotide is at least 95% RNA.

shRNAs, sshRNAs, and pre-miRNA mimics are unimolecular nucleic acid-containing polynucleotides comprising a sense sequence, a loop region, and an antisense sequence, with the sense and antisense sequences being at least partially complementary. In some embodiments, the sense and antisense sequences can be about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% complementary.

In some embodiments, the sense and antisense sequences are from at least about 60% to at least about 95% complementary, from at least about 65% to at least about 95% complementary, from at least about 70% to at least about 95% complementary, from at least about 75% to at least about 95% complementary, from at least about 80% to at least about 95% complementary.

In some embodiments, the antisense sequence or the sense sequence each independently have a length of about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, or about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, or about 50 nucleotides.

In some embodiments, the antisense sequence or sense sequence can be from about 10 nucleotides to about 11 nucleotides, from about 11 nucleotides to about 12 nucleotides, from about 12 nucleotides to about 13 nucleotides, from about 13 nucleotides to about 14 nucleotides, from about 14 nucleotides to about 15 nucleotides, from about 15 nucleotides to about 16 nucleotides, from about 16 nucleotides to about 17 nucleotides, from about 17 nucleotides to about 18 nucleotides, from about 18 nucleotides to about 19 nucleotides, from about 19 nucleotides to about 20 nucleotides, from about 20 nucleotides to about 21 nucleotides, from about 21 nucleotides to about 22 nucleotides, from about 22 nucleotides to about 23 nucleotides, from about 23 nucleotides to about 24 nucleotides, from about 24 nucleotides to about 25 nucleotides, from about 25 nucleotides to about 26 nucleotides, from about 26 nucleotides to about 27 nucleotides, from about 27 nucleotides to about 28 nucleotides, from about 28 nucleotides to about 29 nucleotides, from about 29 nucleotides to about 30 nucleotides.

In some embodiments, the shRNA, sshRNA, or pre-miRNA mimic has a loop region that directly connects the sense and antisense sequences. The loop region that directly connects the sense and antisense sequences may also be referred to as a loop having zero nucleotides. In some embodiments, the shRNA, sshRNA, or pre-miRNA mimic has a loop region comprising zero nucleotides. In some embodiments, the loop region has a length of 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, or 24 nucleotides.

In some embodiments, a small loop region confers resistance to degradation by endonucleases. The small loop region may have a length of about zero nucleotides, about 1 nucleotide or about 2 nucleotides. In some embodiments, the sshRNAs consist of a sense strand, a loop region, an antisense strand, and optionally one or more conjugate moieties, wherein the sense strand has a length of 10-19 nucleotides, the loop region has a length of 2 nucleotides or less, and the antisense strand has a length of 10-19 nucleotides. In some embodiments, the sshRNAs consist of a sense strand, a loop region, an antisense strand, and optionally one or more conjugate moieties, wherein the sense strand has a length of 10-19 nucleotides, the loop region has a length of less than 2 nucleotides, and the antisense strand has a length of 10-19 nucleotides.

In some embodiments, the loop region can comprise non-nucleotide moieties. The loop region may comprise non-nucleotide moieties from about 1 non-nucleotide moiety to about 2 non-nucleotide moieties, from about 2 non-nucleotide moieties to about 3 non-nucleotide moieties, from about 3 non-nucleotide moieties to about 4 non-nucleotide moieties, from about 4 non-nucleotide moieties to about 5 non-nucleotide moieties, from about 5 non-nucleotide moieties to about 6 non-nucleotide moieties, from about 6 non-nucleotide moieties to about 7 non-nucleotide moieties, from about 7 non-nucleotide moieties to about 8 non-nucleotide moieties, from about 8 non-nucleotide moieties to about 9 non-nucleotide moieties, from about 9 non-nucleotide moieties to about 10 non-nucleotide moieties, from about 10 non-nucleotide moieties to about 11 non-nucleotide moieties, from about 11 non-nucleotide moieties to about 12 non-nucleotide moieties, from about 12 non-nucleotide moieties to about 13 non-nucleotide moieties, from about 13 non-nucleotide moieties to about 14 non-nucleotide moieties, from about 14 non-nucleotide moieties to about 15 non-nucleotide moieties, from about 15 non-nucleotide moieties to about 16 non-nucleotide moieties, from about 16 non-nucleotide moieties to about 17 non-nucleotide moieties, from about 17 non-nucleotide moieties to about 18 non-nucleotide moieties, from about 18 non-nucleotide moieties to about 19 non-nucleotide moieties, from about 19 non-nucleotide moieties to about 20 non-nucleotide moieties, from about 20 non-nucleotide moieties to about 21 non-nucleotide moieties, from about 21 non-nucleotide moieties to about 22 non-nucleotide moieties, from about 22 non-nucleotide moieties to about 23 non-nucleotide moieties, or from about 23 non-nucleotide moieties to about 24 non-nucleotide moieties.

In some embodiments, the shRNA, sshRNA, or pre-miRNA mimic has a loop region consisting of: 1 nucleotide or non-nucleotide moiety; 2 nucleotides, non-nucleotide moieties, or a combination thereof; 3 nucleotides, non-nucleotide moieties, or a combination thereof; 4 nucleotides, non-nucleotide moieties, or a combination thereof; 5 nucleotides, non-nucleotide moieties, or a combination thereof; 6 nucleotides, non-nucleotide moieties, or a combination thereof; 7 nucleotides, non-nucleotide moieties, or a combination thereof; 8 nucleotides, non-nucleotide moieties, or a combination thereof; 9 nucleotides, non-nucleotide moieties, or a combination thereof; 10 nucleotides, non-nucleotide moieties, or a combination thereof; 11 nucleotides, non-nucleotide moieties, or a combination thereof; 12 nucleotides, non-nucleotide moieties, or a combination thereof; 13 nucleotides, non-nucleotide moieties, or a combination thereof; 14 nucleotides, non-nucleotide moieties, or a combination thereof; 15 nucleotides, non-nucleotide moieties, or a combination thereof; 16 nucleotides, non-nucleotide moieties, or a combination thereof; 17 nucleotides, non-nucleotide moieties, or a combination thereof; 18 nucleotides, non-nucleotide moieties, or a combination thereof; 19 nucleotides, non-nucleotide moieties, or a combination thereof; 20 nucleotides, non-nucleotide moieties, or a combination thereof 21 nucleotides, non-nucleotide moieties, or a combination thereof; 22 nucleotides, non-nucleotide moieties, or a combination thereof; 23 nucleotides, non-nucleotide moieties, or a combination thereof; or 24 nucleotides, non-nucleotide moieties, or a combination thereof. As used herein, the terms nucleotide and non-nucleotide moiety, may be used interchangeably, unless otherwise noted.

In some embodiments, the sequence of the loop region can include nucleotide residues unrelated to the target. In some embodiments, the nucleotides of the loop are chosen from: rA, dA, rC, dC, rG, dG, rU, dU, rT, and dT, wherein r is a nucleotide comprising a ribose sugar; d is a nucleotide comprising a deoxyribose sugar; A is a nucleotide comprising an adenine base; C is a nucleotide comprising a cytosine base; G is a nucleotide comprising a guanosine base; U is a nucleotide comprising a uracil base; and T is a nucleotide comprising a thymine base. In some embodiments, the loop sequence is chosen from: 5'-rUrU-3', 5'-rTrU-3', 5'-rUrT-3', 5'-dUdU-3', 5'-dTdU-3 5'-dUdT-3', 5'-rTrT-3', and 5'-dTdT-3'.

In some embodiments, the loop region comprises a deoxyribonucleotide, a phosphorothioate internucleotide linkage, a 2'-O-alkyl modification, a non-nucleotide monomer or a reversible linkage, or combinations thereof. In some embodiments, the reversible linkage is a disulfide bond. In some embodiments, the 2'-O-alkyl modification is a 2'-O-methyl modification.

An antisense sequence of the oligonucleotides disclosed herein can be substantially complementary to a messenger RNA (mRNA), an RNA that is not an mRNA, or a sequence of DNA that is either coding or non-coding. Non-limiting examples of mRNAs include 5'-methylguanosine capped, 3'-polyadenylated mRNAs; 5'-methylguanosine capped, de-adenylated mRNAs; de-capped, 3'-polyadenylated mRNAs; de-capped, de-adenylated mRNAs; P-body associated mRNAs; stress granule associated mRNAs; cytosolic mRNAs; and endoplasmic reticulum associated mRNAs. Non-limiting examples of non-mRNA RNAs include transfer RNAs (tRNAs), ribosomal RNAs (rRNAs), heteronuclear RNAs (hnRNAs), Piwi-inducible RNAs (piRNAs), negative strand viral RNA, and positive stranded viral RNA.

An RNAi agent is specific for a target transcript when the antisense sequence is substantially complementary to the target transcript. Substantially complementary can be from about 80% to about 85% complementary, from about 85% to about 90% complementary, from about 90% to about 95% complementary, from about 95% to about 96% complementary, from about 96% to about 97% complementary, from about 97% to about 98% complementary, from about 98% to about 99% complementary, or from about 99% to 100% complementary.

The sense sequence of the pre-miRNA mimic can comprise a sequence with identity from 5' to 3' to a naturally occurring miRNA. The sense sequence can comprise a sequence with about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or 100% identity to a naturally occurring miRNA. The sense sequence can comprise sequence from about 60% to about 99%, from about 65% to about 99%, from about 70% to about 99%, from about 75% to about 99%, from about 80% to about 99%, from about 85% to about 99%, from about 90% to about 99% identity from 5' to 3' to a naturally occurring miRNA.

The antisense strand of the pre-miRNA mimic has complementarity from 5' to 3' to the sense strand of the pre-miRNA mimic. The antisense strand can have about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or 100% complementarity from 5' to 3' to the sense strand of the pre-miRNA mimic. The antisense strand can have from about 60% to about 65%, from about 65% to about 70%, from about 70% to about 75%, from about 75% to about 80%, from about 80% to about 81%, from about 81% to about 82%, from about 82% to about 83%, from about 83% to about 84%, from about 84% to about 85%, from about 85% to about 86%, from about 86% to about 87%, from about 87% to about 88%, from about 88% to about 89%, from about 89% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, or from about 98% to about 100% complementarity from 5' to 3' to the sense strand of the pre-miRNA mimic.

In some embodiments, the siRNA, shRNA, sshRNA, or pre-miRNA mimic has no overhang or an overhang region of about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, about 11 nucleotides, or about 12 nucleotides on the 5' end or the 3' end. In some embodiments, the siRNA, shRNA, sshRNA, or pre-miRNA mimic can have an overhang region from about 1 nucleotide to about 2 nucleotides, from about 2 nucleotides to about 3 nucleotides, from about 3 nucleotides to about 4 nucleotides, from about 4 nucleotides to about 5 nucleotides, from about 5 nucleotides to about 6 nucleotides, from about 6 nucleotides to about 7 nucleotides, from about 7 nucleotides to about 8 nucleotides, from about 8 nucleotides to about 9 nucleotides, from about 9 nucleotides to about 10 nucleotides, from about 10 nucleotides to about 11 nucleotides, or from about 11 nucleotides to about 12 nucleotides on the 5' end or the 3' end. Nucleotides of the overhang region can be unmodified, or can contain one or more modifications. Non-limiting examples of overhang modifications include modifications of the 2' position of a sugar, such as halogen or O-alkyl substitution, cholesterol or alpha-tocopherol, and modifications of a phosphate group such as phosphorothioate modification. A nucleotide of the overhang region can be a ribonucleic acid, a deoxyribonucleic acid, or any combination thereof.

In some embodiments, the shRNA, sshRNA, or pre-miRNA mimic comprises RNAs with base-pair mismatches or bulges. The sense sequence may be identical to the target transcript or, through mismatches, insertions, or deletions, have differences at about 1 nucleotide, about 2 nucleotides, about 3 nucleotides, about 4 nucleotides, or about 5 nucleotides from a target transcript.

A miRNA antagonist is a unimolecular nucleic acid-containing polynucleotide comprising a sequence complementary to a mature miRNA. The miRNA antagonist can include RNA, DNA, LNA, PNA, one or more 2'-O-methyl modifications, phosphorothioate internucleotide linkage(s), ZEN modification(s), and non-nucleic acids, and any combination thereof. Non-limiting examples of miRNA antagonists include antagomiRs, all-DNA anti-miRs, all-RNA anti-miRs, and LNA anti-miRs. In some embodiments, the miRNA antagonist can have a length of about 7 nucleotides, about 8 nucleotides, about 9 nucleotides, about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, or about 50 nucleotides.

In some embodiments, the miRNA antagonist comprises a sequence about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% complementary to a mature miRNA.

In some embodiments, the miRNA antagonist comprises a sequence from about 60% to about 100%, from about 65% to about 100%, from about 70% to about 100%, from about 75% to about 100%, from about 80% to about 100%, from about 85% to about 100%, or from about 90% to about 100%, complementary to a mature miRNA.

The target of an RNAi agent disclosed herein may be an RNA transcript encoding prolyl hydroxylase domain-containing protein 2 (PHD2). PHD2, by way of non-limiting example, may be human PHD2, mouse PHD2, simian PHD2, bovine PHD2, canine PHD2, or PHD2 expressed in any animal in need of a wound healing treatment. The target of an RNAi agent disclosed herein may be an RNA transcript encoded by an EGLN1 homolog. The EGLN1 homolog may be at least about 70%, at least about 75%, at least about 80%, at least about 85%, or at least about 90% homologous to SEQ ID NO. 1 or SEQ ID NO. 2. The terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application. In some embodiments, EGLN1 is chosen from human EGLN1 (SEQ ID NO. 1) and mouse EGLN1 (SEQ ID NO. 2). In some embodiments, an RNAi agent is designed to target a transcript of both human EGLN1 (SEQ ID NO. 1) and mouse EGLN1 (SEQ ID NO. 2). In some embodiments, an sshRNA is designed to target a transcript of human EGLN1 (SEQ ID NO. 1). In some embodiments, an sshRNA is designed to target a transcript of mouse EGLN1 (SEQ ID NO. 2). In some embodiments, an sshRNA is designed to target transcripts of both human EGLN1 (SEQ ID NO. 1) and mouse EGLN1 (SEQ ID NO. 2).

An RNAi agent targeting PHD2 can reduce the amount of PHD2 transcript about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9%.

An RNAi agent targeting PHD2 can reduce the amount of PHD2 transcript from about 10% to about 99.9%, from about 10% to about 99%, from about 20% to about 99%, from about 30% to about 99%, from about 40% to about 99%, from about 50% to about 99%, from about 55% to about 99%, from about 60% to about 99%, from about 65% to about 99%, from about 70% to about 99%, from about 75% to about 99%, from about 80% to about 99%.

In some embodiments, RNAi-mediated depletion of PHD2 can increase the amount of HIF-1α protein and/or HIF-1α target gene expression. Non-limiting examples of HIF-1α target genes include VEGF, HSP90, and HSP70. An RNAi agent targeting PHD2 can increase the amount of HIF-1α protein and/or HIF-1α target gene expression about 1%, about 5%, about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1,000%, about 2,000%, about 3,000%, about 4,000%, about 5,000%, about 6,000%, about 7,000%, about 8,000%, about 9,000%, or about 10,000%.

An RNAi agent targeting PHD2 may increase the amount of HIF-1α protein and/or HIF-1α target gene expression from about 10% to about 10,000%, from about 20% to about 10,000%, from about 30% to about 10,000%, from about 40% to about 10,000%, from about 50% to about 10,000%, or from about 100% to about 10,000%.

Disclosed herein are miRNA antagonists and pre-miRNA mimics designed to antagonize and mimic naturally occurring miRNAs, respectively. In some embodiments, the pre-miRNA mimics are used to "boost" the expression of a mature miRNA. In some embodiments, a naturally occurring miRNA or a mature miRNA can be chosen from miR-210 (SEQ ID NO. 3) and miR-21 (SEQ ID NO. 4). In some embodiments, the naturally occurring miRNA or mature miRNA is miR-210 (SEQ ID NO. 3). In some embodiments, the naturally occurring miRNA or mature miRNA is miR-21 (SEQ ID NO. 4).

A pre-miRNA mimic, also referred to herein as an pre-miRNA mimic, may increase a steady-state level of a mature miRNA about 1%, about 5%, about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000%.

A pre-miRNA mimic may increase a steady-state level of a mature miRNA from about 1% to about 5%, from about 5% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, from about 90% to about 100%, from about 100% to about 200%, from about 200% to about 300%, from about 300% to about 400%, from about 400% to about 500%, from about 500% to about 600%, from about 600% to about 700%, from about 700% to about 800%, from about 800% to about 900%, from about 900% to about 1000%, from about 1000% to about 2000%, from about 2000% to about 3000%, from about 3000% to about 4000%, from about 4000% to about 5000%, from about 5000% to about 6000%, from about 6000% to about 7000%, from about 7000% to about 8000%, from about 8000% to about 9000%, or from about 9000% to about 10000%.

A miRNA antagonist can reduce the amount or the activity of a miRNA about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9%.

A miRNA antagonist can reduce the amount or the activity of a miRNA from about 1% to about 5%, from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, from about 98% to about 99%, from about 99% to about 99.5%, or from about 99.5% to about 99.9%.

Disclosed herein are oligonucleotide comprising modifications. Modifications may comprise chemical modifications to the bases or backbone of the oligonucleotides disclosed herein. Modifications to oligonucleotides may improve activities of the oligonucleotide in a cell, in vitro, in vivo, or in a subject. Non-limiting examples of activities include increased activity, increased half-life, increased cellular uptake, increased targeting to a cellular compartment, reduced off-target suppression of transcripts, and modified immunostimulatory activity. Non-limiting examples of increased activity include increased RNAi activity, increased miRNA-mediated repressive activity, and increased miRNA inhibitory activity. Activities may include increased stability in a biological fluid. Non-limiting examples of a biological fluid include plasma, serum, saliva, sputum, stool, breast milk, mucus, sweat, tears, urine, semen, vaginal secretion, pancreatic juice, bile, pus, and joint fluid. Characteristics may include modified immunostimulatory activity. Non-limiting examples of immunostimulatory activity include expression of interferon-β(IFN-β), interleukin-6 (IL-6) secretion, tumor necrosis factor-α (TNF-α) secretion.

An increase in activities may be about 1%, about 5%, about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000%.

A reduction in activities may be about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9%.

In some embodiments, modifications to oligonucleotide reduce off-target effects of the oligonucleotide. In some embodiments, modifications to oligonucleotide reduce off-target effects of the oligonucleotide by about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000%.

In some embodiments, modifications to oligonucleotides may cause an increase in RNAi activity, miRNA-mediated repressive activity, miRNA inhibitory activity, molecular half-life, stability in a biological fluid, cellular uptake, or targeting to a cellular compartment. The increase in RNAi activity, miRNA-mediated repressive activity, miRNA inhibitory activity, molecular half-life, stability in a biological fluid, cellular uptake, or targeting to a cellular compartment may be about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000%.

Non-limiting examples of modifications include modified nucleotides, modified internucleotide linkages, non-nucleotides, deoxynucleotides, constrained backbone modifications and nucleotide analogs. Nucleotide modifications can include modifications to the base of the nucleotide, to the sugar of the nucleotide, or to the phosphate group of the nucleotide. Any nucleotide within a sshRNA, miRNA antagonist or pre-miRNA mimic can be modified. In some embodiments, the modifications are only to the sense sequence, only to the antisense sequence, or only to the loop region. In some embodiments, the modifications are in the sense sequence, antisense sequence, loop region, or a combination thereof.

In some embodiments, the oligonucleotide comprises a conjugate moiety. In some embodiments, the conjugate moiety can be a detectable label, such as a radioactive label, fluorescent label, mass label, transferrin, and cholesteryl. In some embodiments, a small RNA can be targeted to certain organs by conjugating specific moieties, for example, mannose residues to target to the liver.

In some embodiments, the conjugate moiety can enhance delivery, detection, function, specificity, or stability of a molecule of the present invention. Non-limiting examples of said conjugate moieties include amino acids, peptides, proteins, sugars, carbohydrates, lipids, polymers, nucleotides, and polynucleotides, or any combination thereof. In some embodiments, the conjugate moiety can be linked to the sense or antisense sequence or loop region of a shRNA, sshRNA, or pre-miRNA mimic. In some embodiments, the conjugate moiety can be linked at the 5' or 3' end of the sense or antisense sequence of a shRNA, sshRNA, or pre-miRNA mimic.

In some embodiments, a conjugate moiety or a modification of the oligonucleotide comprises an alkyl group. The alkyl group may be saturated, unsaturated, substituted, or unsubstituted. In some embodiments, the alkyl group comprises hydrocarbon chains that are linear, branched, alkanyl, alkenyl, alkynyl, cyclic, heterocyclic, aryl, or heteroaryl, any of which is substituted or unsubstituted. In some embodiments, the alkyl group comprises a functional group chosen from: ether, ester, amide, amine, carbonyl, ketone, acetic anhydride, carbamate, thioether, carbonate, sulfone, halide, thiol, alcohol, thioester, phosphothiorate, phosphate, azo, keto, aldehyde, carboxyl, nitro, nitroso, nitrile, imidazole, morpholino, pyrrolidino, hydrazino, hydroxylamino, isocyanate, cyanate, sulfoxide, sulfide, disulfide, cycloalkyl, cycloalkenyl, cycloalkynyl, cycloheteroalkyl, cycloheteroalkenyl, cycloheteroalkynyl, aryl, and heteroaryl, any of which is substituted or unsubstituted. Non-limiting examples of alkyl groups include substituted and unsubstituted groups of 1 carbon atom, about 2 carbon atoms, about 3 carbon atoms, about 4 carbon atoms, about 5 carbon atoms, about 6 carbon atoms, about 7 carbon atoms, about 8 carbon atoms, about 9 carbon atoms, about 10 carbon atoms, 11 carbon atoms, about 12 carbon atoms, about 13 carbon atoms, about 14 carbon atoms, about 15 carbon atoms, 16 carbon atoms, about 17 carbon atoms, about 18 carbon atoms, about 19 carbon atoms, about 20 carbon atoms, 21 carbon atoms, about 22 carbon atoms, about 23 carbon atoms, about 24 carbon atoms, about 25 carbon atoms, 26 carbon atoms, about 27 carbon atoms, about 28 carbon atoms, about 29 carbon atoms, and about 30 carbon atoms.

A nucleotide of the present invention may comprise a ribonucleotide, a deoxyribonucleotide, or a modification or analog thereof. Non-limiting examples of nucleotides include adenine (A), hypoxanthine (Hy), xanthine (Xt), guanine (G), inosine (I), cytosine (C), uracil (U), thymine (T), SSICS, NaM, queuosine (Q), purines, pyrimidines, and derivatives, analogs, or modifications thereof. Nucleotide analogs comprise nucleotides having modifications in the chemical structure of the base, sugar or phosphate.

In some embodiments, the nucleotide modification is a modification to the base of the nucleotide. Modified bases refer to nucleotide bases such as, adenine, guanine, cytosine, thymine, and uracil, xanthine, inosine, and queuosine that have been modified by the replacement or addition of one or more atoms or groups. Non-limiting examples of nucleotide base modifications include 5-position pyrimidine modifications, 8-position purine modifications, modifications at cytosine exocyclic amines, and substitution of 5-bromo-uracil. Non-limiting examples of types of modifications include alkylated, halogenated, thiolated, aminated, amidated, and acetylated bases, or any combination thereof. Non-limiting examples of modified bases include, 5-propynyluridine, 5-propynylcytidine, 6-methyladenine, 6-methylguanine, N,N-dimethyladenine, 2-propyladenine, 2-propylguanine, 2'-aminoadenine, 1-methylinosine, 3-methyluridine, 5-methylcytidine, 5-methyluridine, 5-methylthymine, 5-hydroxycytidine, 5-formylcytidine, 5-(2-amino)propyluridine, 5-halocytidine, 5-halouridine, 4-acetyl cytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, archaeosine, naphthyl- and substituted naphthyl-conjugated bases, N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

In some embodiments, a modification to a nucleotide is a modification of the sugar or replacement of the sugar with a non-ribosyl sugar analog. Non-limiting examples of replacement sugars include mannoses, arabinoses, glucopyranoses, galactopyranoses, and 4-thioribose. Modifications to the sugar can occur at the 1' position, 2' position, 3' position, 4' position, 5' position, or any combination thereof. In some embodiments, the modification of the sugar is at the 2' position of the sugar. Non-limiting examples of 2' sugar modifications include replacing the 2'-OH with H, OR, R, F, Cl, Br, I, SH, SR, NH2, NHR, NR2, or CN, wherein R is an alkyl group. In some embodiments, the 2' sugar modification is chosen from: 2'-O-methyl, 2'-O-ethyl, 2'-O-propyl, 2'-O-isopropyl, 2'-O-butyl, 2'-O-isobutyl, 2'-O-ethyl-O-methyl (—OCH2CH2OCH3), and 2'-O-ethyl-OH (—OCH2CH2OH). In some embodiments, the 2' sugar modification is a methyl group. The 2' oxygen modification can occur on a nucleotide of the sense sequence, the antisense sequence, or the loop region.

In some embodiments, a nucleotide modification can be a modification of the phosphate group. Non-limiting examples of phosphate group modifications include methylphosphonates, phosphorothioates, phosphordithioates, and peptides.

In some embodiments, a nucleotide modification is a 3' cap structure, such as an inverted deoxythymidine.

In some embodiments, a modification is a non-nucleotide modifier such as N,N-diethyl-4-(4-nitronaphthalen-1-ylazo)-phenylamine (ZEN) or a C3 spacer (propanediol). ZEN modification can either be placed at an internal position between two nucleotides or at a terminus.

An oligonucleotide disclosed herein may have no modifications or can have modifications of about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, about 51 nucleotides, about 52 nucleotides, about 53 nucleotides, about 54 nucleotides, about 55 nucleotides, about 56 nucleotides, about 57 nucleotides, about 58 nucleotides, about 59 nucleotides, about 60 nucleotides, about 61 nucleotides, about 62 nucleotides, about 63 nucleotides, about 64 nucleotides, about 65 nucleotides, about 66 nucleotides, about 67 nucleotides, about 68 nucleotides, about 69 nucleotides, about 70 nucleotides, about 71 nucleotides, about 72 nucleotides, about 73 nucleotides, about 74 nucleotides, about 75 nucleotides, or about 76 nucleotides.

In some embodiments, the oligonucleotide comprises a plurality of modifications. The plurality of modifications may occur only on consecutive nucleotides. The plurality of modifications may occur only on alternating nucleotides. The plurality of modifications may occur on both consecutive nucleotides and alternating nucleotides. Alternating nucleotides, as used herein, refers to two nucleotides separated only by a third nucleotide.

A sense or antisense strand of an oligo nucleotide disclosed herein may have no modifications or can have modifications of about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, or about 50 nucleotides.

In some embodiments, the oligonucleotides disclosed herein have modifications at particular positions of the molecule. In some embodiments, the molecule has a modification at every position of the oligonucleotide. In some embodiments, the particular modified positions comprise positions 1, 2, 3, 4, 5, 6, 7, 8, 9, 10, 11, 12, 13, 14, 15, 16, 17, 18, 19, 20, 21, or 22 of the oligonucleotide as viewed from 5' to 3', or any combination thereof. In some embodiments, the particular modified positions comprise positions 2, 4, 6, 8, 10, 12, 13, 14, 16, 18, 20, or 22 of the oligonucleotide as viewed from 5' to 3', or any combination thereof. In some embodiments, the modification at a particular position is a sugar modification. Non-limiting examples of sugar modifications at particular positions include 2'-O-methyl modifications, LNA modifications, DNA modifications, and 2'-F modifications. In some embodiments, the sugar modification is at every position in the oligonucleotide. In some embodiments, the sugar modifications are at positions 1, 3, 4, 6, 7, 9, 10, 12, 13, and 15 of the oligonucleotide. In some embodiments, the modification at a particular position is a phosphorothioate internucleotide linkage. In some embodiments, the phosphorothioate linkages are at every position in the oligonucleotide. In some embodiments, the phosphorothioate linkages are at three consecutive positions at both the 5' and 3' end in the oligonucleotide. In some embodiments, the modification at a particular position is a ZEN modification. In some embodiments, the ZEN modification is between position 1 and 2 and also at the 3'-end of the oligonucleotide. In some embodiments, the small RNA to be modified at particular positions is a miRNA antagonist. In some embodiments, the miRNA antagonist is a miR-210 antagonist. In some embodiments, the miR-210 antagonist has 2'-O-methyl modifications. In some embodiments, the miR-210 antagonist has 2'-O-methyl modifications at every position. In some embodiments, the miR-210 antagonist has 2'-O-methyl modifications at positions 2, 4, 6, 8, 10, 12, 13, 14, 16, 18, 20, and 22. In some embodiments, the miR-210 antagonist has 2'-O-methyl modifications at positions 1, 3, 4, 6, 7, 9, 10, 12, 13, and 15. In some embodiments, the miR-210 antagonist has phosphorothioate internucleotide linkage(s). In some embodiments, the miR-210 antagonist has phosphorothioate linkages are at every position in the oligonucleotide. In some embodiments, the miR-210 antagonist has phosphorothioate linkages are at three consecutive positions at both the 5' and 3' end in the oligonucleotide. In some embodiments, the modification at a particular position is a ZEN modification. In some embodiments, the miR-210 antagonist has ZEN modification. In some embodiments, the miR-210 antagonist has ZEN modification between position 1 and 2 and also at the 3'-end of the oligonucleotide. In some embodiments, the miR-210 antagonist has 2'-O-methyl modifications at positions 12, 13, and 14, and LNA modifications at positions 2, 4, 6, 8, 10, 16, 18, 20, and 22. In some embodiments, the miR-210 antagonist has 2'-O-methyl modifications at positions 12, 13, and 14, and 2'-F modifications at positions 2, 4, 6, 8, 10, 16, 18, 20, and 22. In some embodiments, the miR-210 antagonist has 2'-O-methyl modifications at positions 12, 13, and 14; 2'-F modifications at positions 4, 8, 18, and 22; and LNA modifications at positions 2, 6, 10, 16, and 20. In some embodiments, the miR-210 antagonist has 2'-O-methyl modifications at positions 2, 6, 10, 12, 13, 14, 16, and 20, and 2'-F modifications at positions 4, 8, 18, and 22. In some embodiments, the miRNA antagonist has 2'-O-methyl modifications at every position and 3 phosphorothioate linkages at consecutive residues at both the 5'- and 3'-end, (e.g., SG606, SEQ ID No. 326). In some embodiments, the miRNA antagonist is 15 nucleotides and has phosphorothioate linkages at every position and 2'-O-methyl modifications at positions 1, 3, 4, 6, 7, 9, 10, 12, 13, and 15 and LNA modifications at positions 2, 5, 8, 11, and 14 (e.g., SG607, SEQ ID No. 327). In some embodiments, the miRNA antagonist has 2'-O-methyl modifications at every position and ZEN modifications between position 1 and 2 and also at the 3'-end. In some cases this antagonist is 1 nucleotide shorter than full-length complementarity to the mature miRNA sequence (e.g., SG615, SEQ ID No. 328).

In some embodiments, a pre-miRNA mimic has a nucleotide at its 5' end of the antisense strand in which the phosphate or hydroxyl group has been replaced with a replacement group. Non-limiting examples of replacement groups include biotin, alkyl groups, amine groups, lower alkylamine groups, acetyl groups, 2'-O-alkyls, DMTO (4,4'-dimethoxytrityl with oxygen), fluoresceins, TexasReds, thiols, and acridines.

Methods of Treatment

Disclosed herein, are methods for treating a wound in a subject in need thereof comprising administering a therapeutically effective amount an oligonucleotide disclosed herein. The oligonucleotide may be selected from a sshRNA, a miRNA antagonist, and a pre-miRNA mimic. The method may comprise administering a therapeutically effective amount of a sshRNA and a therapeutically effective amount of a miRNA antagonist. The method may comprise administering a therapeutically effective amount of a sshRNA and a therapeutically effective amount of a pre-miRNA mimic. The method may comprise administering a therapeutically effective amount of a pre-miRNA mimic and a therapeutically effective amount of a miRNA antagonist. The method may comprise administering a therapeutically effective amount of a sshRNA, a therapeutically effective amount of a pre-miRNA mimic, and a therapeutically effective amount of a miRNA antagonist.

While the oligonucleotides disclosed herein may be used to modify gene expression relevant to many biological pathways and conditions, the experimental examples disclosed herein demonstrate the usefulness of these oligonucleotides in wound healing. Wound healing is a complex and dynamic biological process with three overlapping phases: an inflammatory phase, a proliferative phase, and a remodeling phase. The oligonucleotides, compositions and methods disclosed herein especially benefit the inflammatory and proliferative phases by accelerating the initial healing process.

Oligonucleotides and their formulations may be more stable molecules for wound healing purposes compared to small molecule inhibitors, recombinant growth factors and other proteins, facilitating their use in the clinic as well as in resource-limited environments. Because of the long-lasting pharmacological effects of the oligonucleotide inhibitors disclosed herein, the effect of a single application of oligonucleotide inhibitors may be expected to last from one dressing change to the next.

The methods disclosed herein may comprise treating a chronic wound. The chronic wound may be a wound that has existed for more than 24 hours, more than 3 days, more than a week, more than two weeks, more than a month, more than two months, more than six months, or more than a year.

The methods disclosed herein may comprise treating a non-healing wound. The non-healing wound may be a wound that still exists after one or more treatments or therapies have been applied to the wound, and has not healed in an expected time frame.

The methods may comprise administering a combination of a sshRNA, a miRNA antagonist, and a pre-miRNA mimic, wherein the amount of any one of the sshRNA, a miRNA antagonist, and a pre-miRNA mimic is administered in an amount that would be less than therapeutically effective if administered alone. The method may comprise administering a combination of a sshRNA, a miRNA antagonist, and a pre-miRNA mimic, wherein at least one of the sshRNA, a miRNA antagonist, and a pre-miRNA mimic is administered at a dose that would be subtherapeutic when administered alone. The combination of two or more of the oligonucleotides disclosed herein may have an additive therapeutic effect or a synergistic therapeutic effect.

Disclosed herein are methods of treating a wound in a subject comprising administering an sshRNA inhibiting PHD2, a pre-miRNA mimic enhancing activity of miR-21, and an miRNA antagonist inhibiting miR-210. The methods may promote wound healing by stimulating the production of growth factors and angiogenic effectors, including HSPs, VEGF, PDGF, EPO, ANG 1/2, and PLGF, and the proliferation of fibroblasts and keratinocytes. HSPs, VEGF, PDGF, EPO, ANG 1/2, and PLGF may promote wound healing, especially the initial inflammatory and proliferation phases.

The reason for inhibiting PHD2 using an sshRNA is to promote HIF-1α activity, which is compromised in impaired wound healing. Under normoxia, PHD2 (prolyl hydroxylase domain-containing protein 2) hydroxylates prolines on HIF-1α, which triggers its degradation via the ubiquitin-proteasome pathway. Thus, the inhibition of PHD2 provides an effective approach to stabilize levels of HIF-1α under normoxia. The stabilization of HIF-1α in this fashion may induce the expression of factors like EPO, HSF-1, PDGF, and angiopoietins whose activities promote the angiogenesis and vascular remodeling that are essential for wound healing. HIF-1α may also induce the recruitment of macrophages and endothelial progenitors from bone marrow to wounded sites to promote vasculogenesis and microbial resistance. In addition, it may promote the enhanced expression of heat-shock proteins (HSPs) by directly up-regulating HSF-1, the transcription factor that induces the synthesis of other HSPs. Reduced levels of HSPs are found in chronic human wounds as well as in animal models of impaired wound healing, suggesting their active role in wound healing.

miR-210 is one of the miRNAs that is highly up-regulated by HIF-1α. Increased levels of miR-210 result in reduced keratinocyte proliferation and mobility, which are essential activities of the wound re-epithelialization process. Hence, the stabilization of HIF-1α through the inhibition of PHD2 by sshRNA would be expected to up-regulate miR-210, which is not conducive to healing. Thus, the rationale for inhibiting miR-210 activity using an anti-miR-210 is to prevent the repression of keratinocyte growth and migration that would otherwise be a side-effect of stabilizing HIF-1α.

miR-21 plays a role opposite to that of miR-210; it promotes the migration of fibroblasts, endothelial cells and keratinocytes, which favor the wound healing process. The migration of fibroblasts into the wound bed results in recruitment of monocytes and induction of an inflammatory response, which is important in the initial phase of wound healing. Another key role of miR-21 is to promote cell growth and proliferation by regulating the PTEN pathway and inhibiting apoptotic regulators, both of which are also important for the initial phases of wound healing. HIF-1α up-regulates miR-21, but to a lesser extent than it does miR-210. Based on these considerations, we hypothesize that further supplementation of miR-21 activity would be beneficial for accelerating the healing process.

miR-210 may inhibit epithelialization by inhibiting keratinocyte growth and motility, whereas miR-21 may promote re-epithelialization by enhancing the motility of fibroblasts and keratinocytes. The inhibition of PHD2 by sshRNAs to stabilize HIF-1α, the abrogation of miR-210 by an anti-miR, and the supplementation of miR-21 activity by a pre-miR-21 mimic together may be an effective therapeutic strategy for wound healing, and may be superior to the effects of these RNAs alone.

siRNAs targeting viruses or cancer cells may be well suited to being combined in cocktails to avoid erosion of their effectiveness through mutation of single targets. Because the components of such a cocktail are chemically very similar and what side-effects they may have are mostly of a class-specific nature, siRNA cocktails may not have the same level of safety risk as do combinations of small molecule inhibitors. Based on their different roles in the wound healing process as summarized above, simultaneously modulating the activities of PHD2, miR-210 and miR-21 may profoundly affect the overall wound healing process. This therapeutic strategy would induce angiogenic factors and growth factors, and mobilize fibroblasts and keratinocytes within the wounded tissue to facilitate accelerated wound healing by regulating multiple biological pathways.

Because delivery is expected to be topical and the duration of treatment is only until the wound is healed, administration of high local doses, if needed to overcome any limitations in efficiency of tissue uptake, should be relatively safe and cost-effective. Although there are siRNA- and anti-miR-based drugs in development, there are currently no approved drug therapies based on RNAi. Success in this project could represent one of the first RNAi-based therapies, and the first therapy for synthetic shRNAs of any design. It would provide a boost to the prospects of RNAi as a general therapeutic approach for many diseases, especially skin disorders.

Described herein are therapeutically effective amounts of oligonucleotides, pharmaceutical compositions, pharmaceutical formulations, unit dosage forms, methods and kits to treat wounds in a subject in need thereof. In some embodiments, a therapeutically effective amount of a small RNA, pharmaceutical formulation, unit dosage form, or pharmaceutical composition of the present invention, either alone or in combination with another molecule or pharmaceutical composition, can be used for the treatment of wounds in a subject in need thereof. In some embodiments, a therapeutically effective amount of an oligonucleotide, pharmaceutical formulation, unit dosage form, or pharmaceutical composition of the present invention, either alone or in combination with another molecule or pharmaceutical composition, can be used for the manufacture of a medicament for the treatment of wounds in a subject in need thereof.

Complications in wound healing are widespread pathologies, as the inability to complete wound closure and increase the risk of infection, inflammation, scarring and fibrosis. Non-limiting examples of wounds include type II diabetic wounds, stab wounds, gunshot wounds, surgical wounds, thermal wounds, chemical wounds, electrical wounds, bites, stings, atherosclerotic wounds, deep vein thrombotic wounds, chronic wounds, acute wounds, ulcerative wounds, venous ulcerative wounds, pressure ulcerative wounds, infected wounds, inflammatory wounds, pressure wounds, incision wounds, superficial wounds, internal organ wounds, foot wounds, bed sore wounds, non-healing wounds, ischemic wounds, wounds associated with methicillin-resistant *Staphylococcus aureus*, pressure ulcerative wounds, diabetic ulcerative wounds, venous ulcerative wounds, arterial ulcerative wounds, and wounds of the elderly.

In some embodiments, a subject in need thereof is diagnosed with a disease or condition. In some embodiments, the disease or condition is a disease of pathological wound healing. Non-limiting examples of diseases or conditions of pathological wound healing include type II diabetes, diabetes mellitus, ischemia, venous stasis disease, peripheral vascular disease, an autoimmune disease, and a disease of dysregulated hypoxia response.

Non-limiting examples of organs and tissues in which wounds can occur include the skin, dermis, epidermis, hypodermis, connective tissue, breast, cervix, gastrointestinal tract, heart, kidney, large intestine, liver, lung, lymph nodes, ovary, pancreas, prostate, small intestine, spine or spinal cord, spleen, stomach, testes, thymus, or uterus. Non-limiting examples of cells in which a small RNA of the present invention can be contacted include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, cells of the endocrine or exocrine glands, germ cells, nurse cells, epithelial cells, endothelial cells, hormone secreting cells, contractile cells, skeletal muscle cells, cardiac muscle cells, blood cells, or cells of the bone, bone marrow, brain, breast, cervix, gastrointestinal tract, heart, kidney, large intestine, liver, lung, lymph nodes, ovary, pancreas, prostate, small intestine, spine or spinal cord, spleen, stomach, testes, thymus, or uterus.

Normal wound healing involves a coordinated cascade of events stimulated in part by the hypoxia resultant from injury to the vasculature at the wound site. This cascade includes angiogenesis, vasculogenesis, macrophage recruitment, inhibition of apoptosis, and the expansion and mobilization of fibroblasts and keratinocytes for re-epithelialization. In chronic wounds, the normal response to hypoxia is impaired and many of these cellular processes are hindered.

FIG. 1 illustrates the role of the hypoxia network 100 in this process. In the absence of hypoxia, the regulatory factor PHD2 101 hydroxylates 102 the transcription factor HIF-1α 103, leading to HIF-1α 103 degradation. During hypoxia, PHD2 101 is inactivated, liberating HIF-1α 103 to engage in transcriptional activation. In particular, HIF-1α 103 transcriptionally activates expression 104 of the miRNA miR-210 105. MiR-210 105 then engages in miRNA-mediated repression 106 of the transcription factor E2F3 107. This blocks the ability of E2F3 107 to transcriptionally activate 108 keratinocytes 109. In parallel, the miRNA miR-21 110 engages in miRNA-mediated repression 111 to activate keratinocytes 109. MiR-21 110 further engages in miRNA-mediated repression 112 in recruited fibroblasts 113. Activated keratinocytes 109 recruit and activate 114 fibroblasts 113. To impact the wound healing process 105, HIF-1α 103 in cells at the wound site and recruited fibroblasts 113 elicit gene expression programs 116 and 117, respectively, including expression of pro-survival factors, angiogenic factors, progenitor cell recruiting factors, and chemokines to recruit the cell types necessary for wound closure.

In some embodiments, an oligonucleotide or pharmaceutical composition of the present disclosure can increase wound healing, wound closure, or re-epithelialization. Non-limiting examples of an increase in wound healing include an increase in a rate of wound healing or an increase in an extent of wound healing. An oligonucleotide or pharmaceutical composition of the present disclosure can increase wound healing, wound closure, or re-epithelialization, relative to a control, by about 1%, about 5%, about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1000%, about 2000%, about 3000%, about 4000%, about 5000%, about 6000%, about 7000%, about 8000%, about 9000%, or about 10000%.

An oligonucleotide or pharmaceutical composition of the present disclosure can increase wound healing, wound closure, or re-epithelialization, relative to a control, from about 1% to about 5%, from about 5% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, from about 90% to about 100%, from about 100% to about 200%, from about 200% to about 300%, from about 300% to about 400%, from about 400% to about 500%, from about 500% to about 600%, from about 600% to about 700%, from about 700% to about 800%, from about 800% to about 900%, from about 900% to about 1000%, from about 1000% to about 2000%, from about 2000% to about 3000%, from about 3000% to about 4000%, from about 4000% to about 5000%, from about 5000% to about 6000%, from about 6000% to about 7000%, from about 7000% to about 8000%, from about 8000% to about 9000%, or from about 9000% to about 10000%.

An oligonucleotide or pharmaceutical composition of the invention can reduce wound size by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.9%, or about 100%.

An oligonucleotide or pharmaceutical composition of the invention can reduce wound size from about 1% to about 5%, from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, from about 98% to about 99%, from about 99% to about 99.5%, from about 99.5% to about 99.9%, or from about 99.9% to about 100%.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, transdermally, intravesicularlly, mucosally, intrapericardially, intraumbilically, intraocularally, orally, topically, locally, by inhalation, such as aerosol inhalation, by injection, by infusion, by continuous infusion, by localized perfusion, via a catheter, via a lavage, in creams, in lipid compositions, such as liposomes, or a combination thereof. A therapeutically effective amount of a small RNA of the present invention administered to a subject in need thereof can be determined by physical and physiological factors such as body weight, severity of condition, previous or concurrent therapeutic interventions, idiopathy of the patient and route of administration.

In some embodiments, a therapeutically effective amount of an oligonucleotide of the invention can comprise about 1 microgram per kilogram (µg/kg), about 2 µg/kg, about 3 µg/kg, about 4 µg/kg, about 5 µg/kg, about 6 µg/kg, about 7 µg/kg, about 8 µg/kg, about 9 µg/kg, about 10 µg/kg, about 20 µg/kg, about 30 µg/kg, about 40 µg/kg, about 50 µg/kg, about 60 µg/kg, about 70 µg/kg, about 80 µg/kg, about 90 µg/kg, about 100 µg/kg, about 200 µg/kg, about 300 µg/kg, about 400 µg/kg, about 500 µg/kg, about 1 milligram per kilogram (mg/kg), about 2 mg/kg, about 3 mg/kg, about 4 mg/kg, about 5 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, or about 100 mg/kg body weight.

In some embodiments, a therapeutically effective amount of an oligonucleotide can comprise from about 1 µg/kg to about 2 µg/kg, from about 2 µg/kg to about 3 µg/kg, from about 3 µg/kg to about 4 µg/kg, from about 4 µg/kg to about 5 µg/kg, from about 5 µg/kg to about 6 µg/kg, from about 6 µg/kg to about 7 µg/kg, from about 7 µg/kg to about 8 µg/kg, from about 8 µg/kg to about 9 µg/kg, from about 9 µg/kg to about 10 µg/kg, from about 10 µg/kg to about 20 µg/kg, from about 20 µg/kg to about 30 µg/kg, from about 30 µg/kg to about 40 µg/kg, from about 40 µg/kg to about 50 µg/kg, from about 50 µg/kg to about 60 µg/kg, from about 60 µg/kg to about 70 µg/kg, from about 70 µg/kg to about 80 µg/kg, from about 80 µg/kg to about 90 µg/kg, from about 90 µg/kg to about 100 µg/kg, from about 100 µg/kg to about 200 µg/kg, from about 200 µg/kg to about 300 µg/kg, from about 300 µg/kg to about 400 µg/kg, from about 400 µg/kg to about 500 µg/kg, from about 500 µg/kg to about 600 µg/kg, from about 600 µg/kg to about 700 µg/kg, from about 700 µg/kg to about 800 µg/kg, from about 800 µg/kg to about 900 µg/kg, from about 900 µg/kg to about 1 mg/kg, from about 1 mg/kg to about 2 mg/kg, from about 2 mg/kg to about 3 mg/kg, from about 3 mg/kg to about 4 mg/kg, from about 4 mg/kg to about 5 mg/kg, from about 5 mg/kg to about 6 mg/kg, from about 6 mg/kg to about 7 mg/kg, from about 7 mg/kg to about 8 mg/kg, from about 8 mg/kg to about 9 mg/kg, from about 9 mg/kg to about 10 mg/kg, from about 10 mg/kg to about 20 mg/kg, from about 20 mg/kg to about 30 mg/kg, from about 30 mg/kg to about 40 mg/kg, from about 40 mg/kg to about 50 mg/kg, from about 50 mg/kg to about 60 mg/kg, from about 60 mg/kg to about 70 mg/kg, from about 70 mg/kg to about 80 mg/kg, from about 80 mg/kg to about 90 mg/kg, or from about 90 mg/kg to about 100 mg/kg body weight.

In some embodiments, a therapeutically effective amount of an oligonucleotide can comprise about 50 µg, about 100 µg, about 150 µg, about 200 µg, about 250 µg, about 300 µg, about 350 µg, about 400 µg, about 450 µg, about 500 µg, about 600 µg, about 700 µg, about 800 µg, about 900 µg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 500 mg, about 600 mg, about 700 mg, about 800 mg, about 900 mg, or about 1 g.

In some embodiments, a therapeutically effective amount of an oligonucleotide can comprise from about 50 µg to about 100 µg, from about 100 µg to about 150 µg, from about 150 µg to about 200 µg, from about 200 µg to about 250 µg, from about 250 µg to about 300 µg, from about 300 µg to about 350 µg, from about 350 µg to about 400 µg, from about 400 µg to about 450 µg, from about 450 µg to about 500 µg, from about 500 µg to about 600 µg, from about 600 µg to about 700 µg, from about 700 µg to about 800 µg, from about 800 µg to about 900 µg, from about 900 µg to about 1 mg, from about 1 mg to about 1.5 mg, from about 1.5 mg to about 2 mg, from about 1 mg to about 1.5 mg, from about 1.5 mg to about 2 mg, from about 2 mg to about 2.5 mg, from about 2.5 mg to about 3 mg, from about 3 mg to about 3.5 mg, from about 3.5 mg to about 4 mg, from about 4 mg to about 4.5 mg, from about 4.5 mg to about 5 mg, from about 5 mg to about 5.5 mg, from about 5.5 mg to about 6 mg, from about 6 mg to about 6.5 mg, from about 6.5 mg to about 7 mg, from about 7 mg to about 7.5 mg, from about 7.5 mg to about 8 mg, from about 8 mg to about 8.5 mg, from about 8.5 mg to about 9 mg, from about 9 mg to about 9.5 mg, from about 9.5 mg to about 10 mg, from about 10 mg to about 11 mg, from about 11 mg to about 12 mg, from about 12 mg to about 13 mg, from about 13 mg to about 14 mg, from about 14 mg to about 15 mg, from about 15 mg to about 16 mg, from about 16 mg to about 17 mg, from about 17 mg to about 18 mg, from about 18 mg to about 19 mg, from about 19 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 60 mg, from about 60 mg to about 70 mg, from about 70 mg to about 80 mg, from about 80 mg to about 90 mg, from about 90 mg to about 100 mg, from about 100 mg to about 110 mg, from about 110 mg to about 120 mg, from about 120 mg to about 130 mg, from about 130 mg to about 140 mg, from about 140 mg to about 150 mg, from about 150 mg to about 160 mg, from about 160 mg to about 170 mg, from about 170 mg to about 180 mg, from about 180 mg to about 190 mg, from about 190 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 mg to about 1 g.

Polynucleotide Vectors

The present disclosure provides nucleic acids encoding the oligonucleotides disclosed herein, delivered by a suitable method, for example, a polynucleotide vector, to a subject in need thereof.

Delivery of a nucleic acid to a cell with a polynucleotide vector can be accomplished by a number of methods. Viral nucleic acid vector delivery methods use recombinant viruses for nucleic acid vector transfer. Non-viral nucleic acid vector delivery can comprise injecting naked DNA or RNA, use of carriers including lipid carriers, polymer carriers, chemical carriers and biological carriers such as biologic membranes, bacteria, and virus-like particles, and physical or mechanical approaches. A combination of viral and non-viral nucleic acid vector delivery methods can be used for efficient gene therapy.

Non-viral nucleic acid vector transfer can include injection of naked nucleic acid vector, for example, nucleic acid that is not protected or devoid of a carrier. In vivo, naked nucleic acid vectors can be subject to rapid degradation, low transfection levels, and poor tissue-targeting ability. Hydrodynamic injection methods can increase the targeting ability of naked nucleic acid vectors.

Non-viral nucleic acid vector delivery systems can include chemical carriers. These systems can include lipoplexes, polyplexes, dendrimers, and inorganic nanoparticles. A lipoplex is a complex of a lipid and a nucleic-acid that protects the nucleic acid from degradation and facilitates entry into cells. Lipoplexes can be prepared from neutral, anionic, or cationic lipids. Preparation of lipoplexes with cationic lipids can facilitate encapsulation of negatively charged nucleic acids. Lipoplexes with a net positive charge can interact more efficiently with a negatively charged cell membrane. Preparation of lipoplexes with a slight excess of positive charges can confer higher transfection efficiency. Lipoplexes can enter cells by endocytosis. Once inside the cell, lipoplexes can release the nucleic acid contents into the cytoplasm. A polyplex is a complex of a polymer and a nucleic acid. Most polyplexes are prepared from cationic polymers that facilitate assembly by ionic interactions between nucleic acids and polymers. Uptake of polyplexes into cells can occur by endocytosis. Inside the cells, polyplexes require co-transfected endosomal rupture agents such as inactivated adenovirus, for the release of the polyplex particle from the endocytic vesicle. Examples of polymeric carriers include polyethyleneimine, chitosan, poly(beta-amino esters) and polyphosphoramidate. Polyplexes show low toxicity, high loading capacity, and ease of fabrication. A dendrimer is a highly branched molecule. Dendrimers can be constructed to have a positively-charged surface or carry functional groups that aid temporary association of the dendrimer with nucleic acids. These dendrimer-nucleic acid complexes can be used for gene therapy. The dendrimer-nucleic acid complex can enter the cell by endocytosis. Nanoparticles prepared from inorganic material can be used for nucleic acid vector delivery. Examples of inorganic material can include gold, silica/silicate, silver, iron oxide, and calcium phosphate. Inorganic nanoparticles with a size of less than 100 nm can be used to encapsulate nucleic acids efficiently. The nanoparticles can be taken up by the cell via endocytosis. Inside the cell, the nucleic acid can be released from the endosome without degradation. Nanoparticles based on quantum dots can be prepared and offers the use of a stable fluorescence marker coupled with gene therapy. Organically modified silica or silicate can be used to target nucleic acids to specific cells in an organism.

Non-viral nucleic acid vector delivery systems can include biological methods including bactofection, biological liposomes, and virus-like particles (VLPs). Bactofection method comprises using attenuated bacteria to deliver nucleic acids to a cell. Biological liposomes, such as erythrocyte ghosts and secretion exosomes, are derived from the subject receiving gene therapy to avoid an immune response. Virus-like particles (VLP) or empty viral particles are produced by transfecting cells with only the structural genes of a virus and harvesting the empty particles. The empty particles are loaded with nucleic acids to be transfected for gene therapy.

Delivery of nucleic acid vectors can be enhanced by physical methods. Examples of physical methods include electroporation, gene gun, sonoporation, and magnetofection. The electroporation method uses short high-voltage pulses to transfer nucleic acid across the cell membrane. These pulses can lead to formation of temporary pores in the cell membrane, thereby allowing nucleic acid to enter the cell. Electroporation can be efficient for a broad range of cells. Electron-avalanche transfection is a type of electroporation method that uses very short, for example, microsecond, pulses of high-voltage plasma discharge for increasing efficiency of nucleic acid vector delivery. The gene gun method utilizes nucleic acid-coated gold particles that are shot into the cell using high-pressure gas. Force generated by the gene gun allows penetration of nucleic acid into the cells, while the gold is left behind on a stopping disk. The sonoporation method uses ultrasonic frequencies to modify permeability of cell membrane. Change in permeability allows uptake of nucleic acid into cells. The magnetofection method uses a magnetic field to enhance nucleic acid uptake. In this method, nucleic acid is complexed with magnetic particles. A magnetic field is used to concentrate the nucleic acid complex and bring them in contact with cells.

Viral nucleic acid vector delivery systems use recombinant viruses to deliver nucleic acids for gene therapy. Non-limiting examples of viruses that can be used to deliver nucleic acids include retrovirus, adenovirus, herpes simplex virus, adeno-associated virus, vesicular stomatitis virus, reovirus, vaccinia, pox virus, and measles virus.

Retroviral vectors can be used in the disclosure. Retrovirus is an enveloped virus that contains a single-stranded RNA genome. Retroviruses can integrate inside a host cell via reverse transcription. Retroviruses can enter a host cell by binding to specific membrane-bound receptors. Inside the host cell cytoplasm, retroviral reverse transcriptase generates double-stranded DNA from the viral RNA genome template. Retroviral enzyme integrase incorporates the new viral DNA into host cell genome, where the viral DNA is transcribed and translated along with host cell genes. Retroviral gene therapy vectors can be used for chromosomal integration of the transferred vector genomes, thereby leading to stable genetic modification of treated cells. Non-limiting examples of retroviral vectors include Moloney murine leukemia viral (MMLV) vectors, HIV-based viral vectors, gammaretroviral vectors, C-type retroviral vectors, and lentiviral vectors. Lentivirus is a subclass of retrovirus. While some retroviruses can infect only dividing cells, lentiviruses can infect and integrate into the genome of actively dividing cells and non-dividing cells.

Adenovirus-based vectors can be used in the disclosure. Adenovirus is a non-enveloped virus with a linear double-stranded genome. Adenoviruses can enter host cells using interactions between viral surface proteins and host cell receptors that lead to endocytosis of the adenovirus particle. Once inside the host cell cytoplasm, the adenovirus particle is released by the degradation of the endosome. Using cellular microtubules, the adenovirus particle gains entry into the host cell nucleus, where adenoviral DNA is released. Inside the host cell nucleus, the adenoviral DNA is transcribed and translated. Adenoviral DNA is not integrated into the host cell genome. Adenoviral DNA is not replicated during host cell division. Gene therapy using adenoviral vectors can require multiple administrations if the host cell population is replicating.

Herpes simplex virus (HSV)-based vectors can be used in the disclosure. HSV is an enveloped virus with a linear double-stranded DNA genome. Interactions between surface proteins on the host cell and HSV lead to pore formation in the host cell membrane. These pores allow HSV to enter the host cell cytoplasm. Inside the host cell, HSV uses the nuclear entry pore to enter the host cell nucleus where HSV DNA is released. HSV can persist in host cells in a state of latency. Herpes simplex virus 1 and 2 (HSV-1 and HSV-2), also known as human herpes virus 1 and 2 (HHV-1 and HHV-2), are members of the herpes virus family.

Alphavirus-based vectors can be used to deliver nucleic acids. Examples of alphavirus-based vectors include vectors derived from semliki forest virus and sindbis virus. Alphavirus-based vectors can provide high transgene expression and the ability to transduce a wide variety of cells. Alphavirus vectors can be modified to target specific tissues. Alphaviruses can persist in a latent state in host cells, thereby offering the advantage of long-term nucleic acid expression in the cell.

Pox/vaccinia-based vectors such as orthopox or avipox vectors can be used in the disclosure. Pox virus is a double stranded DNA virus that can infect diving and non-dividing cells. Pox viral genome can accommodate up to 25 kilobase transgenic sequence. Multiple genes can be delivered using a single vaccinia viral vector.

In one aspect, the present disclosure provides a recombinant virus, such as an adeno-associated virus (AAV), as a vector to deliver a nucleic acid encoding a shRNA, sshRNA, or pre-miRNA mimic to a subject in need thereof.

Adeno-associated virus (AAV) is a small, nonenveloped virus that belongs to the Parvoviridae family. AAV genome is a linear single-stranded DNA molecule of about 4,800 nucleotides. The AAV DNA comprises two inverted terminal repeats (ITRs) at both ends of the genome and two sets of open reading frames. The ITRs serve as origins of replication for the viral DNA and as integration elements. The open reading frames encode for the Rep (non-structural replication) and Cap (structural capsid) proteins. AAV can infect dividing cells and quiescent cells. AAV is common in the general population and can persist naturally in the host.

AAV can be engineered for use as a gene therapy vector by substituting the coding sequence for both AAV genes with a transgene (transferred nucleic acid) to be delivered to a cell. The substitution eliminates immunologic or toxic side effects due to expression of viral genes. The transgene can be placed between the two ITRs (145 basepair (bp)) on the AAV DNA molecule. AAV-based vectors can transencapsidate the genome allowing large variations in vector biology and tropism.

When producing recombinant AAV (rAAV), the viral genes or adenovirus genes providing helper functions to AAV can be supplied in trans to allow for production of the rAAV particles. In this way, rAAV can be produced through a three-plasmid system, decreasing the probability of production of wild-type virus.

AAV vector of the present disclosure can be generated using any AAV serotype. Non-limiting examples of serotypes include AAV1, AAV2, AAV2.5, AAV3, AAV4, AAV5, AAV6, AAV7, AAV8, AAV9, AAV10, AAV11, AAV12, rh10, and hybrids thereof.

AAV vectors can be modified for immune evasion or to enhance therapeutic output. The modifications can include genetic manipulation of the viral capsid. Proteins in the viral capsid can be rationally designed. The viral capsid can be modified by introducing exogenous agents such as antibodies, copolymers, and cationic lipids to evade the immune system. AAV vectors can be engineered to enhance the targeting ability. Targeting peptides or ligands can be inserted onto the capsid surface to enhance transduction into specific tissue. Capsid proteins from more than one serotype of AAV can be combined to produce a mosaic AAV vector comprising a capsid particle with enhanced targeting ability of the AAV vector. Tissue-specific promoters can be added to the viral vector to express the transgene in desired tissue types.

AAV vector can be modified to be self-complementary. A self-complementary AAV vector can comprise both strands of the viral DNA, thereby alleviating the requirement for host-cell second-strand DNA synthesis. The use of self-complementary AAV vectors can promote efficient transfer of nucleic acids into host genome.

A pseudotyped virus can be used for the Delivery of nucleic acid vectors. Psuedotyping involves substitution of endogenous envelope proteins of the virus by envelope proteins from other viruses or chimeric proteins. The foreign envelope proteins can confer a change in host tropism or alter stability of the virus. An example of a pseudotyped virus useful for gene therapy includes vesicular stomatitis virus G-pseudotyped lentivirus (VSV G-pseudotyped lentivirus) that is produced by coating the lentivirus with the envelope G-protein from Vesicular stomatitis virus. VSV G-pseudotyped lentivirus can transduce almost all mammalian cell types.

A hybrid vector having properties of two or more vectors can be used for nucleic acid vector delivery to a host cell. Hybrid vectors can be engineered to reduce toxicity or improve therapeutic transgene expression in target cells. Non-limiting examples of hybrid vectors include AAV/adenovirus hybrid vectors, AAV/phage hybrid vectors, and retrovirus/adenovirus hybrid vectors.

A viral vector can be replication-competent. A replication-competent vector contains all the genes necessary for replication, making the genome lengthier than replication-defective viral vectors. A viral vector can be replication-defective, wherein the coding region for the genes essential for replication and packaging are deleted or replaced with other genes. Replication-defective viruses can transduce host cells and transfer the genetic material, but do not replicate. A helper virus can be supplied to help a replication-defective virus replicate.

A viral vector can be derived from any source, for example, humans, non-human primates, dogs, fowl, mouse, cat, sheep, and pig.

The composition and methods of the disclosure provide for the delivery of a nucleic acid that encodes for a shRNA, sshRNA, or pre-miRNA mimic to a subject in need thereof. The nucleic acid can be delivered by a viral vector, for example, an adeno-associated virus (AAV), adenovirus, retrovirus, herpes simplex virus, lentivirus, poxvirus, hemagglutinating virus of Japan-liposome (HVJ) complex, Moloney murine leukemia virus, or HIV-based virus. The nucleic acid can be delivered by a suitable non-viral method, for example, injection of naked nucleic acid, use of carriers such as lipid, polymer, biological or chemical carriers, or physical/mechanical approaches. The nucleic acid can be delivered by a combination of viral and non-viral methods.

The nucleic acid of the disclosure can be generated using any method. The nucleic acid can be synthetic, recombinant, isolated, or purified. The nucleic acid can comprise, for example, a nucleic acid sequence that encodes a shRNA, sshRNA, or pre-miRNA mimic.

A vector of the present disclosure can comprise one or more types of nucleic acids. The nucleic acids can include DNA or RNA. RNA nucleic acids can include a transcript of a gene of interest, for example, a shRNA, sshRNA, pre-miRNA mimic, introns, untranslated regions, and termination sequences. DNA nucleic acids can include the gene of interest, promoter sequences, untranslated regions, and termination sequences. A combination of DNA and RNA can be used. The nucleic acids can be double-stranded or single-stranded. The nucleic acid can include non-natural or altered nucleotides.

A vector of the disclosure can comprise additional nucleic acid sequences including promoters, enhancers, repressors, insulators, polyadenylation signals (polyA), untranslated regions (UTRs), termination sequences, transcription terminators, internal ribosome entry sites (IRES), introns, origins of replication sequence, primer binding sites, att sites, encapsidation sites, polypurine tracts, Long Terminal Repeats (LTRs), and linker sequences. The vector can be modified to target specific cells, for example, cancer cells, or to a tissue, for example, retina.

Expression of a shRNA, sshRNA, pre-miRNA mimic can be under the control of a regulatory sequence. The regulatory sequence can comprise a promoter. Promoters from any suitable source including virus, mammal, human, insect, plant, yeast, and bacteria, can be used. Tissue-specific promoters can be used. Promoters can be constitutive, inducible, or repressible. Promoters can be unidirectional (initiating transcription in one direction) or bi-directional (initiating transcription in either a 3' or 5' direction). Non-limiting examples of promoters include the T7 bacterial expression system, pBAD (araA) bacterial expression system, the cytomegalovirus (CMV) promoter, the SV40 promoter, the Rous sarcoma virus promoter, MMT promoter, EF-1 alpha promoter, UB6 promoter, chicken beta-actin promoter, CAG promoter, RPE65 promoter, opsin promoter, HIV-1 promoter, HIV-2 promoter, AAV promoter, adenovirus promoters such as from the E1A, E2A, or MLP region, cauliflower mosaic virus promoter, HSV-TK promoter, avian sarcoma virus promoter, MLV promoter, MMTV promoter, and rat insulin promoter. Inducible promoters can include, for example, the Tet system, the ecdysone inducible system, the T-REX™ system, LACSWITCH™ System, and the Cre-ERT tamoxifen inducible recombinase system.

A promoter sequence, intron sequence, polyA sequence, untranslated region, or linker sequence can be about 1 base or base pair, about 10 bases or base pairs, about 20 bases or base pairs, about 50 bases or base pairs, about 100 bases or base pairs, about 500 bases or base pairs, about 1000 bases or base pairs, about 2000 bases or base pairs, about 3000 bases or base pairs, about 4000 bases or base pairs, about 5000 bases or base pairs, about 6000 bases or base pairs, about 7000 bases or base pairs, about 8000 bases or base pairs, about 9000 bases or base pairs, or about 10000 bases or base pairs. A promoter sequence, intron sequence, polyA sequence, untranslated region, or linker sequence can be a length from about 1 to about 10 bases or base pairs, from about 10 to about 20 bases or base pairs, from about 20 to about 50 bases or base pairs, from about 50 to about 100 bases or base pairs, from about 100 to about 500 bases or base pairs, from about 500 to about 1000 bases or base pairs, from about 1000 to about 2000 bases or base pairs, from about 2000 to about 3000 bases or base pairs, from about 3000 to about 4000 bases or base pairs, from about 4000 to about 5000 bases or base pairs, from about 5000 to about 6000 bases or base pairs, from about 6000 to about 7000 bases or base pairs, from about 7000 to about 8000 bases or base pairs, from about 8000 to about 9000 bases or base pairs, or from about 9000 to about 10000 bases or base pairs in length.

A vector of the disclosure can comprise nucleic acids encoding a selectable marker. The selectable marker can be positive, negative or bifunctional. The selectable marker can be an antibiotic-resistance gene. Examples of antibiotic resistance genes include markers conferring resistance to kanamycin, gentamicin, ampicillin, chloramphenicol, tetracycline, doxycycline, hygromycin, puromycin, zeomycin, or blasticidin. The selectable marker can allow imaging of the host cells, for example, a fluorescent protein. Examples of imaging marker genes include GFP, eGFP, RFP, CFP, YFP, dsRed, Venus, mCherry, mTomato, and mOrange.

A vector of the disclosure can comprise fusion proteins. The fusion partner can comprise a signal polypeptide that targets the protein to the desired site. The fusion partner can comprise a polypeptide tag, for example, a poly-His or a Flag peptide, that facilitates purification of the protein. The fusion partner can comprise an imaging tag, for example, a fluorescent protein, for imaging the cells. A vector of the disclosure can comprise chemical conjugates.

A vector of the disclosure can comprise components to confer additional properties to the vector. These properties can include targeting of the vector to a specific tissue, uptake of vector into a host cell, entry of nucleic acid into nucleus, incorporation of nucleic acid into host cell genome, transgene expression in host cell, immune evasion, and vector stability.

A vector of the disclosure can be generated by any suitable methods. The method can include use of transgenic cells including for example, mammalian cells such as HEK293, insect cells such as Sf9, animal cells or fungal cells.

A viral vector of the disclosure can be measured as plaque forming units (pfu). The pfu of a viral vector can be, for example, from about $10^1$ to about $10^{18}$ pfu. A viral vector of the disclosure can be, for example, at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, or at least $10^{18}$ pfu. A viral vector of the disclosure can be, for example, at most $10^1$, at most $10^2$, at most $10^3$, at most $10^4$, at most $10^5$, at most $10^6$, at most $10^7$, at most $10^8$, at most $10^9$, at most $10^{10}$, at most $10^{11}$, at most $10^{12}$, at most $10^{13}$, at most $10^{14}$, at most $10^{15}$, at most $10^{16}$, at most $10^{17}$, or at most $10^{18}$ pfu.

A viral vector of the disclosure can be measured as vector genomes. A viral vector of the disclosure can be, for example, from about $10^1$ to about $10^{18}$ vector genomes. A viral vector of the disclosure can be, for example, at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, or at least $10^{18}$ vector genomes. A viral vector of the disclosure can be, for example, at most $10^1$, at most $10^2$, at most $10^3$, at most $10^4$, at most $10^5$, at most $10^6$, at most $10^7$, at most $10^8$, at most $10^9$, at most $10^{10}$, at most $10^{11}$, at most $10^{12}$, at most $10^{13}$, at most $10^{14}$, at most $10^{15}$, at most $10^{16}$, at most $10^{17}$, or at most $10^{18}$ vector genomes.

A viral vector of the disclosure can be measured using multiplicity of infection (MOI). MOI can be, for example, the ratio, or multiple of vector or viral genomes to the cells to which the nucleic acid can be delivered. A viral vector of the disclosure can be, for example, from about $10^1$ to about $10^{18}$ MOI. A viral vector of the disclosure can be, for example, at least about $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, or at least $10^{18}$ MOI. A viral vector of the disclosure can be, for example, at most $10^1$, at most $10^2$, at most $10^3$, at most $10^4$, at most $10^5$, at most $10^6$, at most $10^7$, at most $10^8$, at most $10^9$, at most $10^{10}$, at most $10^{11}$, at most $10^{12}$, at most $10^{13}$, at most $10^{14}$, at most $10^{15}$, at most $10^{16}$, at most $10^{17}$, or at most $10^{18}$ MOI.

The amount of nucleic acid vector can be, for example, from about 1 pg to about 1 ng. The amount of nucleic acid vector can be, for example, from about 1 ng to about 1 µg. The amount of nucleic acid vector can be, for example, from about 1 µg to about 1 mg. The amount of nucleic acid vector can be, for example, from about 1 mg to about 1 g. The amount of nucleic acid vector can be, for example, from about 1 g to about 5 g. The amount of nucleic acid vector can be, for example, about 1 pg, about 10 pg, about 100 pg, about 200 pg, about 300 pg, about 400 pg, about 500 pg, about 600 pg, about 700 pg, about 800 pg, about 900 pg, about 1 ng, about 10 ng, about 100 ng, about 200 ng, about 300 ng, about 400 ng, about 500 ng, about 600 ng, about 700 ng, about 800 ng, about 900 ng, about 1 µg, about 10 µg, about 100 µg, about 200 µg, about 300 µg, about 400 µg, about 500 µg, about 600 µg, about 700 µg, about 800 µg, about 900 µg, about 1 mg, about 10 mg, about 100 mg, about 200 mg, about 300 mg, about 400 mg, about 500 mg, about 600 mg, about 700 mg, about 800 mg, about 900 mg, about 1 g, about 2 g, about 3 g, about 4 g, or about 5 g.

The amount of nucleic acid vector can be from about 1 pg to about 10 pg, from about 10 pg to about 100 pg, from about 100 pg to about 200 pg, from about 200 pg to about 300 pg, from about 300 pg to about 400 pg, from about 400 pg to about 500 pg, from about 500 pg to about 600 pg, from about 600 pg to about 700 pg, from about 700 pg to about 800 pg, from about 800 pg to about 900 pg, from about 900 pg to about 1 ng, from about 1 ng to about 10 ng, from about 10 ng to about 100 ng, from about 100 ng to about 200 ng, from about 200 ng to about 300 ng, from about 300 ng to about 400 ng, from about 400 ng to about 500 ng, from about 500 ng to about 600 ng, from about 600 ng to about 700 ng, from about 700 ng to about 800 ng, from about 800 ng to about 900 ng, from about 900 ng to about 1 µg, from about 1 µg to about 10 µg, from about 10 µg to about 100 µg, from about 100m to about 200 µg, from about 200m to about 300 µg, from about 300m to about 400m, from about 400m to about 500 µg, from about 500m to about 600m, from about 600m to about 700m, from about 700m to about 800m, from about 800m to about 900m, from about 900m to about 1 mg, from about 1 mg to about 10 mg, from about 10 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1 g, from about 1 g to about 2 g, from about 2 g to about 3 g, from about 3 g to about 4 g, or from about 4 g to about 5 g.

A viral vector of the disclosure can be measured as recombinant viral particles. A viral vector of the disclosure can be, for example, from about $10^1$ to about $10^{18}$ recombinant viral particles. A viral vector of the disclosure can be, for example, at least about $10^1$, at least about $10^2$, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, or at least about $10^{18}$ recombinant viral particles. A viral vector of the disclosure can be, for example, at most about $10^1$, at most about $10^2$, at most about $10^3$, at most about $10^4$, at most about $10^5$, at most about $10^6$, at most about $10^7$, at most about $10^8$, at most about $10^9$, at most about $10^{10}$, at most about $10^{11}$, at most about $10^{12}$, at most about $10^{13}$, at most about $10^{14}$, at most about $10^{15}$, at most about $10^{16}$, at most about $10^{17}$, or at most about $10^{18}$ recombinant viral particles.

Pharmaceutical Formulations

The oligonucleotides of the invention can be administered to a subject alone or in the form of a pharmaceutical composition. Pharmaceutical compositions can be formulated using one or more pharmaceutically-acceptable carriers, diluents, substrates, excipients or auxiliaries which facilitate processing of the oligonucleotides into preparations which can be used pharmaceutically. Formulation is dependent upon the route of administration chosen.

For topical administration, the oligonucleotides of the invention can be formulated as solutions, gels, ointments, creams, or suspensions, onto transdermal patches, meshes, or films. Systemic formulations include those designed for administration by injection, such as subcutaneous, intravenous, intramuscular, intrathecal or intraperitoneal injection, as well as those designed for transdermal, transmucosal, inhalation, oral or pulmonary administration. For injection, the nucleic acids of the invention can be formulated in aqueous solutions, preferably in physiologically compatible buffers such as Hanks' solution, Ringer's solution, or physiological saline buffer. The solution can contain formulatory agents such as suspending, stabilizing or dispersing agents. Alternatively, the oligonucleotides can be in powder form for constitution with a suitable vehicle, such as sterile pyrogen-free water, before use. For transmucosal administration, penetrants appropriate to the barrier to be permeated are used in the formulation.

In some embodiments, the oligonucleotides of the invention can be formulated onto transdermal patches, meshes, or films. Non-limiting examples of transdermal patches, meshes, or films include dressings, medical dressings, occlusive dressings, transparent dressings, and waterproof dressings. Oligonucleotides of the invention can be applied together or sequentially with an alternating charged material to form a layer on a pharmaceutically-acceptable substrate, such as a transdermal patch, mesh or film. Non-limiting examples of the layer include a printed layer and a cationic layer. The thin layer biodegrades to allow the oligonucleotide to undergo sustained release. In some embodiments, the sustained release can occur over about 1 day, about 2 days, about 3 days, about 4 days, about 5 days, about 6 days, about 7 days, about 8 days, about 9 days, about 10 days, about 11 days, about 12 days, about 13 days, about 14 days, or about 15 days. In some embodiments, the sustained release can occur from about 1 day to about 2 days, from about 2 days to about 3 days, from about 3 days to about 4 days, from about 4 days to about 5 days, from about 5 days to about 6 days, from about 6 days to about 7 days, from about 7 days to about 8 days, from about 8 days to about 9 days, from about 9 days to about 10 days, from about 10 days to about 11 days, from about 11 days to about 12 days, from about 12 days to about 13 days, from about 13 days to about 14 days, or from about 14 days to about 15 days.

For oral administration, the nucleic acids can be readily formulated by combining the molecules with pharmaceutically-acceptable carriers. Oligonucleotides of the present invention can be formulated with a pharmaceutically-acceptable carrier to generate tablets, pills, dragees, capsules, liquids, gels, syrups, slurries, and suspensions for oral ingestion by a subject in need thereof. For oral solid formulations, such as powders, capsules and tablets, suitable excipients include fillers chosen from: sugars, cellulose preparations, granulating agents, binding agents, and disintegrating agents. Non-limiting examples of sugars include lactose, sucrose, mannitol and sorbitol. Non-limiting examples of cellulose preparations include maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). Non-limiting examples of disintegrating agents include cross-linked polyvinylpyrrolidone, agar, and alginic acid or a salt thereof such as sodium alginate. If desired, solid dosage forms can be sugar-coated or enteric-coated. For oral liquid preparations, such as suspensions, elixirs and solutions, suitable carriers, excipients or diluents include water, glycols, oils, and alcohols. Flavoring agents, preservatives, and coloring agents can further be added. For buccal administration, the molecules can take the form of tablets or lozenges. For administration by inhalation, the oligonucleotides can be delivered in the form of an aerosol spray from pressurized packs or a nebulizer, with the use of a suitable propellant, such as dichlorodifluoromethane, trichlorofluoromethane, dichlorotetrafluoroethane, and carbon dioxide. In the case of a pressurized aerosol, the dosage unit can be determined by providing a valve to deliver a metered amount. Capsules and cartridges of gelatin for use in an inhaler or insufflator can be formulated containing a powder mix of the nucleic acids and a suitable powder base such as lactose or starch. The oligonucleotides can also be formulated in rectal or vaginal compositions such as suppositories and retention enemas, for example containing conventional suppository bases such as cocoa butter and other glycerides.

In addition to the formulations described previously, the oligonucleotides can also be formulated as a depot preparation. Such long acting formulations can be administered by implantation subcutaneously or intramuscularly or by intramuscular injection. For depot formulation, oligonucleotides can be formulated with: suitable polymeric or hydrophobic materials, for example, as an emulsion in an acceptable oil; ion exchange resins; or sparingly soluble derivatives, for example, a sparingly soluble salt.

In some embodiments, liposomes and emulsions can be formulated as delivery vehicles to deliver nucleic acids of the present invention. A nucleic acid of the invention can be administered in combination with a carrier or lipid to increase cellular uptake. For example, the small RNA can be administered in combination with a cationic lipid. Non-limiting examples of cationic lipids include lipofectin, DOTMA, DOPE, DOTAP, DOTAP:cholesterol, and cholesterol derivative formulations. In some embodiments, lipid or liposomal formulations include nanoparticles.

In some embodiments, oligonucleotides can be administered in combination with a cationic amine such as poly(L-lysine).

Oligonucleotides can be delivered using a sustained-release system, such as semipermeable matrices of solid polymers containing the small RNA. Sustained-release capsules can, depending on their chemical nature, release the small RNA for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, or about 16 weeks.

Nucleic acids can be included in any of the above-described formulations as the free acids, free bases, or as pharmaceutically-acceptable salts. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid. Acid addition salts can be, for example, monosalts, disalts, trisalts, tetrasalts, or higher salts. Such forms can have counterions that are all the same anion, or encompass a plurality of chemically-distinct anions.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Metal salts can arise from the addition of an inorganic base to a compound of the invention. The inorganic base consists of a metal cation paired with a basic counterion, such as, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, or zinc. In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrrazine. In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Pharmaceutical compositions of the present invention comprise an effective amount of one or more oligonucleotides dissolved or dispersed in a pharmaceutically-acceptable carrier. Pharmaceutically-acceptable carriers include any solvents, dispersion media, coatings, surfactants, antioxidants, preservatives, antibacterial agents, antifungal agents, isotonic agents, absorption delaying agents, salts, preservatives, drugs, drug stabilizers, gels, binders, excipients, disintegration agents, lubricants, sweetening agents, flavoring agents, dyes, or a combination thereof (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The oligonucleotides can comprise different types of carriers depending on whether it is to be administered in solid, liquid or aerosol form, and whether it need to be sterile for such routes of administration as injection.

In some embodiments, pharmaceutical compositions can comprise about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9% small RNA by mass. In some embodiments, pharmaceutical compositions can comprise from about 0.1% to about 0.5%, from about 0.5% to about 1%, from about 1% to about 5%, from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, from about 95% to about 96%, from about 96% to about 97%, from about 97% to about 98%, from about 98% to about 99%, from about 99% to about 99.5%, or from about 99.5% to about 99.9% small RNA by mass.

In some embodiments, a composition of the present invention can have a concentration of the small RNA of about 0.01 milligrams per milliliter (mg/mL), about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 6 mg/mL, about 7 mg/mL, about 8 mg/mL, about 9 mg/mL, about 10 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL, or about 100 mg/mL.

In some embodiments, a composition of the present invention can have a concentration of the small RNA from about 0.01 mg/mL to about 0.05 mg/mL, from about 0.05 mg/mL to about 0.1 mg/mL, from about 0.1 mg/mL to about 0.2 mg/mL, from about 0.2 mg/mL to about 0.3 mg/mL, from about 0.3 mg/mL to about 0.4 mg/mL, from about 0.4 mg/mL to about 0.5 mg/mL, from about 0.5 mg/mL to about 0.6 mg/mL, from about 0.6 mg/mL to about 0.7 mg/mL, from about 0.7 mg/mL to about 0.8 mg/mL, from about 0.8 mg/mL to about 0.9 mg/mL, from about 0.9 mg/mL to about 1 mg/mL, from about 1 mg/mL to about 1.5 mg/mL, from about 1.5 mg/mL to about 2 mg/mL, from about 2 mg/mL to about 2.5 mg/mL, from about 2.5 mg/mL to about 3 mg/mL, from about 3 mg/mL to about 3.5 mg/mL, from about 3.5 mg/mL to about 4 mg/mL, from about 4 mg/mL to about 4.5 mg/mL, from about 4.5 mg/mL to about 5 mg/mL, from about 5 mg/mL to about 6 mg/mL, from about 6 mg/mL to about 7 mg/mL, from about 7 mg/mL to about 8 mg/mL, from about 8 mg/mL to about 9 mg/mL, from about 9 mg/mL to about 10 mg/mL, from about 10 mg/mL to about 11 mg/mL, from about 11 mg/mL to about 12 mg/mL, from about 12 mg/mL to about 13 mg/mL, from about 13 mg/mL to about 14 mg/mL, from about 14 mg/mL to about 15 mg/mL, from about 15 mg/mL to about 16 mg/mL, from about 16 mg/mL to about 17 mg/mL, from about 17 mg/mL to about 18 mg/mL, from about 18 mg/mL to about 19 mg/mL, from about 19 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, from about 45 mg/mL to about 50 mg/mL, from about 50 mg/mL to about 60 mg/mL, from about 60 mg/mL to about 70 mg/mL, from about 70 mg/mL to about 80 mg/mL, from about 80 mg/mL to about 90 mg/mL, or from about 90 mg/mL to about 100 mg/mL.

In some embodiments, the composition can comprise an antioxidant to retard oxidation of one or more component. Additionally, compositions can comprise preservatives such as various antibacterial and antifungal agents. Non-limiting examples of preservatives include parabens, such as methylparabens and propylparabens, chlorobutanol, phenol, sorbic acid, thimerosal, or a combination thereof.

In some embodiments, the composition is in a liquid form in which a carrier can be a solvent or dispersion medium comprising water, ethanol, a polyol such as glycerol, propylene glycol, and liquid polyethylene glycol, a lipid such as triglycerides, vegetable oils, and liposomes, or a combination thereof. Fluidity can be maintained by the use of a coating, such as lecithin; by the maintenance of the required particle size by dispersion in carriers such as liquid polyol or lipids; by the use of surfactants, such as hydroxypropylcellulose; or a combination thereof. In some embodiments, the composition will comprise isotonic agents, such as sugars, sodium chloride or a combination thereof. In some embodiments, the compositions of the present invention are stored in a lyophilized form for solubilization with a liquid carrier as described herein. In some embodiments, the lyophilized form is stored in an airtight container with a rubber stopper seal.

In some embodiments, the composition can be administered as eye drops, nasal solutions, nasal sprays, aerosols or inhalants. In some embodiments, the drops, sprays, solutions, aerosols or inhalants are isotonic with a pH from about 7.0 to about 7.4 or slightly buffered to maintain a pH of about 5.5 to about 6.5. In some embodiments, the composition can further comprise antimicrobial preservatives as described above. In some embodiments, the composition can further comprise drugs such as antibiotics or antihistamines.

In some embodiments, the oligonucleotides are formulated for oral administration as a solid or liquid composition. In some embodiments, the oral composition can comprise solutions, suspensions, emulsions, tablets, pills, capsules such as hard or soft shelled gelatin capsules, sustained release formulations, buccal compositions, troches, elixirs, suspensions, syrups, wafers, or a combination thereof. Oral compositions can be incorporated directly with the food of the diet of the subject. Non-limiting examples of carriers for oral administration include inert diluents, assimilable edible carriers and a combination thereof. In some embodiments, the syrup or elixir can comprise a sweetening agent, a preservative, a flavoring agent, a dye, a preservative, or a combination thereof.

In some embodiments, the composition can comprise one or more of the following: a binder such as gum tragacanth, acacia, cornstarch, gelatin or a combination thereof; an excipient such as dicalcium phosphate, mannitol, lactose, starch, magnesium stearate, sodium saccharine, cellulose, magnesium carbonate or a combination thereof; a disintegrating agent such as corn starch, potato starch, alginic acid or a combination thereof; a lubricant such as magnesium stearate; a sweetening agent such as sucrose, lactose, saccharin or a combination thereof; a flavoring agent such as peppermint, oil of wintergreen, cherry flavoring, orange flavoring; or a combination thereof. A capsule can further comprise carriers such as a liquid carrier. In some embodiments, the dosage unit, such as tablets, capsules, or pills, can comprise a coating, such as shellac, sugar or a combination thereof.

In some embodiments, prolonged absorption of an injectable composition can be brought about by the use in the compositions of agents delaying absorption, such as aluminum monostearate, gelatin, biodegradable matrices or gels, time-release matrices or gels, or a combination thereof. Non-limiting examples of time-release matrices or gels include agarose, agarose colloid matrix, such 0.4% (w/v), 12 kDa, hydrogels, sodium carboxymethylcellulose, and polyethyleneimine. An agent delaying absorption can release a composition over about 1 minute, about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 12 hours, about 1 day, about 2 days, about 3 days, about 4 days, about 5 days, about 6 days, about 1 week, about 8 days, about 9 days, about 10 days, about 11 days, about 12 days, about 13 days, about 2 weeks, about 15 days, about 16 days, about 17 days, about 18 days, about 19 days, about 20 days, about 3 weeks, or about 1 month. An agent delaying absorption can release a composition over from about 1 minute to about 5 minutes, from about 5 minutes to about 10 minutes, from about 10 minutes to about 20 minutes, from about 20 minutes to about 30 minutes, from about 30 minutes to about 40 minutes, from about 40 minutes to about 50 minutes, from about 50 minutes to about 1 hour, from about 1 hour to about 2 hours, from about 2 hours to about 3 hours, from about 3 hours to about 4 hours, from about 4 hours to about 5 hours, from about 5 hours to about 6 hours, from about 6 hours to about 12 hours, from about 12 hours to about 1 day, from about 1 day to about 2 days, from about 2 days to about 3 days, from about 3 days to about 4 days, from about 4 days to about 5 days, from about 5 days to about 6 days, from about 6 days to about 1 week, from about 1 week to about 8 days, from about 8 days to about 9 days, from about 9 days to about 10 days, from about 10 days to about 11 days, from about 11 days to about 12 days, from about 12 days to about 13 days, from about 13 days to about 2 weeks, from about 2 weeks to about 15 days, from about 15 days to about 16 days, from about 16 days to about 17 days, from about 17 days to about 18 days, from about 18 days to about 19 days, from about 19 days to about 20 days, from about 20 days to about 3 weeks, or from about 3 weeks to about 1 month, In some embodiments, the composition is formulated to be sterile. In some embodiments, endotoxin contamination is less than about 0.5 nanograms per milligram (ng/mg) protein.

Kits

The present invention can include kits for regulating expression of a target transcript in a cell, the kits comprising oligonucleotides as described herein. The kits may comprise any one of the sshRNAs, miRNA antagonists or pre-miRNA mimics, as disclosed herein, or any combination thereof. The kits may comprise an sshRNA targeting PHD2, an miRNA antagonist targeting miR-210, a pre-miRNA mimic targeting miR-21, and any combination thereof. In certain embodiments, the kits include systems that allow for the storage, transport, or delivery of reaction reagents, for example, a small RNA and a culture medium, and supporting materials, for example, buffers, written instructions for performing the assay, from one location to another. In some embodiments, the kits can include one or more control reagents, such as a non-chemically modified small RNA or a non-targeting small RNA. In some embodiments, kits comprise a container, such as a box, comprising the reaction reagents and supporting materials. Such contents can be delivered to the intended recipient together or separately.

In some embodiments, the kits can further include instructions for using the components of the kit to practice the methods of the present invention. The instructions can be recorded on a suitable recording medium, for example, paper, plastic, cardboard, or a digital format. In some embodiments, the instructions can be present as a package insert, on the labeling of the container of the kit or components thereof, such as the packaging or sub-packaging of the kit. In some embodiments, the instructions are present as an electronic storage data file present on a suitable computer readable storage medium, for example, a CD-ROM or flash drive. In yet other embodiments, the actual instructions are not present in the kit, but means for obtaining the instructions from a remote source, such as the Internet, are provided. In some examples, the Internet instructions can be accessed from a web address where the instructions can be viewed or downloaded.

A listing of relevant sequences disclosed herein is provided in TABLE 1. Nucleotides preceded by a "d" correspond to 2'-H modified nucleotides. Nucleotides preceded by a "l" correspond to LNA modified nucleotides. Nucleotides preceded by a "f" correspond to 2'-F modified nucleotides. Underlined nucleotides correspond to 2'-O-methyl modified nucleotides. Phosphorothioate linkages are indicated by an asterisk. Nucleotides preceded by an +-sign correspond to nucleotides to which a $C_6$-amine-TexasRed conjugate moiety is attached (dT-C6-NH (Alexa594). /ZEN/ corresponds to an N,N-diethyl-4-(4-nitronaphthalen-1-ylazo)-phenylamine chemical modifier.

SEQ ID NOS: 1 and 2 correspond to DNA sequences encoding transcripts for human and mouse PHD2 transcripts, respectively. SEQ ID NOS: 3 and 4 correspond to sequences for naturally occurring miR-210 and miR-21, respectively. SEQ ID NOS: 44-48 correspond to sequences representing pre-miRNA mimics disclosed herein. SEQ ID NOS: 5-8, 11-27, 30, 31, 49-325 correspond to sequences representing sshRNAs targeting PHD2, disclosed herein. SEQ ID NOS: 32-43, 326-328 correspond to sequences representing miRNA antagonists disclosed herein. SEQ ID NOS: 9, 10, 28, 29 correspond to sequences (guide (g) or passenger (p) strands) that make up siRNA targeting PHD2. For example, SEQ ID NOS: 28 and 29 are the individual strands that make up an siRNA-SG403g is guide (antisense) and SG403p is passenger (sense).

TABLE 1

| SEQ ID NO | Name | Sequence |
|---|---|---|
| 1 | human PHD2 | TTAGGGGCAGAAAAACATTTGTAATAATTAATGGCTTTGAGAGA<br>CACAAGGCTTTGTTTGCCCCAGAGTATTAGTTAACCCACCTAGTG<br>CTCCTAATCATACAATATTAAGGATTGGGAGGGACATTCATTGCC<br>TCACTCTCTATTTGTTTCACCTTCTGTAAAATTGGTAGAATAATA<br>GTACCCACTTCATAGCATTGTATGATGATTAAATTGGTTAATATT<br>TTTAAAATGCTTAGAACACAGATTGGGCACATAACAGCAAGCAC<br>CACATGTGTTTATAAGATAAATTCCTTTGTGTTGCCTTCCGTTAA<br>AGTTTAAATAAGTAAATAAATAAATAAATACTTGCATGACATTTT<br>GAAGTCTCTCTATAACATCTGAGTAAGTGGCGGCTGCGACAATG<br>CTACTGGAGTTCCAGAATCGTGTTGGTGACAAGATTGTTCACCAG<br>CATATGGTGTGGTGAAAACTCACTAATTTGGAATTAGTTCAGATT<br>ATTAAGCCTGAATAGGTGAAAATCCTGAAATCAAGGATCTTTGG<br>AACTATTTGAAATCAGTATTTTATATTTTCCTGTTGTATTCATTAA<br>AGTGTTGCAAGTGTTCTATTTGATGGATTAAGTATATTTAGGATA<br>TACATGTTCAATTTGTGATTTTGTATACTTAATTGGAACAAGAAA<br>GCTAATAAAGGTTTTGATATGGACATCTATTCTTTTAAGTAAACT<br>TCAATGAAAATATATGAGTAGAGCATATAGAGATGTAAATAATT<br>TGTGGACACACCACAGACTGAAATAGCAAATTTAAAAGAAATTG<br>TTGGAAGAATCAAGTGTTTGTGGAATGAGTCCTCCTAGTAAAGTT<br>CCTGCTCTTGTGAATAATTAAGCCTCATGTATAATTACTATAGCA<br>AAAGGAAGCCTAAGAAGTATTAGACTCTACTTGTATTTAAATTAC<br>ATTTTACATAATTTATGTGTATGAAAAATGTTTTAAATGCTTATTT<br>TCGTAAGCCATGAGATAGCTCCTTTATATTTTAAGAATTTCTGAA<br>TTAATTTGCTTGGATTTTATTAGTGCAAATGGCAGAGCTAGCAAT<br>TCCTTTTTCTGTGTTCCCATTCCATCCTATTCATCCCTCTTTTAGG<br>AAACTCTGAACTCTGGATTGTCCTTGTTTACATACCTGCCTCCTG<br>CATTGGACTATGTGTCTCTGAGTGTAGTATGACTAATTCATTTGT<br>TTGTCAAGGACTCTCAATGCATTTGTTGAACAGCCTAATTAGTAA<br>TGTCTGCAACAATGACATTTTACTGTATTTAATAAAGCTCTGGGA<br>AAGTAGGATACACATAAGACAGGTCTAGGTCTAAATTCTTTACA<br>GAAACTTGGATTTTTAGTTCGGTTTGAAATTTGAAGATGTGAGTA<br>TATTTATCTCAGTTTCCCAAAGGACAAGCTAATTGGAATTATCAT<br>CCTCTTTCACTTGATTGGATCCCCAGAATGCCATTTACGCATGCA<br>GCAGGATTTTATAACAGTTTTAAATTCTGTATATTTGATGAAGAG<br>GTTTTATATTTTTGGATTCAAGCCTCTTTTTAAACTTCTACAATAT<br>GGTTTACAATAATTCCTTATATCCTGCTTTTGAAATACATATTAC<br>AACTTTTTAAGTTTGGAAGGCTATATTTCAAGGACTGAAGTTACA<br>GTATACTCAAGTGATACACAAGCCTAGCACCCCACTTTCCACATA<br>GTGTTCGATAAAGATTGATAAACTCGAAATCACAGACCTTTTAAT<br>TCTTAAGACAAATAGCAGCAGAAAGAAACATCTTTGGCTTATTTC<br>TGGTAAGGTTTTTATGCTCTGTAAAACAAAGAATTGTATTCATCC<br>GCGCAGCACAGATTCTATTAAAAATAAATGTGAGAGTCGTTAAT<br>GTAGTACTGCTCATTTACCATCAAAATTCACTTTTCAGGAATAAT<br>CCCATCAGTTTAAATTGGATATTGGAATGAGCATTGATTACATTT<br>AACTTGGTAGCCCAAAATTTCTTCATGGGGTTTTGAACTCGGCGG<br>GATTTCAAAGGTTTTAAAAATGAGTTTTTGATTTTTTTTAAAACC<br>CTCAAATTTCATTACCTTTAAACTAGGTCGAAACGGGGCGCAAG<br>AGATTGGATTAACACCATAGTAATACTTATTTTGTTCTTAACCAT<br>TTCAGGGCTTCTTGAAATAGAGGCTGTATGGTGTAATGGAAAAA<br>ACAGCCTTGGAATCTGGGAGCCTGATTCCTGGATTCAGTCCCAGT<br>TTTGCGTGACCTTGGGCAAGTTACTTTACTTCTCTGAATTTCCGTT<br>TCCTCCTCTGCAAAATGAGGATCGCAATAGCCACCTTGCAACCTT<br>GACTGGAGCGAGCCTCGCACACCCCGCGCCGGCCTGGAGGAAGA<br>GCAGCCATGATTACGCCGCCTTCGCTCCGCTACCCGCTTGCGGCT<br>GGCGCCCTCCTCCAGCAGGTGTAGGCGCTGCCGCGCTGCCCCAC<br>GCCTTTCCGCCGCTCGCGGGCCTGCGCCTCGGCGTCCCCGAGGAG<br>GCCGCTGCGGGCTGAGGTAGCGCACCGGCCTCTCGGCGTCCCAG<br>TCCGGTCCCGGGCGGAGGGAAAGCGGGCGACCCACCTCCGAGGC<br>AGAAGCCGAGGCCCGGCCCCGCCGAGTGCGGAGGAGCGCAGGC<br>AGCCCCGCCCCTCGGCCCTCCCCCCGGCCCTCCCGGCCCTCCCT<br>CCGCCCCCTCCGCCCTCGCGCGCCGCCCGCCCGGGTCGCCGCGG<br>GGCCGTGGTGTACGTGCAGAGCGCGCAGAGCGAGTGGCGCCCGT<br>ATGCCCTGCGCTCCTCCACAGCCTGGGCCGGGCCGCCCGGGACG<br>CTGAGGCGGCGGCGGCGGCCGAGGGGGCCGGTCTTGCGCTCCCC<br>AGGCCCGCGCGCCTGAGCCCAGGTTGCCATTCGCCGCACAGGCC |

TABLE 1-continued

| SEQ ID NO | Name | Sequence |
|---|---|---|
| | | CTATTCTCTCAGCCCTCGGCGGCGATGAGGCGCTGAGGCGGCTG |
| | | CCGGCGCTGCGCCGGAGCTTAGGACTCGGAAGCGGCCGGGCCGA |
| | | GGGCGTGGGGTGCCGGCCTCCCTGAGGCGAGGGTAGCGGGTGCA |
| | | TGGCGCAGTAACGGCCCCTATCTCTCTCCCCGCTCCCCAGCCTCG |
| | | GGCGAGGCCGTCCGGCCGCTACCCCTCCTGCTCGGCCGCCGCAG |
| | | TCGCCGTCGCCGCCGCCGCCGCCGCCATGGCCAATGACAGCGGC |
| | | GGGCCCGGCGGGCCGAGCCCGAGCGAGCGAGACCGGCAGTACT |
| | | GCGAGCTGTGCGGGAAGATGGAGAACCTGCTGCGCTGCAGCCGC |
| | | TGCCGCAGCTCCTTCTACTGCTGCAAGGAGCACCAGCGTCAGGA |
| | | CTGGAAGAAGCACAAGCTCGTGTGCCAGGGCAGCGAGGGCGCCC |
| | | TCGGCCACGGAGTGGGCCCACACCAGCATTCCGGCCCCGCGCCG |
| | | CCGGCTGCAGTGCCGCCGCCCAGGGCCGGGGCCCGGGAGCCCAG |
| | | GAAGGCAGCGGCGCGCCGGGACAACGCCTCCGGGGACGCGGCC |
| | | AAGGGAAAAGTAAAGGCCAAGCCCCCGGCCGACCCAGCGGCGG |
| | | CCGCGTCGCCGTGTCGTGCGGCCGCCGGCGGCCAGGGCTCGGCG |
| | | GTGGCTGCCGAAGCCGAGCCCGGCAAGGAGGAGCCGCCGGCCC |
| | | GCTCATCGCTGTTCCAGGAGAAGGCGAACCTGTACCCCCCAAGC |
| | | AACACGCCCGGGGATGCGCTGAGCCCCGGCGGCGGCCTGCGGCC |
| | | CAACGGGCAGACGAAGCCCCTGCCGGCGCTGAAGCTGGCGCTCG |
| | | AGTACATCGTGCCGTGCATGAACAAGCACGGCATCTGTGTGGTG |
| | | GACGACTTCCTCGGCAAGGAGACCGGACAGCAGATCGGCGACGA |
| | | GGTGCGCGCCCTGCACGACACCGGGAAGTTCACGGACGGGCAGC |
| | | TGGTCAGCCAGAAGAGTGACTCGTCCAAGGACATCCGAGGCGAT |
| | | AAGATCACCTGGATCGAGGGCAAGGAGCCCGGCTGCGAAACCAT |
| | | TGGGCTGCTCATGAGCAGCATGGACGACCTGATACGCCACTGTA |
| | | ACGGGAAGCTGGGCAGCTACAAAATCAATGGCCGGACGAAAGC |
| | | CATGGTTGCTTGTTATCCGGGCAATGGAACGGGTTATGTACGTCA |
| | | TGTTGATAATCCAAATGGAGATGGAAGATGTGTGACATGTATAT |
| | | ATTATCTTAATAAAGACTGGGATGCCAAGGTAAGTGGAGGTATA |
| | | CTTCGAATTTTTCCAGAAGGCAAAGCCCAGTTTGCTGACATTGAA |
| | | CCCAAATTTGATAGACTGCTGTTTTTTCTGGTCTGACCGTCGCAAC |
| | | CCTCATGAAGTACAACCAGCATATGCTACAAGGTACGCAATAAC |
| | | TGTTTGGTATTTTGATGCAGATGAGAGAGCACGAGCTAAAGTAA |
| | | AATATCTAACAGGTGAAAAAGGTGTGAGGGTTGAACTCAATAAA |
| | | CCTTCAGATTCGGTCGGTAAAGACGTCTTCTAGAGCCTTTGATCC |
| | | AGCAATACCCCACTTCACCTACAATATTGTTAACTATTTGTTAAC |
| | | TTGTGAATACGAATAAATGGGATAAAGAAAAATAGACAACCAGT |
| | | TCGCATTTTAATAAGGAAACAGAAACAACTTTTTGTGTTGCATCA |
| | | AACAGAAGATTTTGACTGCTGTGACTTTGTACTGCATGATCAACT |
| | | TCAAATCTGTGATTGCTTACAGGAGGAAGATAAGCTACTAATTG |
| | | AAAATGGTTTTTACATCTGGATATGAAATAAGTGCCCTGTGTAGA |
| | | ATTTTTTTCATTCTTATATTTTGCCAGATCTGTTATCTAGCTGAGT |
| | | TCATTTCATCTCTCCCTTTTTTATATCAAGTTTGAATTTGGGATAA |
| | | TTTTTCTATATTAGGTACAATTTATCTAAACTGAATTGAGAAAAA |
| | | ATTACAGTATTATTCCTCAAAATAACATCAATCTATTTTTGTAAA |
| | | CCTGTTCATACTATTAAATTTTGCCCTAAAAGACCTCTTAATAAT |
| | | GATTGTTGCCAGTGACTGATGATTAATTTTATTTTACTTAAAATA |
| | | AGAAAAGGAGCACTTTAATTACAACTGAAAAATCAGATTGTTTT |
| | | GTAGTCCTTCCTTACACTAATTTGAACTGTTAAAGATTGCTGCTTT |
| | | TTTTTTGACATTGTCAATAACGAAACCTAATTGTAAAACAGTCAC |
| | | CATTTACTACCAATAACTTTTAGTTAATGTTTTACAAGGAAAAAG |
| | | ACACAAGAAGAGTTTAAATTTTTTTGTTTTGTTTTGTTTTTTTGAG |
| | | ACAGTCTTGCTCTGTTACCCAGGCTGGAGGGGAGTGGTGCATTCT |
| | | TGGCTCACTGCAACCTCCGCCTCCCAGGTTCAAGCAATCCTCCCA |
| | | CCTCAGCCTCCCAACTAGCTGGGACTGCAGGCACACACCACCAT |
| | | GCCTGACTAATTTTTGTATGTTTAGTAGAGACGGGGTTTTGCCAT |
| | | GTTGCCTAGGCTGGGGTTTAAGTTAAATTTTTTAAAAAACTAAAG |
| | | TGACTGGCACTAAGTGAACTTGAGATTATCCTCAGCTTCAAGTTC |
| | | CTAAGATAAGGGCTTTCTTAAGCTTTCAGGTGTATGTATCCTCTA |
| | | GATGTAGACAATAATGTCCCATTTCTAAGTCTTTTCCTTTTGCTTC |
| | | TCCTTAAATTGATTGTACTTCCAAATTTGCTGTTATGTTTTTTTCC |
| | | TAATACTGTGATCTATCTGATCTGCAGACAAGAACCTTGTCTCTG |
| | | TTGAAGAGCATCAAGGGGAGATTATGTACACATTGAAACTGAAG |
| | | TGTGGTGTTACTGACGGAATGTGCAGTAACTCCTCAGATATCTGT |
| | | TAAGGCATTTCCCAGATGTGATGCCAGCCTTCTTACCTGTACTGA |
| | | AAGATGCTTAGCTTAGAAAAAAACAAAACAGATGCAAAATCAG |
| | | ATAATTTTATTTTGTTTCATGGGTTTTCTTATTTACTTTTTAAACA |
| | | AGGAAGGAATATTAGAAAATCACACAAGGCCTCACATACATGTT |
| | | ATTTAAAGAATGAATTGGGACGGATGTCTTAGACTTCACTTTCCT |
| | | AGGCTTTTTAGCAAAACCTAAAGGGTGGTATCCATATTTTGCGTG |
| | | AATTATGGGTGTAAGACCTTGCCCACTTAGGTTTTCTATCTCTGT |
| | | CCTTGATCTTCTTTGCCAAAATGTGAGTATACAGAAATTTTCTGT |
| | | ATATTTCAACTTAAGACATTTTTAGCATCTGTATAGTTTGTATTCA |
| | | ATTTGAGACCTTTTCTATGGGAAGCTCAGTAATTTTTATTAAAAG |
| | | ATTGCCATTGCTATTCATGTAAAACATGGAAAAAATTGTGTAGT |
| | | GAAGCCAACAGTGGACTTAGGATGGGATTGAATGTTCAGTATAG |
| | | TGATCTCACTTAGGAGAATTTGCAGGAGAAAGTGATAGTTTATTG |
| | | TTTTTTCCTCGCCCATATTCAGTTTTGTTCTACTTCCTCCCCTTCCT |

TABLE 1-continued

| SEQ ID NO | Name | Sequence |
|---|---|---|
| | | TCCAGATGATAACATCACATCTCTACAGTAAGTGCCTCTGCCAGC<br>CCAACCCAGGAGCGCAAGTTGTCTTTGCCATCTGGTCTATAGTAC<br>AGTGCGCGGCGTTAGGCCACAACTCAAAAGCATTATCTTTTTTAG<br>GGTTAGTAGAAATTGTTTTATGTTGATGGGAGGTTTGTTTGATTG<br>TCAAAATGTACAGCCACAGCCTTTTAATTTGGGAGCCCCTGTTGT<br>CATTCAAATGTGTACCTCTACAGTTGTAAAAAGTATTAGATTCTA<br>CTATCTGTGGGTTGTGCTTGCCAGACAGGTCTTAAATTGTATATT<br>TTTTGGAAAAGTTTATATACTCTCTTAGGAATCATTGTGAAAAGA<br>TCAAGAAATCAGGATGGCCATTTATTTAATATCCATTCATTTCAT<br>GTTAGTGGGACTATTAACTTGTCACCAAGCAGGACTCTATTTCAA<br>ACAAAATTTAAAACTGTTTGTGGCCTATATGTGTTTAATCCTGGT<br>TAAAGATAAAGCTTCATAATGCTGTTTTTATTCAACACATTAACC<br>AGCTGTAAAACACAGACCTTTATCAAGAGTAGGCAAAGATTTTC<br>AGGATTCATATACAGATAGACTATAAAGTCATGTAATTTGAAAA<br>GCAGTGTTTCATTATGAAAGAGCTCTCAAGTTGCTTGTAAAGCTA<br>ATCTAATTAAAAAGATGTATAAATGTTGTTGAAACATTAAAAAA |
| 2 | mouse<br>PHD2 | GGCTGGGCCCGCCCGCCCAGGGCGCTGTGCGCCGCGCAGGCCGC<br>GCTCTCTCCGGCGCGATGCGGCGCTAGGCGGCCCCGGGCAAGGC<br>AGGCGAGGCCAGGGCGCGCGCGGCCTCCCGCAGCGGGCGGCGG<br>CCCCGGGCGGGCGCCCCGACGGCCCCGCCGCCGCCCCGCTCCCG<br>GCCCGCGGCCCGCCCTGCCGCGGCCATGGCCAGTGACAGCGGCG<br>GGCCCGGCGTGCTGAGCGCCAGCGAGCGCGACCGGCAGTACTGC<br>GAGCTGTGCGGGAAGATGGAGAACCTGCTGCGCTGCGGCCGCTG<br>CCGCAGCTCCTTCTACTGCTGCAAAGAGCACCAGCGCCAGGACT<br>GGAAGAAGCACAAGCTGGTGTGCCAGGGCGGCGAGGCCCCCCG<br>CGCGCAGCCCGCGCCGGCGCAGCCCCGCGTCGCGCCCCCGCCCG<br>GTGGGGCCCCGGAGCCGCGCGCGCCGGCGGGGCGGCCCGGCGC<br>GGGGACAGCGCGGCGGCCTCGCGCGTACCGGGCCCGGAGGACG<br>CGGCGCAGGCCGGAGCGGCCCCGGCCCAGCAGAGCCCGGCTCC<br>GAGGATCCTCCGCTTAGCCGGTCTCCGGGCCCCGAGCGCGCCAG<br>CCTGTGCCCAGCGGGTGGCGGCCCCGGGGAGGCGCTGAGTCCCG<br>GTGGAGGGCTGCGGCCCAACGGGCAGACCAAGCCGTTGCCCGCG<br>TTGAAGCTGGCTCTGGAGTACATCGTGCCGTGCATGAACAAGCA<br>CGGCATCTGCGTGGTGGACGACTTCCTGGGCAGGGAGACCGGGC<br>AGCAGATCGGCGATGAGGTGCGCGCCCTGCACGACACCGGCAAG<br>TTCACGGACGGGCAGCTGGTCAGCCAGAAGAGTGACTCTTCCAA<br>GGACATCCGGGGGGACCAGATCACCTGGATCGAGGGCAAAGAG<br>CCCGGCTGCGAAACCATCGGCCTGCTCATGAGCAGCATGGACGA<br>CCTGATCCGCCACTGCAGCGGGAAGCTGGGCAACTACAGGATAA<br>ACGGCCGAACGAAAGCCATGGTTGCTTGTTACCCAGGCAACGGA<br>ACAGGCTATGTCCGTCACGTTGATAACCCAAATGGAGATGGAAG<br>ATGCGTGACATGTATATATTATCTAAATAAAGACTGGGACGCCA<br>AGGTAAGTGGAGGTATTCTTCGAATTTTTCCAGAAGGCAAAGCC<br>CAGTTTGCTGACATTGAACCCAAATTTGATAGACTGCTGTTTTTC<br>TGGTCTGACCGGCGTAACCCTCATGAAGTACAGCCAGCATACGC<br>CACAAGGTACGCAATAACTGTTTGGTATTTTGATGCAGATGAGC<br>GAGCGAGAGCTAAAGTAAAATATCTAACAGGTGAGAAAGGTGT<br>GAGGGTTGAACTCAAGCCCAATTCAGTCAGCAAAGACGTCTAGT<br>GGGGCCTTGGGTCCGGCAGTACCCACGTCACCTACAGCCTCTCA<br>GTTGCCTTCTGTGGACTCGTGGACAGGATGGACAGAGAGACACC<br>TGCCTGGTATTTCAGCTGGGAGCCAGGCGACTTCGCGGGTGTCA<br>TCCAACAGAGGGCTCCATCTGCTGGGACTGTACTGTGGGGTCAG<br>CTCCAGATCTGTGACTGCTCTTGGCTGCTGACCAAGAGGAGAC<br>GCTGTCGGAGGAGAGTAGCTTTTCCATCTGGACACGAAACAAGG<br>GCCCTTTGTAGGAATTTCTTCAGTCTTCTATTTTGCCAGACCTGTC<br>ACCTAACTGAGTTCATTTCATCTCTTTTTTATATCAAGTTTTGAAT<br>TCGGGGAATTTTTGTATTAGGTACAATTTATCAAAACTGAATTAA<br>GAAAAAAAAATTTACAGTATTATTCTCAAAATAACATCAATCTAT<br>TTTTGTAAACCTCTTCATGCTATTAAATTTTGCCCTCAAGGCCTCC<br>TGCGATGATTGTTGCCAGTGAGTGACGACGTGTTGCTTCTGCCTG<br>AACGTAAAGGACGGGCGGGCGCTGTGTCCCAGCCCGAGTGCACG<br>AGGTTTTTCTTGGCCCGTCTCTCAGTGATTCCAACCTGTAAAGGT<br>CACTGCTCTCGCGCTTCGACCGACCTAACAGTAGATGGTTGCCAC<br>TGGCACTCAACTAACTCAACATAGTTACAAGAGGAAACAAGCCA<br>CAGGAGAGGGTTTGTCTCTTCAGTTAATTTTTTAAAGCGAAGTG<br>ACGGGCACTAAATGAACTCGGGGCTCTCCCTCAGCTTCGGGTTCC<br>TGAGACAAAGGGCTTTCTTCTGCGGCAGGTCTAGCCTGCCTACAG<br>CCGTGTCCCACTGCCGCAGGTTTCCTTGTGGCTTCTCCGTAGTTTT<br>GACTGTGCTTCCAGACCCTTCCAGGTCAGGGCTGTGTTCTTGTGG<br>CAGGGCACCTGGTGGACCCAGGCACGTGAATGTGGTATGTGGTT<br>GTAGCCTCAATCGTGGCCATCGGCTCCTTGGACAGCCACGAGCC<br>ATTTTCATACCCAATAATGAAAGCTGTGTGCTAGCTTAGAAATCA<br>AAGGGGGTGTAAAAGCACACATTCTTTGTTTTATGGGTTTTTCTC<br>TTTTTTAGAGGACAGAGGGACAACCACACGAGGCTGCCAGACTCC<br>TGTCACCTCTACAGTCCCCTTAGAAAGCCAGAGTTTGCACAGATT<br>GTGGGTATAACTCCTGTCCCCTTAGGTGTTCTATCTCCGACCTTG<br>ATCTTTGCCAAAATGTGTGTATGCAGAACTATTTCTGTGTATTTTC |

TABLE 1-continued

| SEQ ID NO | Name | Sequence |
|---|---|---|
| | | CTTGACACCCGTCTTAGCACCTGTGTAGTTTGTATCCGGTTAGAA<br>ACCTTTTCTATGGAAAGCTCAGTAATTCTTATTAAGAGATTGCTA<br>TTGTTCATGTAAAACATGAAAACAACCAAGTAGAGCCGTGTGTG<br>GATGAGGGCCCACTCAGCACTGTGCTTGCTTGAGGGGCTCTCGG<br>CAGGAAGTCTCCTTCTGACCCATATCCGCTGACCACACCTCTCCA<br>GCAAGTGCCTCTGCCGCTGGCCAGCTCAAGGTTTGCCCACCTGGC<br>CCCGAAGCACCGTGTTTCGGAGTTGGGAGGAACTGTTTGGCATT<br>GTTGGCAGAAGGTGTGATTGCCTGGAGCAGCAGCCTTTTAAATTC<br>TGGAGACCCTGTAGTCCTTTGTATCTCAGACCTTTACTGATGTAC<br>CAGGTCCCAGATTCTGTGGCAGGGGATGGGGTGGGGTGTGCTTG<br>CCAGACGAAATTTAAATTATCTATCTTTTGGGAAGTGTGTGCTTT<br>CCTGGAGGTCACTGTGAAAACAAACAAACAAATCAGGACCGTTA<br>ACCCCTTAATGCCCACTTAAACTCAATTTCATGTTAGGACTCTTG<br>TTTAAAACCATTTGTGGCCTGTATGTGTTCATCCTGGTTAGAGAG<br>AAAGCTTTATGACGCTGTTTCTGTTCAACACATTAACCAGCTGTG<br>GAACAGCCCTTTTTGCACGACAGGCAGGGCACTTCAGGATTCGC<br>AGAGAGACTCGTGTGGTTTGGAAGTGGTATTTCCTATGAAAGCCT<br>CTCACGTTGCTTGTAAAGCTAATCTAATTAAAAAGATGTATAAAT<br>GTTCTTGAAAAAAATC |
| 3 | miR-<br>210 | CUGUGCGUGUGACAGCGGCUGA |
| 4 | miR-<br>21 | UAGCUUAUCAGACUGAUGUUGA |
| 5 | SG300 | CUUCCUUUGCUAUAGUAAUUUUACUAUAGCAAAAGGAAGUU |
| 6 | SG301 | UGUUGCAGACAUUACUAAUUUAUUAGUAAUGUCUGCAACAUU |
| 7 | SG302 | UAUACCUCCACUUACCUUGUUCAAGGUAAGUGGAGGUAUAUU |
| 8 | SG302<br>m1 | UAUACCUCCACUUACCUUGUUCAAGGUAAGUGGAGGUAUAUU |
| 9 | SG303<br>g | UAUACCUCCACUUACCUUGUU |
| 10 | SG303<br>p | CAAGGUAAGUGGAGGUAUAUU |
| 11 | SG304 | AUUCGAAGUAUACCUCCACUUGUGGAGGUAUACUUCGAAUUU |
| 12 | SG305 | CGAAGUAUACCUCCACUUAUUUAAGUGGAGGUAUACUUCGUU |
| 13 | SG306 | AGUAUACCUCCACUUACCUUUAGGUAAGUGGAGGUAUACUUU |
| 14 | SG307 | UACCUCCACUUACCUUGGCUUGCCAAGGUAAGUGGAGGUAUU |
| 15 | SG308 | CUCCACUUACCUUGGCAUCUUGAUGCCAAGGUAAGUGGAGUU |
| 16 | SG309 | CACUUACCUUGGCAUCCCAUUUGGGAUGCCAAGGUAAGUGUU |
| 17 | SG310 | AGGUUCUCCAUCUUCCCGCUUGCGGGAAGAUGGAGAACCUUU |
| 18 | SG311 | AUGCCGUGCUUGUUCAUGCUUGCAUGAACAAGCACGGCAUUU |
| 19 | SG312 | UCACUCUUCUGGCUGACCAUUUGGUCAGCCAGAAGAGUGAUU |
| 20 | SG313 | AUCUUCCAUCUCCAUUUGGUUCCAAAUGGAGAUGGAAGAUUU |
| 21 | SG314 | UGUGCUUCUUCCAGUCCUGUUCAGGACUGGAAGAAGCACAUU |
| 22 | SG315 | AUCAGGUCGUCCAUGCUGCUUGCAGCAUGGACGACCUGAUUU |
| 23 | SG316 | AUACCUCCACUUACCUUGgUUcCAAGGUAAGUGGAGGUAUUU |
| 24 | SG400 | UGGCGUAUGCUGGCUGUACUUGUACAGCCAGCAUACGCCAUU |
| 25 | SG401 | CUCACACCUUUCUCACCUGUUCAGGUGAGAAAGGUGUGAGUU |
| 26 | SG402 | CUGAAUUGGGCUUGAGUUCUUGAACUCAAGCCCAAUUCAGUU |
| 27 | SG402<br>m1 | CUGAAUUGGGCUUGAGUUCUUGAACUCAAGCCCAAUUCAGTT |
| 28 | SG403<br>p | GAACUCAAGCCCAAUUCAGUU |

TABLE 1-continued

| SEQ ID NO | Name | Sequence |
|---|---|---|
| 29 | SG403g | CUGAAUUGGGCUUGAGUUCUU |
| 30 | SG404 | CUGAAUUGGGCUUGAGUUCUUGAACUCAAGCCCAAUUCAG |
| 31 | SG405 | CUGAAUUGGGCUUGAGUUC + TUGAACUCAAGCCCAAUUCAG |
| 32 | SG601 | UCAGCCGCUGUCACACGCACAG |
| 33 | SG602 | dTdCdAdGdCdCdGdCdTdGdTdCdAdCdAdCdGdCdAdCdAdG |
| 34 | SG603 | UCAGCCGCUGUCACACGCACAG |
| 35 | SG604 | GCCGCTGTCACACGCACA |
| 36 | SG605 | AGAGCTCCCTTCAATCCAAA |
| 37 | SG613 | U1CA1GC1CG1CU1GUCACA1CG1CA1CA1G |
| 38 | SG614 | U1CAfGC1CGfCU1GUCACA1CGfCA1CAfG |
| 39 | SG608 | UfCAfGCfCGfCUfGUCACAfCGfCAfCAfG |
| 40 | SG609 | UCAfGCCGfCUGUCACACGfCACAfG |
| 41 | SG610 | UCAGCCGCUGUCACACGCACAG |
| 42 | SG611 | U1CA1GC1CG1CU1GU1C1A1CA1CG1CA1CA1G |
| 43 | SG612 | UfCAfGCfCGfCUfGUfCfAfCAfCGfCAfCAfG |
| 44 | SG701 | UAGCUUAUCAGACUGAUGUUGACUGUUGAAUCUCAUGGCAACACCAGUCGAUGGGCUUU |
| 45 | SG702 | UAGCUUAUCAGACUGAUGUUGACAUCAGUCUGAUAAGCUC |
| 46 | SG703 | UAGCUUAUCAGACUGAUGUUGACAUCAGUCUGAUAAGCUAUU |
| 47 | SG704 | UAGCUUAUCAGACUGAUGUUGAUUUCAACAUCAGUCUGAUAAGCUAUU |
| 48 | SG705 | UAGCUUAUCAGACUGAUGUUGAUUUCAACAUCAGUCUGAUAAGCUAUU |
| 49 | PHD2-17 | CCGGGCCCGCCGCUGUCAUUUAUGACAGCGGCGGGCCCGGUU |
| 50 | PHD2-18 | GCCGGGCCCGCCGCUGUCAUUUGACAGCGGCGGGCCCGGCUU |
| 51 | PHD2-19 | CGCCGGGCCCGCCGCUGUCUUGACAGCGGCGGGCCCGGCGUU |
| 52 | PHD2-20 | CCGCCGGGCCCGCCGCUGUUUACAGCGGCGGGCCCGGCGGUU |
| 53 | PHD2-21 | CUCGCAGUACUGCCGGUCUUUAGACCGGCAGUACUGCGAGUU |
| 54 | PHD2-22 | GCUCGCAGUACUGCCGGUCUUGACCGGCAGUACUGCGAGCUU |
| 55 | PHD2-23 | AGCUCGCAGUACUGCCGGUUUACCGGCAGUACUGCGAGCUUU |
| 56 | PHD2-24 | CAGCUCGCAGUACUGCCGGUUCCGGCAGUACUGCGAGCUGUU |
| 57 | PHD2-25 | ACAGCUCGCAGUACUGCCGUUCGGCAGUACUGCGAGCUGUUU |
| 58 | PHD2-26 | CACAGCUCGCAGUACUGCCUUGGCAGUACUGCGAGCUGUGUU |
| 59 | PHD2-27 | GCACAGCUCGCAGUACUGCUUGCAGUACUGCGAGCUGUGCUU |

TABLE 1-continued

| SEQ ID NO | Name | Sequence |
|---|---|---|
| 60 | PHD2-28 | CGCACAGCUCGCAGUACUGUUCAGUACUGCGAGCUGUGCGUU |
| 61 | PHD2-29 | CCGCACAGCUCGCAGUACUUUAGUACUGCGAGCUGUGCGGUU |
| 62 | PHD2-30 | CCCGCACAGCUCGCAGUACUUGUACUGCGAGCUGUGCGGGUU |
| 63 | PHD2-31 | UCCCGCACAGCUCGCAGUAUUUACUGCGAGCUGUGCGGGAUU |
| 64 | PHD2-32 | UUCCCGCACAGCUCGCAGUUUACUGCGAGCUGUGCGGGAAUU |
| 65 | PHD2-33 | CUUCCCGCACAGCUCGCAGUUCUGCGAGCUGUGCGGGAAGUU |
| 66 | PHD2-34 | UCUUCCCGCACAGCUCGCAUUUGCGAGCUGUGCGGGAAGAUU |
| 67 | PHD2-35 | AUCUUCCCGCACAGCUCGCUUGCGAGCUGUGCGGGAAGAUUU |
| 68 | PHD2-36 | CAUCUUCCCGCACAGCUCGUUCGAGCUGUGCGGGAAGAUGUU |
| 69 | PHD2-37 | CCAUCUUCCCGCACAGCUCUUGAGCUGUGCGGGAAGAUGGUU |
| 70 | PHD2-38 | UCCAUCUUCCCGCACAGCUUUAGCUGUGCGGGAAGAUGGAUU |
| 71 | PHD2-39 | CUCCAUCUUCCCGCACAGCUUGCUGUGCGGGAAGAUGGAGUU |
| 72 | PHD2-40 | UCUCCAUCUUCCCGCACAGUUCUGUGCGGGAAGAUGGAGAUU |
| 73 | PHD2-41 | UUCUCCAUCUUCCCGCACAUUUGUGCGGGAAGAUGGAGAAUU |
| 74 | PHD2-42 | GUUCUCCAUCUUCCCGCACUUGUGCGGGAAGAUGGAGAACUU |
| 75 | PHD2-43 | GGUUCUCCAUCUUCCCGCAUUUGCGGGAAGAUGGAGAACCUU |
| 76 | PHD2-44 | AGGUUCUCCAUCUUCCCGCUUGCGGGAAGAUGGAGAACCUUU |
| 77 | PHD2-45 | CAGGUUCUCCAUCUUCCCGUUCGGGAAGAUGGAGAACCUGUU |
| 78 | PHD2-46 | GCAGGUUCUCCAUCUUCCCUUGGGAAGAUGGAGAACCUGCUU |
| 79 | PHD2-47 | AGCAGGUUCUCCAUCUUCCUUGGAAGAUGGAGAACCUGCUUU |
| 80 | PHD2-48 | CAGCAGGUUCUCCAUCUUCUUGAAGAUGGAGAACCUGCUGUU |
| 81 | PHD2-49 | GCAGCAGGUUCUCCAUCUUUUAAGAUGGAGAACCUGCUGCUU |
| 82 | PHD2-50 | CGCAGCAGGUUCUCCAUCUUUAGAUGGAGAACCUGCUGCGUU |
| 83 | PHD2-51 | GCGCAGCAGGUUCUCCAUCUUGAUGGAGAACCUGCUGCGCUU |
| 84 | PHD2-52 | AGCGCAGCAGGUUCUCCAUUUAUGGAGAACCUGCUGCGCUUU |
| 85 | PHD2-53 | CAGCGCAGCAGGUUCUCCAUUUGGAGAACCUGCUGCGCUGUU |

TABLE 1-continued

| SEQ ID NO | Name | Sequence |
|---|---|---|
| 86 | PHD2-54 | GCAGCGCAGCAGGUUCUCCUUGGAGAACCUGCUGCGCUGCUU |
| 87 | PHD2-55 | UGCAGCGCAGCAGGUUCUCUUGAGAACCUGCUGCGCUGCAUU |
| 88 | PHD2-56 | AGGAGCUGCGGCAGCGGCUUUAGCCGCUGCCGCAGCUCCUUU |
| 89 | PHD2-57 | AAGGAGCUGCGGCAGCGGCUUGCCGCUGCCGCAGCUCCUUUU |
| 90 | PHD2-58 | GAAGGAGCUGCGGCAGCGGUUCCGCUGCCGCAGCUCCUUCUU |
| 91 | PHD2-59 | AGAAGGAGCUGCGGCAGCGUUCGCUGCCGCAGCUCCUUCUUU |
| 92 | PHD2-60 | UAGAAGGAGCUGCGGCAGCUUGCUGCCGCAGCUCCUUCUAUU |
| 93 | PHD2-61 | GUAGAAGGAGCUGCGGCAGUUCUGCCGCAGCUCCUUCUACUU |
| 94 | PHD2-62 | AGUAGAAGGAGCUGCGGCAUUUGCCGCAGCUCCUUCUACUUU |
| 95 | PHD2-63 | CAGUAGAAGGAGCUGCGGCUUGCCGCAGCUCCUUCUACUGUU |
| 96 | PHD2-64 | GCAGUAGAAGGAGCUGCGGUUCCGCAGCUCCUUCUACUGCUU |
| 97 | PHD2-65 | AGCAGUAGAAGGAGCUGCGUUCGCAGCUCCUUCUACUGCUUU |
| 98 | PHD2-66 | CAGCAGUAGAAGGAGCUGCUUGCAGCUCCUUCUACUGCUGUU |
| 99 | PHD2-67 | GCAGCAGUAGAAGGAGCUGUUCAGCUCCUUCUACUGCUGCUU |
| 100 | PHD2-68 | UGCAGCAGUAGAAGGAGCUUUUAGCUCCUUCUACUGCUGCAUU |
| 101 | PHD2-69 | UUGCAGCAGUAGAAGGAGCUUGCUCCUUCUACUGCUGCAAUU |
| 102 | PHD2-70 | CUUGCAGCAGUAGAAGGAGUUCUCCUUCUACUGCUGCAAGUU |
| 103 | PHD2-71 | GUGCUUCUUCCAGUCCUGAUUUCAGGACUGGAAGAAGCACUU |
| 104 | PHD2-72 | UGUGCUUCUUCCAGUCCUGUUCAGGACUGGAAGAAGCACAUU |
| 105 | PHD2-73 | UUGUGCUUCUUCCAGUCCUUUAGGACUGGAAGAAGCACAAUU |
| 106 | PHD2-74 | CUUGUGCUUCUUCCAGUCCUUGGACUGGAAGAAGCACAAGUU |
| 107 | PHD2-75 | GCUUGUGCUUCUUCCAGUCUUGACUGGAAGAAGCACAAGCUU |
| 108 | PHD2-76 | AGCUUGUGCUUCUUCCAGUUUACUGGAAGAAGCACAAGCUUU |
| 109 | PHD2-77 | GAGCUUGUGCUUCUUCCAGUUCUGGAAGAAGCACAAGCUCUU |
| 110 | PHD2-78 | CUGCCCGUUGGGCCGCAGGUUCCUGCGGCCCAACGGGCAGUU |
| 111 | PHD2-79 | UCUGCCCGUUGGGCCGCAGUUCUGCGGCCCAACGGGCAGAUU |

TABLE 1-continued

| SEQ ID NO | Name | Sequence |
|---|---|---|
| 112 | PHD2-80 | GUCUGCCCGUUGGGCCGCAUUUGCGGCCCAACGGGCAGACUU |
| 113 | PHD2-81 | CGUCUGCCCGUUGGGCCGCUUGCGGCCCAACGGGCAGACGUU |
| 114 | PHD2-82 | GCACGGCACGAUGUACUCGUUCGAGUACAUCGUGCCGUGCUU |
| 115 | PHD2-83 | UGCACGGCACGAUGUACUCUUGAGUACAUCGUGCCGUGCAUU |
| 116 | PHD2-84 | AUGCACGGCACGAUGUACUUUAGUACAUCGUGCCGUGCAUUU |
| 117 | PHD2-85 | CAUGCACGGCACGAUGUACUUGUACAUCGUGCCGUGCAUGUU |
| 118 | PHD2-86 | UCAUGCACGGCACGAUGUAUUUACAUCGUGCCGUGCAUGAUU |
| 119 | PHD2-87 | UUCAUGCACGGCACGAUGUUUACAUCGUGCCGUGCAUGAAUU |
| 120 | PHD2-88 | GUUCAUGCACGGCACGAUGUUCAUCGUGCCGUGCAUGAACUU |
| 121 | PHD2-89 | UGUUCAUGCACGGCACGAUUUAUCGUGCCGUGCAUGAACAUU |
| 122 | PHD2-90 | UUGUUCAUGCACGGCACGAUUUCGUGCCGUGCAUGAACAAUU |
| 123 | PHD2-91 | CUUGUUCAUGCACGGCACGUUCGUGCCGUGCAUGAACAAGUU |
| 124 | PHD2-92 | GCUUGUUCAUGCACGGCACUUGUGCCGUGCAUGAACAAGCUU |
| 125 | PHD2-93 | UGCUUGUUCAUGCACGGCAUUUGCCGUGCAUGAACAAGCAUU |
| 126 | PHD2-94 | GUGCUUGUUCAUGCACGGCUUGCCGUGCAUGAACAAGCACUU |
| 127 | PHD2-95 | CGUGCUUGUUCAUGCACGGUUCCGUGCAUGAACAAGCACGUU |
| 128 | PHD2-96 | CCGUGCUUGUUCAUGCACGUUCGUGCAUGAACAAGCACGGUU |
| 129 | PHD2-97 | GCCGUGCUUGUUCAUGCACUUGUGCAUGAACAAGCACGGCUU |
| 130 | PHD2-98 | UGCCGUGCUUGUUCAUGCAUUUGCAUGAACAAGCACGGCAUU |
| 131 | PHD2-99 | AUGCCGUGCUUGUUCAUGCUUGCAUGAACAAGCACGGCAUUU |
| 132 | PHD2-100 | GAUGCCGUGCUUGUUCAUGUUCAUGAACAAGCACGGCAUCUU |
| 133 | PHD2-101 | AGAUGCCGUGCUUGUUCAUUUAUGAACAAGCACGGCAUCUUU |
| 134 | PHD2-102 | CAGAUGCCGUGCUUGUUCAUUUGAACAAGCACGGCAUCUGUU |
| 135 | PHD2-103 | ACAGAUGCCGUGCUUGUUCUUGAACAAGCACGGCAUCUGUUU |
| 136 | PHD2-104 | GUGCAGGGCGCGCACCUCGUUCGAGGUGCGCGCCCUGCACUU |
| 137 | PHD2-105 | CGUGCAGGGCGCGCACCUCUUGAGGUGCGCGCCCUGCACGUU |

TABLE 1-continued

| SEQ ID NO | Name | Sequence |
|---|---|---|
| 138 | PHD2-106 | UCGUGCAGGGCGCGCACCUUUAGGUGCGCGCCCUGCACGAUU |
| 139 | PHD2-107 | GUCGUGCAGGGCGCGCACCUUGGUGCGCGCCCUGCACGACUU |
| 140 | PHD2-108 | UGUCGUGCAGGGCGCGCACUUGUGCGCGCCCUGCACGACAUU |
| 141 | PHD2-109 | GUGUCGUGCAGGGCGCGCAUUUGCGCGCCCUGCACGACACUU |
| 142 | PHD2-110 | GGUGUCGUGCAGGGCGCGCUUGCGCGCCCUGCACGACACCUU |
| 143 | PHD2-111 | CGGUGUCGUGCAGGGCGCGUUCGCGCCCUGCACGACACCGUU |
| 144 | PHD2-112 | CCGGUGUCGUGCAGGGCGCUUGCGCCCUGCACGACACCGGUU |
| 145 | PHD2-113 | CCCGGUGUCGUGCAGGGCGUUCGCCCUGCACGACACCGGGUU |
| 146 | PHD2-114 | CUGCCCGUCCGUGAACUUCUUGAAGUUCACGGACGGGCAGUU |
| 147 | PHD2-115 | GCUGCCCGUCCGUGAACUUUUAAGUUCACGGACGGGCAGCUU |
| 148 | PHD2-116 | AGCUGCCCGUCCGUGAACUUUAGUUCACGGACGGGCAGCUUU |
| 149 | PHD2-117 | CAGCUGCCCGUCCGUGAACUUGUUCACGGACGGGCAGCUGUU |
| 150 | PHD2-118 | CCAGCUGCCCGUCCGUGAAUUUUCACGGACGGGCAGCUGGUU |
| 151 | PHD2-119 | ACCAGCUGCCCGUCCGUGAUUUCACGGACGGGCAGCUGGUUU |
| 152 | PHD2-120 | GACCAGCUGCCCGUCCGUGUUCACGGACGGGCAGCUGGUCUU |
| 153 | PHD2-121 | UGACCAGCUGCCCGUCCGUUUACGGACGGGCAGCUGGUCAUU |
| 154 | PHD2-122 | CUGACCAGCUGCCCGUCCGUUCGGACGGGCAGCUGGUCAGUU |
| 155 | PHD2-123 | GCUGACCAGCUGCCCGUCCUUGGACGGGCAGCUGGUCAGCUU |
| 156 | PHD2-124 | GGCUGACCAGCUGCCCGUCUUGACGGGCAGCUGGUCAGCCUU |
| 157 | PHD2-125 | UGGCUGACCAGCUGCCCGUUUACGGGCAGCUGGUCAGCCAUU |
| 158 | PHD2-126 | CUGGCUGACCAGCUGCCCGUUCGGGCAGCUGGUCAGCCAGUU |
| 159 | PHD2-127 | UCUGGCUGACCAGCUGCCCUUGGGCAGCUGGUCAGCCAGAUU |
| 160 | PHD2-128 | UUCUGGCUGACCAGCUGCCUUGGCAGCUGGUCAGCCAGAAUU |
| 161 | PHD2-129 | CUUCUGGCUGACCAGCUGCUUGCAGCUGGUCAGCCAGAAGUU |
| 162 | PHD2-130 | UCUUCUGGCUGACCAGCUGUUCAGCUGGUCAGCCAGAAGAUU |
| 163 | PHD2-131 | CUCUUCUGGCUGACCAGCUUUAGCUGGUCAGCCAGAAGAGUU |

TABLE 1-continued

| SEQ ID NO | Name | Sequence |
|---|---|---|
| 164 | PHD2-132 | ACUCUUCUGGCUGACCAGCUUGCUGGUCAGCCAGAAGAGUUU |
| 165 | PHD2-133 | CACUCUUCUGGCUGACCAGUUCUGGUCAGCCAGAAGAGUGUU |
| 166 | PHD2-134 | UCACUCUUCUGGCUGACCAUUUGGUCAGCCAGAAGAGUGAUU |
| 167 | PHD2-135 | GUCACUCUUCUGGCUGACCUUGGUCAGCCAGAAGAGUGACUU |
| 168 | PHD2-136 | AGUCACUCUUCUGGCUGACUUGUCAGCCAGAAGAGUGACUUU |
| 169 | PHD2-137 | GAGUCACUCUUCUGGCUGAUUUCAGCCAGAAGAGUGACUCUU |
| 170 | PHD2-138 | CGAGUCACUCUUCUGGCUGUUCAGCCAGAAGAGUGACUCGUU |
| 171 | PHD2-139 | CCUCGAUCCAGGUGAUCUUUAAGAUCACCUGGAUCGAGGUU |
| 172 | PHD2-140 | CCCUCGAUCCAGGUGAUCUUUAGAUCACCUGGAUCGAGGGUU |
| 173 | PHD2-141 | GCCCUCGAUCCAGGUGAUCUUGAUCACCUGGAUCGAGGGCUU |
| 174 | PHD2-142 | UGCCCUCGAUCCAGGUGAUUUAUCACCUGGAUCGAGGGCAUU |
| 175 | PHD2-143 | UUGCCCUCGAUCCAGGUGAUUUCACCUGGAUCGAGGGCAAUU |
| 176 | PHD2-144 | CUUGCCCUCGAUCCAGGUGUUCACCUGGAUCGAGGGCAAGUU |
| 177 | PHD2-145 | GGUUUCGCAGCCGGGCUCCUUGGAGCCCGGCUGCGAAACCUU |
| 178 | PHD2-146 | UGGUUUCGCAGCCGGGCUCUUGAGCCCGGCUGCGAAACCAUU |
| 179 | PHD2-147 | AUGGUUUCGCAGCCGGGCUUUAGCCCGGCUGCGAAACCAUUU |
| 180 | PHD2-148 | AAUGGUUUCGCAGCCGGGCUUGCCCGGCUGCGAAACCAUUUU |
| 181 | PHD2-149 | CAUGCUGCUCAUGAGCAGCUUGCUGCUCAUGAGCAGCAUGUU |
| 182 | PHD2-150 | CCAUGCUGCUCAUGAGCAGUUCUGCUCAUGAGCAGCAUGGUU |
| 183 | PHD2-151 | UCCAUGCUGCUCAUGAGCAUUUGCUCAUGAGCAGCAUGGAUU |
| 184 | PHD2-152 | GUCCAUGCUGCUCAUGAGCUUGCUCAUGAGCAGCAUGGACUU |
| 185 | PHD2-153 | CGUCCAUGCUGCUCAUGAGUUCUCAUGAGCAGCAUGGACGUU |
| 186 | PHD2-154 | UCGUCCAUGCUGCUCAUGAUUUCAUGAGCAGCAUGGACGAUU |
| 187 | PHD2-155 | GUCGUCCAUGCUGCUCAUGUUCAUGAGCAGCAUGGACGACUU |
| 188 | PHD2-156 | GGUCGUCCAUGCUGCUCAUUUAUGAGCAGCAUGGACGACCUU |
| 189 | PHD2-157 | AGGUCGUCCAUGCUGCUCAUUUGAGCAGCAUGGACGACCUUU |

TABLE 1-continued

| SEQ ID NO | Name | Sequence |
|---|---|---|
| 190 | PHD2-158 | CAGGUCGUCCAUGCUGCUCUUGAGCAGCAUGGACGACCUGUUU |
| 191 | PHD2-159 | UCAGGUCGUCCAUGCUGCUUUAGCAGCAUGGACGACCUGAUUU |
| 192 | PHD2-160 | AUCAGGUCGUCCAUGCUGCUUGCAGCAUGGACGACCUGAUUU |
| 193 | PHD2-161 | UAUCAGGUCGUCCAUGCUGUUCAGCAUGGACGACCUGAUAUU |
| 194 | PHD2-162 | AGCAACCAUGGCUUUCGUCUUGACGAAAGCCAUGGUUGCUUU |
| 195 | PHD2-163 | AAGCAACCAUGGCUUUCGUUUACGAAAGCCAUGGUUGCUUUU |
| 196 | PHD2-164 | CAAGCAACCAUGGCUUUCGUUCGAAAGCCAUGGUUGCUUGUU |
| 197 | PHD2-165 | ACAAGCAACCAUGGCUUUCUUGAAAGCCAUGGUUGCUUGUUU |
| 198 | PHD2-166 | AACAAGCAACCAUGGCUUUUUAAAGCCAUGGUUGCUUGUUUU |
| 199 | PHD2-167 | UAACAAGCAACCAUGGCUUUUAAGCCAUGGUUGCUUGUUAUU |
| 200 | PHD2-168 | AUAACAAGCAACCAUGGCUUUAGCCAUGGUUGCUUGUUAUUU |
| 201 | PHD2-169 | UCUUCCAUCUCCAUUUGGAUUUCCAAAUGGAGAUGGAAGAUU |
| 202 | PHD2-170 | AUCUUCCAUCUCCAUUUGGUUCCAAAUGGAGAUGGAAGAUUU |
| 203 | PHD2-171 | CAUCUUCCAUCUCCAUUUGUUCAAAUGGAGAUGGAAGAUGUU |
| 204 | PHD2-172 | ACAUCUUCCAUCUCCAUUUUUAAAUGGAGAUGGAAGAUGUUU |
| 205 | PHD2-173 | AUAAUAUAUACAUGUCACAUUUGUGACAUGUAUAUAUUAUUU |
| 206 | PHD2-174 | GAUAAUAUAUACAUGUCACUUGUGACAUGUAUAUAUUAUCUU |
| 207 | PHD2-175 | AGAUAAUAUAUACAUGUCAUUUGACAUGUAUAUAUUAUCUUU |
| 208 | PHD2-176 | AAGAUAAUAUAUACAUGUCUUGACAUGUAUAUAUUAUCUUUU |
| 209 | PHD2-177 | ACCUCCACUUACCUUGGCAUUUGCCAAGGUAAGUGGAGGUUU |
| 210 | PHD2-178 | UACCUCCACUUACCUUGGCUUGCCAAGGUAAGUGGAGGUAUU |
| 211 | PHD2-179 | AUACCUCCACUUACCUUGGUUCCAAGGUAAGUGGAGGUAUUU |
| 212 | PHD2-180 | UAUACCUCCACUUACCUUGUUCAAGGUAAGUGGAGGUAUAUU |
| 213 | PHD2-181 | UUCUGGAAAAUUCGAAGUUUACUUCGAAUUUUCCAGAAUU |
| 214 | PHD2-182 | CUUCUGGAAAAUUCGAAGUUCUUCGAAUUUUCCAGAAGUU |
| 215 | PHD2-183 | CCUUCUGGAAAAUUCGAAUUUUCGAAUUUUCCAGAAGGUU |

TABLE 1-continued

| SEQ ID NO | Name | Sequence |
|---|---|---|
| 216 | PHD2-184 | GCCUUCUGGAAAAAUUCGAUUUCGAAUUUUUCCAGAAGGCUU |
| 217 | PHD2-185 | UGCCUUCUGGAAAAAUUCGUUCGAAUUUUUCCAGAAGGCAUU |
| 218 | PHD2-186 | UUGCCUUCUGGAAAAAUUCUUGAAUUUUUCCAGAAGGCAAUU |
| 219 | PHD2-187 | UUUGCCUUCUGGAAAAAUUUUAAUUUUUCCAGAAGGCAAAUU |
| 220 | PHD2-188 | CUUUGCCUUCUGGAAAAAUUUAUUUUUCCAGAAGGCAAAGUU |
| 221 | PHD2-189 | GCUUUGCCUUCUGGAAAAAUUUUUUUCCAGAAGGCAAAGCUU |
| 222 | PHD2-190 | GGCUUUGCCUUCUGGAAAAUUUUUCCAGAAGGCAAAGCCUU |
| 223 | PHD2-191 | GGGCUUUGCCUUCUGGAAAUUUUUCCAGAAGGCAAAGCCCUU |
| 224 | PHD2-192 | UGGGCUUUGCCUUCUGGAAUUUUCCAGAAGGCAAAGCCCAUU |
| 225 | PHD2-193 | CUGGGCUUUGCCUUCUGGAUUUCCAGAAGGCAAAGCCCAGUU |
| 226 | PHD2-194 | ACUGGGCUUUGCCUUCUGGUUCCAGAAGGCAAAGCCCAGUUU |
| 227 | PHD2-195 | AACUGGGCUUUGCCUUCUGUUCAGAAGGCAAAGCCCAGUUUU |
| 228 | PHD2-196 | AAACUGGGCUUUGCCUUCUUUAGAAGGCAAAGCCCAGUUUUU |
| 229 | PHD2-197 | CAAACUGGGCUUUGCCUUCUUGAAGGCAAAGCCCAGUUUGUU |
| 230 | PHD2-198 | GCAAACUGGGCUUUGCCUUUUAAGGCAAAGCCCAGUUUGCUU |
| 231 | PHD2-199 | AGCAAACUGGGCUUUGCCUUUAGGCAAAGCCCAGUUUGCUUU |
| 232 | PHD2-200 | CAGCAAACUGGGCUUUGCCUUGGCAAAGCCCAGUUUGCUGUU |
| 233 | PHD2-201 | UCAGCAAACUGGGCUUUGCUUGCAAAGCCCAGUUUGCUGAUU |
| 234 | PHD2-202 | GUCAGCAAACUGGGCUUUGUUCAAAGCCCAGUUUGCUGACUU |
| 235 | PHD2-203 | UGUCAGCAAACUGGGCUUUUAAAGCCCAGUUUGCUGACAUU |
| 236 | PHD2-204 | AUGUCAGCAAACUGGGCUUUUAAGCCCAGUUUGCUGACAUUU |
| 237 | PHD2-205 | AAUGUCAGCAAACUGGGCUUUAGCCCAGUUUGCUGACAUUUU |
| 238 | PHD2-206 | CAAUGUCAGCAAACUGGGCUUGCCCAGUUUGCUGACAUUGUU |
| 239 | PHD2-207 | UCAAUGUCAGCAAACUGGGUUCCCAGUUUGCUGACAUUGAUU |
| 240 | PHD2-208 | UUCAAUGUCAGCAAACUGGUUCCAGUUUGCUGACAUUGAAUU |
| 241 | PHD2-209 | GUUCAAUGUCAGCAAACUGUUCAGUUUGCUGACAUUGAACUU |

TABLE 1-continued

| SEQ ID NO | Name | Sequence |
|---|---|---|
| 242 | PHD2-210 | GGUUCAAUGUCAGCAAACUUUAGUUUGCUGACAUUGAACCUU |
| 243 | PHD2-211 | GGGUUCAAUGUCAGCAAACUUGUUUGCUGACAUUGAACCCUU |
| 244 | PHD2-212 | UGGGUUCAAUGUCAGCAAAUUUUGCUGACAUUGAACCCAUU |
| 245 | PHD2-213 | UUGGGUUCAAUGUCAGCAAUUUUGCUGACAUUGAACCCAAUU |
| 246 | PHD2-214 | UUUGGGUUCAAUGUCAGCAUUUGCUGACAUUGAACCCAAAUU |
| 247 | PHD2-215 | AUUUGGGUUCAAUGUCAGCUUGCUGACAUUGAACCCAAAUUU |
| 248 | PHD2-216 | AAUUUGGGUUCAAUGUCAGUUCUGACAUUGAACCCAAAUUUU |
| 249 | PHD2-217 | AAAUUUGGGUUCAAUGUCAUUUGACAUUGAACCCAAAUUUUU |
| 250 | PHD2-218 | CAAAUUUGGGUUCAAUGUCUUGACAUUGAACCCAAAUUUGUU |
| 251 | PHD2-219 | UCAAAUUUGGGUUCAAUGUUUACAUUGAACCCAAAUUUGAUU |
| 252 | PHD2-220 | AUCAAAUUUGGGUUCAAUGUUCAUUGAACCCAAAUUUGAUUU |
| 253 | PHD2-221 | UAUCAAAUUUGGGUUCAAUUUAUUGAACCCAAAUUUGAUAUU |
| 254 | PHD2-222 | CUAUCAAAUUUGGGUUCAAUUUUGAACCCAAAUUUGAUAGUU |
| 255 | PHD2-223 | UCUAUCAAAUUUGGGUUCAUUUGAACCCAAAUUUGAUAGAUU |
| 256 | PHD2-224 | GUCUAUCAAAUUUGGGUUCUUGAACCCAAAUUUGAUAGACUU |
| 257 | PHD2-225 | AGUCUAUCAAAUUUGGGUUUUAACCCAAAUUUGAUAGACUUU |
| 258 | PHD2-226 | CAGUCUAUCAAAUUUGGGUUUACCCAAAUUUGAUAGACUGUU |
| 259 | PHD2-227 | GCAGUCUAUCAAAUUUGGGUUCCCAAAUUUGAUAGACUGCUU |
| 260 | PHD2-228 | AGCAGUCUAUCAAAUUUGGUUCCAAAUUUGAUAGACUGCUUU |
| 261 | PHD2-229 | CAGCAGUCUAUCAAAUUUGUUCAAAUUUGAUAGACUGCUGUU |
| 262 | PHD2-230 | ACAGCAGUCUAUCAAAUUUUAAAUUUGAUAGACUGCUGUUU |
| 263 | PHD2-231 | AACAGCAGUCUAUCAAAUUUAAUUUGAUAGACUGCUGUUUUU |
| 264 | PHD2-232 | AAACAGCAGUCUAUCAAAUUUAUUUGAUAGACUGCUGUUUUU |
| 265 | PHD2-233 | AAAACAGCAGUCUAUCAAAUUUUGAUAGACUGCUGUUUUUUU |
| 266 | PHD2-234 | AAAAACAGCAGUCUAUCAAAUUUUGAUAGACUGCUGUUUUUUU |
| 267 | PHD2-235 | GAAAAACAGCAGUCUAUCAUUUGAUAGACUGCUGUUUUUCUU |

TABLE 1-continued

| SEQ ID NO | Name | Sequence |
|---|---|---|
| 268 | PHD2-236 | AGAAAAACAGCAGUCUAUCUUGAUAGACUGCUGUUUUUCUUU |
| 269 | PHD2-237 | CAGAAAAACAGCAGUCUAUUUAUAGACUGCUGUUUUUCUGUU |
| 270 | PHD2-238 | CCAGAAAAACAGCAGUCUAUUUAGACUGCUGUUUUUCUGGUU |
| 271 | PHD2-239 | ACCAGAAAAACAGCAGUCUUUAGACUGCUGUUUUUCUGGUUU |
| 272 | PHD2-240 | GACCAGAAAAACAGCAGUCUUGACUGCUGUUUUUCUGGUCUU |
| 273 | PHD2-241 | AGACCAGAAAAACAGCAGUUUACUGCUGUUUUUCUGGUCUUU |
| 274 | PHD2-242 | CAGACCAGAAAAACAGCAGUUCUGCUGUUUUUCUGGUCUGUU |
| 275 | PHD2-243 | UCAGACCAGAAAAACAGCAUUUGCUGUUUUUCUGGUCUGAUU |
| 276 | PHD2-244 | GUCAGACCAGAAAAACAGCUUGCUGUUUUUCUGGUCUGACUU |
| 277 | PHD2-245 | GGUCAGACCAGAAAAACAGUUCUGUUUUUCUGGUCUGACCUU |
| 278 | PHD2-246 | CGGUCAGACCAGAAAAACAUUUGUUUUUCUGGUCUGACCGUU |
| 279 | PHD2-247 | ACGGUCAGACCAGAAAAACUUGUUUUUCUGGUCUGACCGUUU |
| 280 | PHD2-248 | UUGUACUUCAUGAGGGUUGUUCAACCCUCAUGAAGUACAAUU |
| 281 | PHD2-249 | AGUUAUUGCGUACCUUGUAUUUACAAGGUACGCAAUAACUUU |
| 282 | PHD2-250 | CAGUUAUUGCGUACCUUGUUUACAAGGUACGCAAUAACUGUU |
| 283 | PHD2-251 | ACAGUUAUUGCGUACCUUGUUCAAGGUACGCAAUAACUGUUU |
| 284 | PHD2-252 | AACAGUUAUUGCGUACCUUUUAAGGUACGCAAUAACUGUUUU |
| 285 | PHD2-253 | AAACAGUUAUUGCGUACCUUUAGGUACGCAAUAACUGUUUUU |
| 286 | PHD2-254 | CAAACAGUUAUUGCGUACCUUGGUACGCAAUAACUGUUUGUU |
| 287 | PHD2-255 | CCAAACAGUUAUUGCGUACUUGUACGCAAUAACUGUUUGGUU |
| 288 | PHD2-256 | ACCAAACAGUUAUUGCGUAUUUACGCAAUAACUGUUUGGUUU |
| 289 | PHD2-257 | UACCAAACAGUUAUUGCGUUUACGCAAUAACUGUUUGGUAUU |
| 290 | PHD2-258 | AUACCAAACAGUUAUUGCGUUCGCAAUAACUGUUUGGUAUUU |
| 291 | PHD2-259 | AAUACCAAACAGUUAUUGCUUGCAAUAACUGUUUGGUAUUUU |
| 292 | PHD2-260 | AAAUACCAAACAGUUAUUGUUCAAUAACUGUUUGGUAUUUUU |
| 293 | PHD2-261 | CAAACAGUUAUUUAAUAACUGUUUGGUAUUUUUU |

TABLE 1-continued

| SEQ ID NO | Name | Sequence |
|---|---|---|
| 294 | PHD2-262 | CAAAAUACCAAACAGUUAUUUAUAACUGUUUGGUAUUUUGUUU |
| 295 | PHD2-263 | UCAAAAUACCAAACAGUUAUUUAACUGUUUGGUAUUUUGAUU |
| 296 | PHD2-264 | AUCAAAAUACCAAACAGUUUUAACUGUUUGGUAUUUUGAUUU |
| 297 | PHD2-265 | CAUCAAAAUACCAAACAGUUUACUGUUUGGUAUUUUGAUGUU |
| 298 | PHD2-266 | GCAUCAAAAUACCAAACAGUUCUGUUUGGUAUUUUGAUGCUU |
| 299 | PHD2-267 | UGCAUCAAAAUACCAAACAUUUGUUUGGUAUUUUGAUGCAUU |
| 300 | PHD2-268 | CUGCAUCAAAAUACCAAACUUGUUUGGUAUUUUGAUGCAGUU |
| 301 | PHD2-269 | UCUGCAUCAAAAUACCAAAUUUUGGUAUUUUGAUGCAGAUU |
| 302 | PHD2-270 | AUCUGCAUCAAAAUACCAAUUUUGGUAUUUUGAUGCAGAUUU |
| 303 | PHD2-271 | CAUCUGCAUCAAAAUACCAUUUGGUAUUUUGAUGCAGAUGUU |
| 304 | PHD2-272 | UCAUCUGCAUCAAAAUACCUUGGUAUUUUGAUGCAGAUGAUU |
| 305 | PHD2-273 | CUCAUCUGCAUCAAAAUACUUGUAUUUUGAUGCAGAUGAGUU |
| 306 | PHD2-274 | UCUCAUCUGCAUCAAAAUAUUUAUUUUGAUGCAGAUGAGAUU |
| 307 | PHD2-275 | GAUAUUUUACUUUAGCUCGUUCGAGCUAAAGUAAAAUAUCUU |
| 308 | PHD2-276 | AGAUAUUUUACUUUAGCUCUUGAGCUAAAGUAAAAUAUCUUU |
| 309 | PHD2-277 | UAGAUAUUUUACUUUAGCUUUAGCUAAAGUAAAAUAUCUAUU |
| 310 | PHD2-278 | UUAGAUAUUUUACUUUAGCUUGCUAAAGUAAAAUAUCUAAUU |
| 311 | PHD2-279 | GUUAGAUAUUUUACUUUAGUUCUAAAGUAAAAUAUCUAACUU |
| 312 | PHD2-280 | UGUUAGAUAUUUUACUUUAUUUAAAGUAAAAUAUCUAACAUU |
| 313 | PHD2-281 | CUGUUAGAUAUUUUACUUUUUAAAGUAAAAUAUCUAACAGUU |
| 314 | PHD2-282 | CCUGUUAGAUAUUUUACUUUUAAGUAAAAUAUCUAACAGGUU |
| 315 | PHD2-283 | ACCUGUUAGAUAUUUUACUUUAGUAAAAUAUCUAACAGGUUU |
| 316 | PHD2-284 | CACCUGUUAGAUAUUUUACUUGUAAAAUAUCUAACAGGUGUU |
| 317 | PHD2-285 | UCACCUGUUAGAUAUUUUAUUUAAAAUAUCUAACAGGUGAUU |
| 318 | PHD2-286 | UUCACCUGUUAGAUAUUUUUUAAAAUAUCUAACAGGUGAAUU |
| 319 | PHD2-287 | UUCAACCCUCACACCAAAAGGUGUGAGGGUUGAAUU |

TABLE 1-continued

| SEQ ID NO | Name | Sequence |
|---|---|---|
| 320 | PHD2-288 | GUUCAACCCUCACACCUUUUAAAGGUGUGAGGGUUGAACUU |
| 321 | PHD2-289 | AGUUCAACCCUCACACCUUUUAAGGUGUGAGGGUUGAACUUU |
| 322 | PHD2-290 | GAGUUCAACCCUCACACCUUUAGGUGUGAGGGUUGAACUCUU |
| 323 | PHD2-291 | UGAGUUCAACCCUCACACCUUGGUGUGAGGGUUGAACUCAUU |
| 324 | PHD2-292 | UUGAGUUCAACCCUCACACUUGUGUGAGGGUUGAACUCAAUU |
| 325 | PHD2-293 | AUUGAGUUCAACCCUCACAUUUGUGAGGGUUGAACUCAAUUU |
| 326 | SG606 | U*C*A*GCCGCUGUCACACGCA*C*A*G |
| 327 | SG607 | G*1C*U*G*1T*C*A*C*A*C*1G*C*A*1C*A |
| 328 | SG615 | U/ZEN/CAGCCGCUGUCACACGCACA/ZEN/ |
| 329 | miR-210 antisense | UCAGCCGCUGUCACACGCACAG |

EXAMPLES

Example 1. Targeting of PHD2 with sshRNA

Figure 2A:
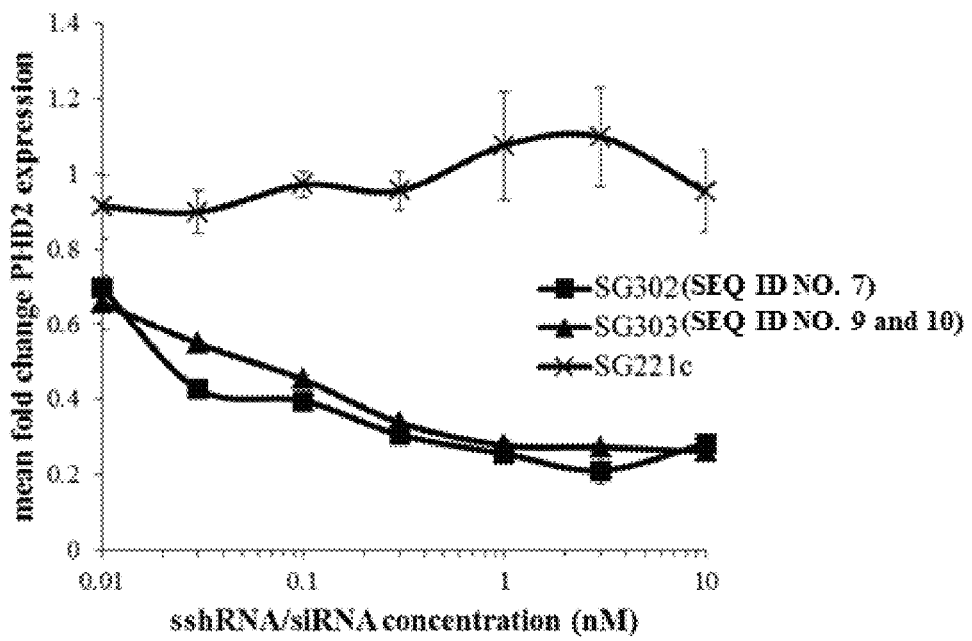
FIG. 2A-FIG. 2B illustrate expression of PHD2 transcript in response to treatment with an RNA interference (RNAi) molecule.
Figure 2B:
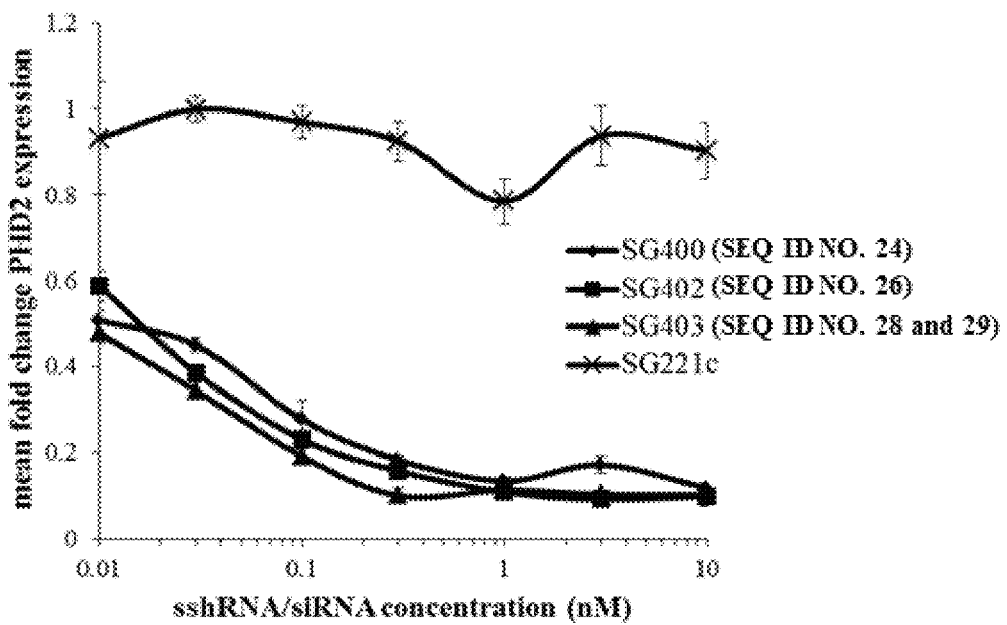

FIG. 2A shows quantitative reverse transcription PCR (qRT-PCR) of human PHD2 (SEQ ID NO. 1) transcript in human embryonic kidney 293FT cells transfected with increasing amounts of a sshRNA (SG302, SEQ ID NO. 7) or siRNA (SG303, SEQ ID NO. 9 and SEQ ID NO. 10) targeting PHD2 or a control sshRNA (SG221c). Transcript levels were quantified using the $2^{-\Delta\Delta Ct}$ method relative to cells not transfected with inhibitor and normalized to GAPDH transcript. FIG. 2B shows qRT-PCR of mouse PHD2 (SEQ ID NO. 2) transcript in mouse NIH3T3 fibroblasts transfected with increasing amounts of PHD2-targeting sshRNAs (SG400, SEQ ID NO. 24 and SG402, SEQ ID NO. 26), PHD2-targeting siRNA (SG403, SEQ ID NO. 28 and SEQ ID NO. 29) or a control sshRNA (SG221c). Transcript levels were quantified using the $2^{-\Delta\Delta Ct}$ method relative to cells not transfected with inhibitor and normalized to GAPDH transcript.

Example 2. Targeting of the HIF-1α Network with PHD2 sshRNA

Figure 3A:
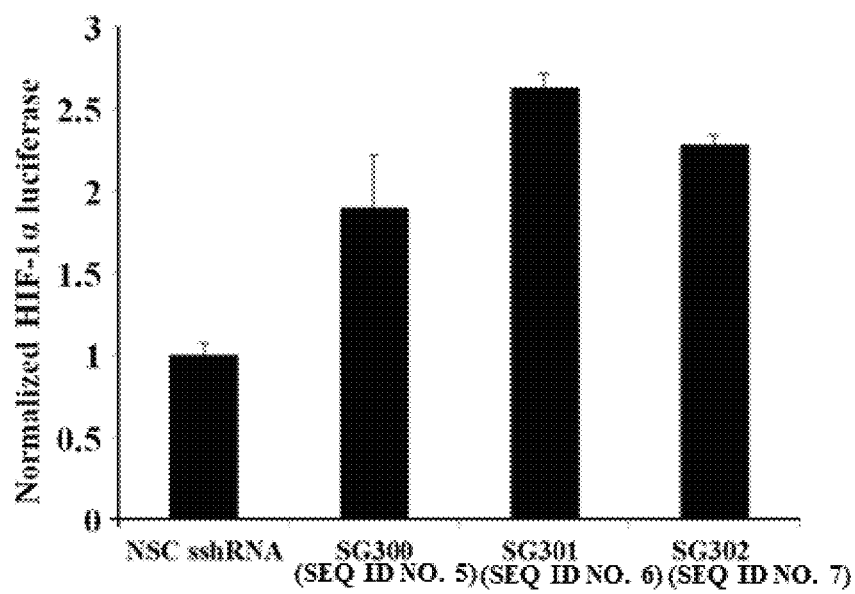
FIG. 3A-FIG. 3C illustrate HIF-1α pathway measurements in response to treatment with an RNAi molecule.
Figure 3B:
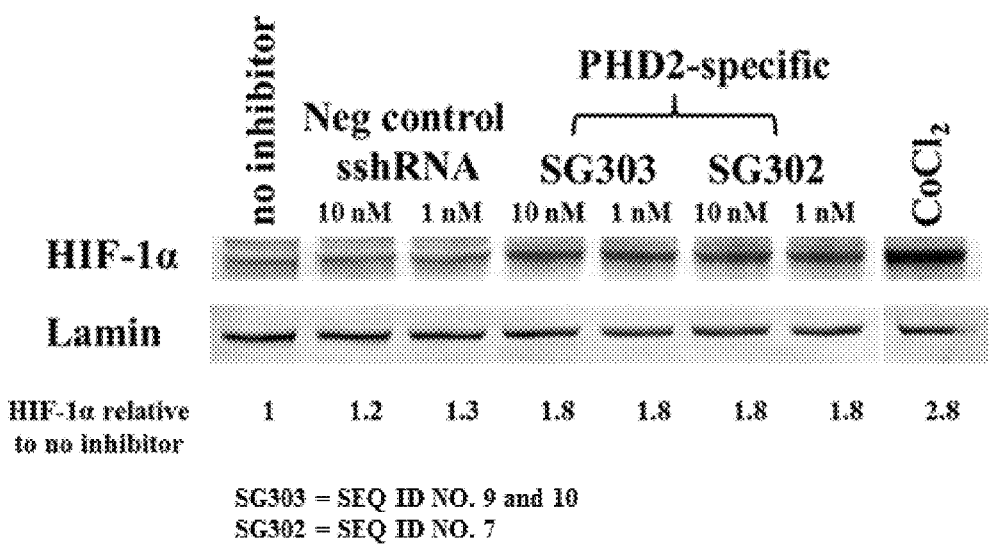
Figure 3C:
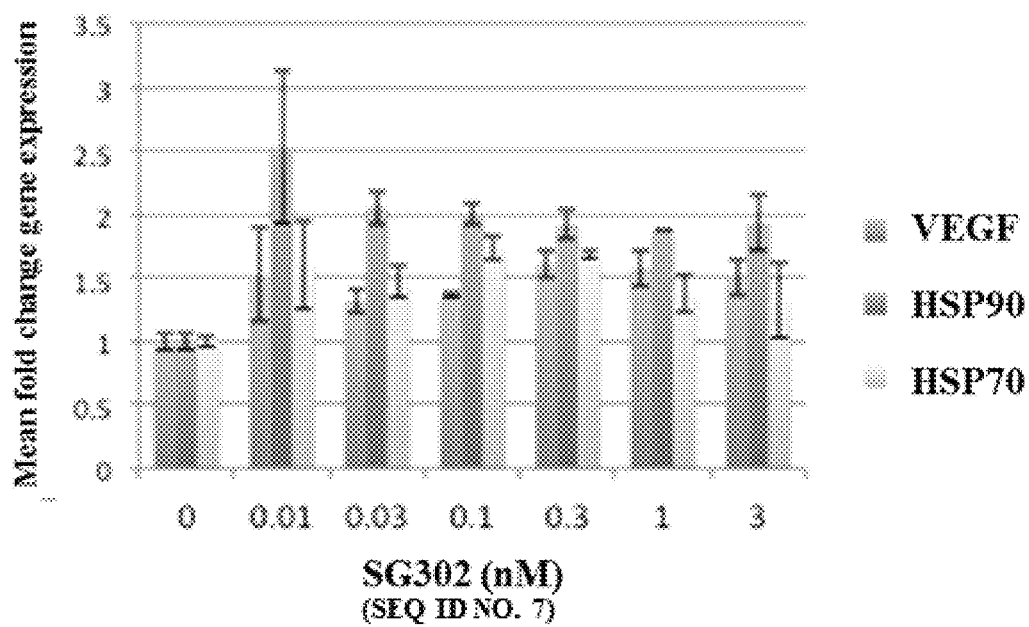

FIG. 3A shows the results of a luciferase reporter assay in which a plasmid of firefly luciferase (f-Luc) is under the control of a promoter containing HIF-1α responsive elements. A plasmid that constitutively expresses Renilla luciferase (r-Luc) was used as a transfection normalization control. Human embryonic kidney 293FT cells were co-transfected with the above plasmids and individual sshRNAs targeting PHD2 (SG300 (SEQ ID NO. 5), SG301 (SEQ ID NO. 6), or SG302 (SEQ ID NO. 7)) or with a control sshRNA (NSC sshRNA). 48 hours after transfection, the f-Luc signal normalized to r-Luc was determined. Values are normalized to a NSC sshRNAs control. FIG. 3B shows Western blotting studies of HIF-1α and Lamin protein in Human embryonic kidney 293FT cells treated with no inhibitor (lane 1), two concentrations of control sshRNA (Neg control sshRNA; lanes 2 and 3), two concentrations each of SG303 (SEQ ID NO. 9 and SEQ ID NO. 10) and SG302 (SEQ ID NO. 7) (lanes 4 and 5 and 6 and 7, respectively), and untransfected cells treated with cobalt chloride ($CoCl_2$; lane 8). Values of HIF-1α are calculated relative to no inhibitor treatment and are normalized to Lamin. FIG. 3C shows qRT-PCR of VEGF (lanes 1, 4, 7, 10, 13, 16, and 19), HSP90 (lanes 2, 5, 8, 11, 14, 17, and 20), and HSP70 (lanes 3, 6, 9, 12, 15, 18, and 21) in human embryonic kidney 293FT cells transfected with increasing amounts of SG302 (SEQ ID NO. 7). Total RNA was isolated 48 hours after transfection. Quantification is expressed as fold-induction relative to untransfected cells and normalized to GAPDH using the $2^{-\Delta\Delta Ct}$ method.

Example 3. Effect of sshRNA Modification on RNAi

Figure 4A:
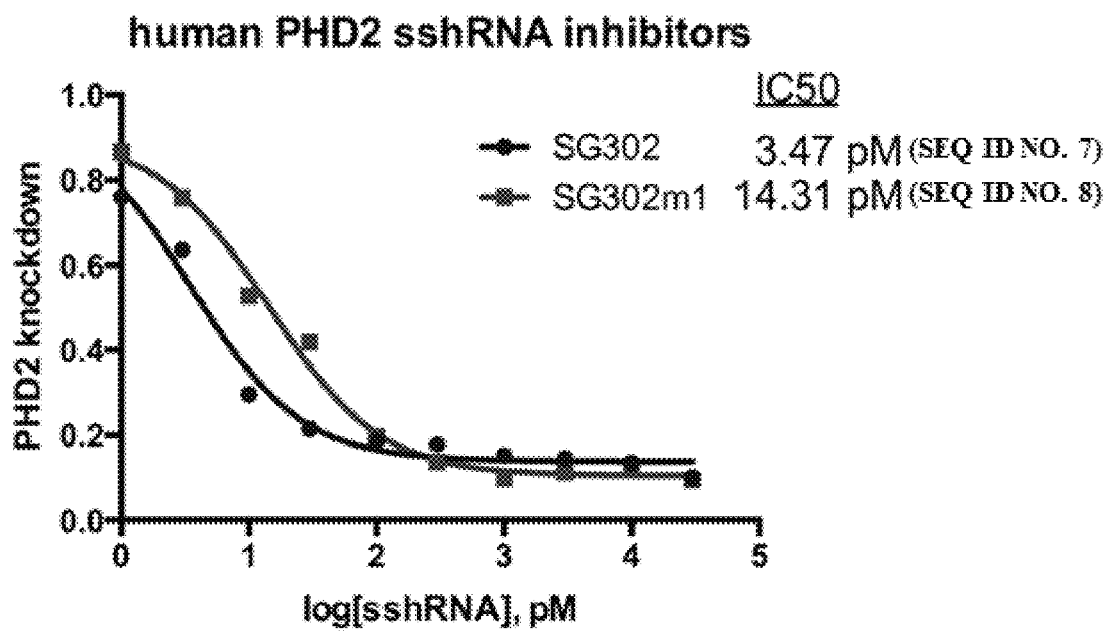
FIG. 4A-FIG. 4C illustrate expression of PHD2 transcript in response to treatment with an RNAi molecule.
Figure 4B:
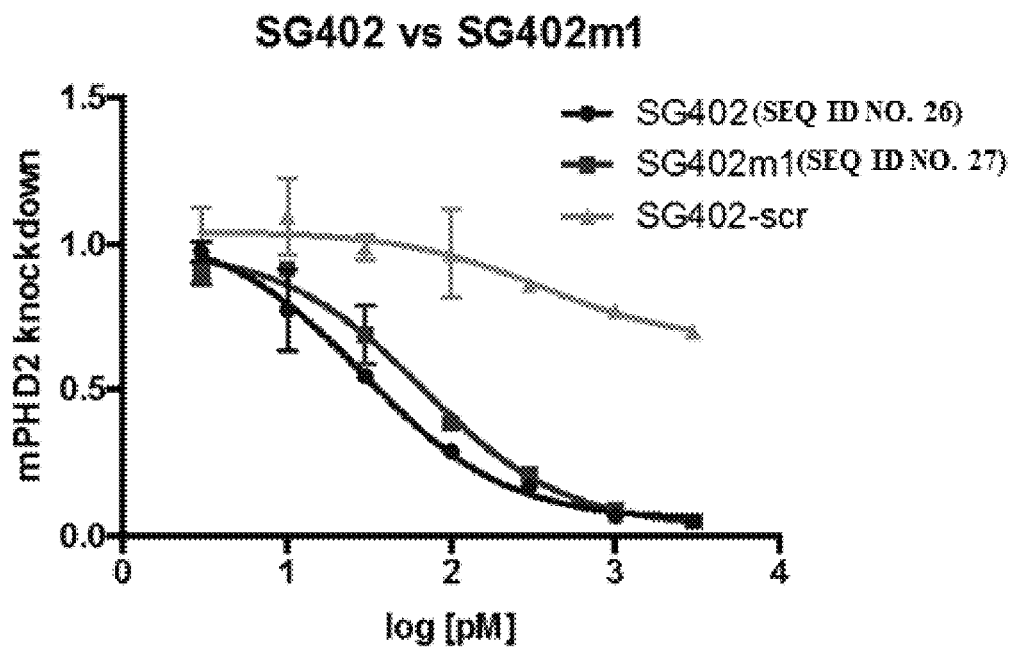
Figure 4C:
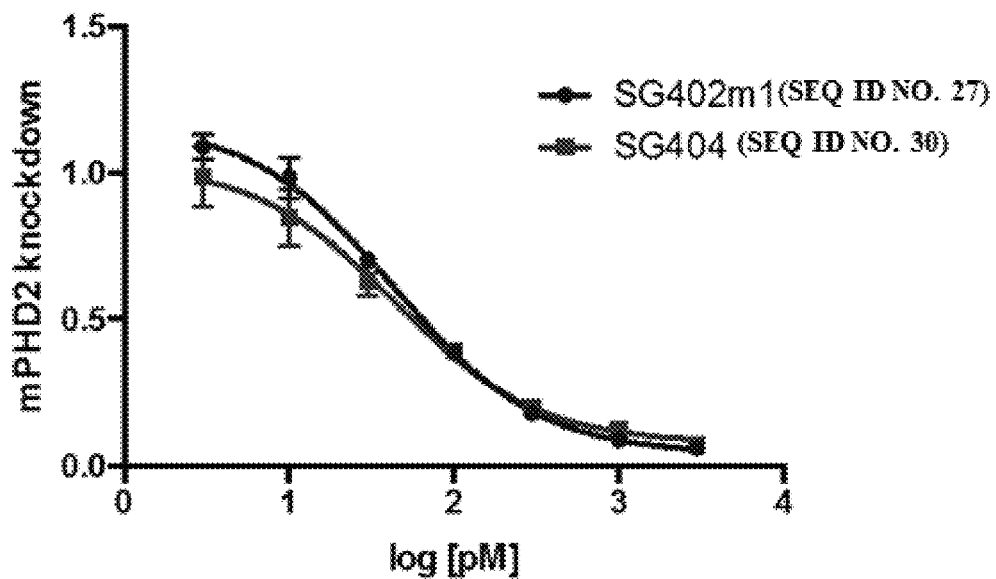

FIG. 4A shows qRT-PCR of human PHD2 transcript in human primary normal human epidermal keratinocytes (NHEK) transfected with increasing amounts of SG302 (SEQ ID NO. 7) or a modified sshRNA targeting PHD2 (SG302m1, SEQ ID NO. 8). Total RNA was isolated 48 h after transfection. PHD2 transcripts were quantified by the $2^{-\Delta\Delta Ct}$ method, normalizing to GAPDH. Quantification is expressed as fold-inhibition relative to untransfected cells. FIG. 4B shows qRT-PCR of mouse PHD2 transcript in mouse NIH3T3 fibroblasts transfected with increasing amounts of SG402 (SEQ ID NO. 26), a modified sshRNA targeting PHD2 (SG402m1, SEQ ID NO. 27), or a scrambled control sshRNA (SG402-scr). Values are normalized relative to a control transcript (GAPDH) and to untransfected mouse cells and quantified using the $2^{\Delta\Delta Ct}$ method. FIG. 4C shows qRT-PCR of mouse PHD2 (mPHD2) transcript in mouse NIH3T3 fibroblasts transfected with increasing amounts of an unmodified sshRNA targeting PHD2 (SG404, SEQ ID NO. 30) or SG402m1 (SEQ ID NO. 27). Data were analyzed as described in FIG. 4B.

Example 4. Effect of sshRNAs on Immunostimulatory Pathways

Figure 5A:
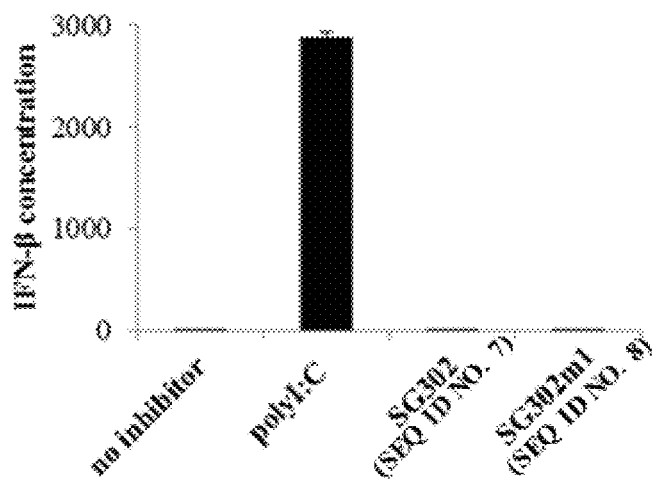
FIG. 5A-FIG. 5F illustrate cytokine levels in response to treatment with an RNAi molecule.
Figure 5B:
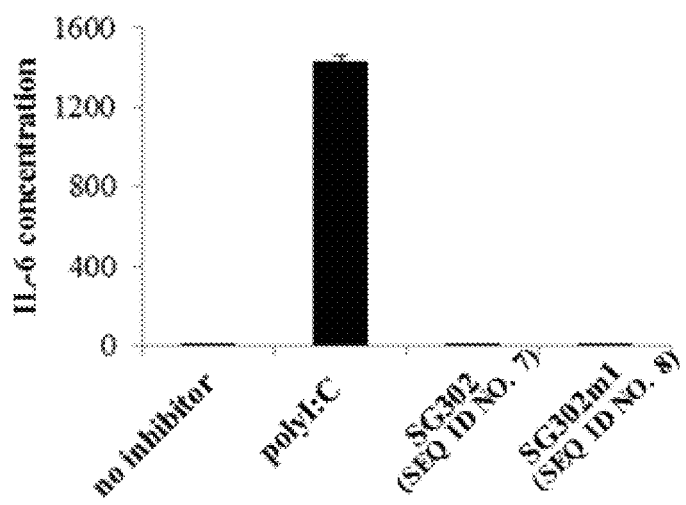
Figure 5C:
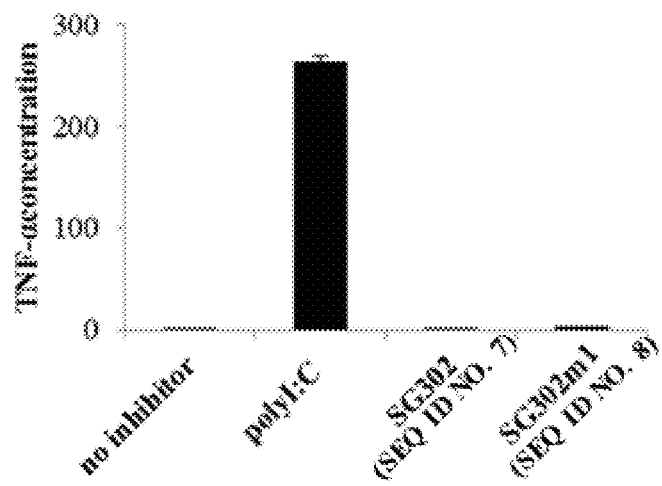
Figure 5D:
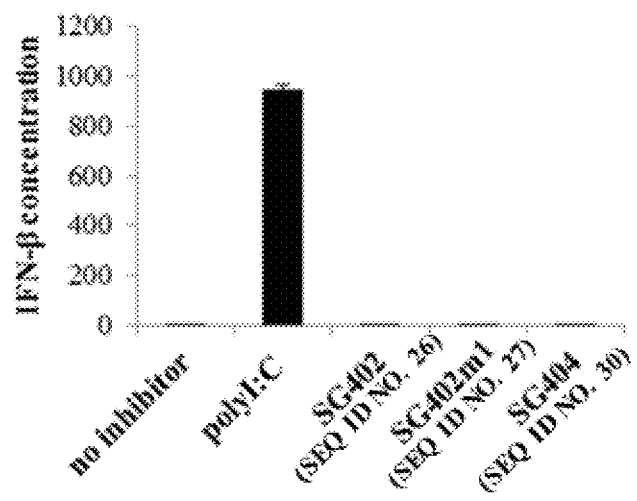
Figure 5E:
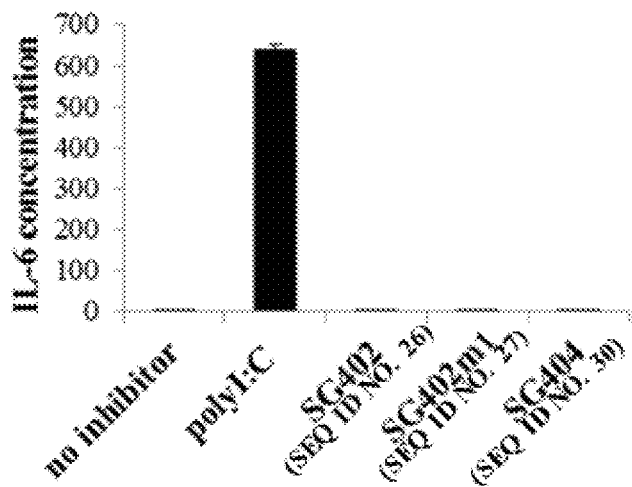
Figure 5F:
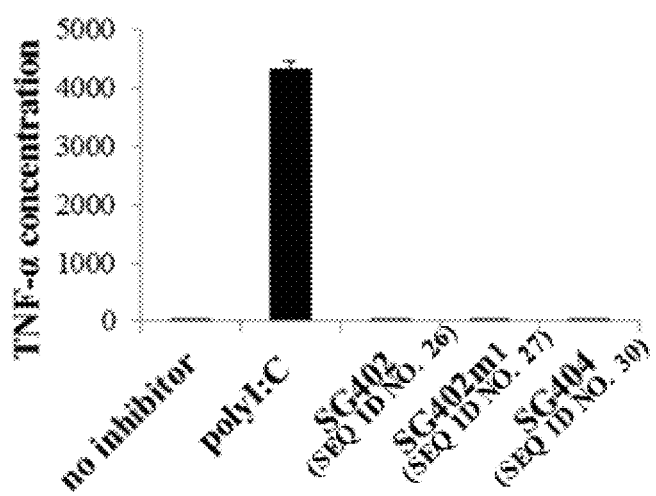

MRC-5 human lung fibroblasts were seeded in 24-well plates at $6 \times 10^4$ cells per well with Minimum Essential Medium containing 10% fetal calf serum. Transfections were performed using Lipofectamine 2000. 20 nanomolar (nM) sshRNAs or an equivalent amount of poly-inosine/cytosine (poly I:C) were transfected in triplicate. Untransfected cells and cells receiving Lipofectamine 2000 alone were used as negative controls. 24 hours later, the cells were lysed in TRIzol® (Invitrogen™ Carlsbad, Calif.) and total RNA was extracted according to the manufacturer's instructions. QRT-PCR was performed using a High-Capacity cDNA Reverse Transcription Kit with the TaqMan® Universal PCR Master Mix, IFN-β, IL-6, TNF-α, and GAPDH TaqMan® probes, and a 7500 Fast real-time PCR system (Applied Biosystems, Foster City, Calif.) following the manufacturer's protocol. IFN-β, IL-6, and TNF-α transcripts were quantified by the $2^{\Delta\Delta Ct}$ method, normalizing to GAPDH. FIG. 5A shows qRT-PCR assays for IFN-β in cells treated with no inhibitor, poly-inosine/cytosine (polyI:C), SG302 (SEQ ID NO. 7), or SG302m1 (SEQ ID NO. 8). FIG. 5B shows qRT-PCR assays for IL-6 in cells treated with no inhibitor, polyI:C, SG302 (SEQ ID NO. 7), or SG302m1 (SEQ ID NO. 8). FIG. 5C shows qRT-PCR assays for TNF-α in cells treated with no inhibitor, polyI:C, SG302 (SEQ ID NO. 7), or SG302m1 (SEQ ID NO. 8). FIG. 5D shows qRT-PCR for IFN-β in cells treated with no inhibitor, polyI:C, SG402 (SEQ ID NO. 26), SG402m1 (SEQ ID NO. 27), or SG404 (SEQ ID NO. 30). FIG. 5E shows qRT-PCR assays for IL-6 in cells treated with no inhibitor, polyI:C, SG402 (SEQ ID NO. 26), SG402m1 (SEQ ID NO. 27), or SG404 (SEQ ID NO. 30). FIG. 5F shows qRT-PCR assays for TNF-α in cells treated with no inhibitor, polyI:C, SG402 (SEQ ID NO. 26), SG402m1 (SEQ ID NO. 27), or SG404 (SEQ ID NO. 30).

Example 5. Effect of sshRNA Modification on Serum Stability

Figure 6:
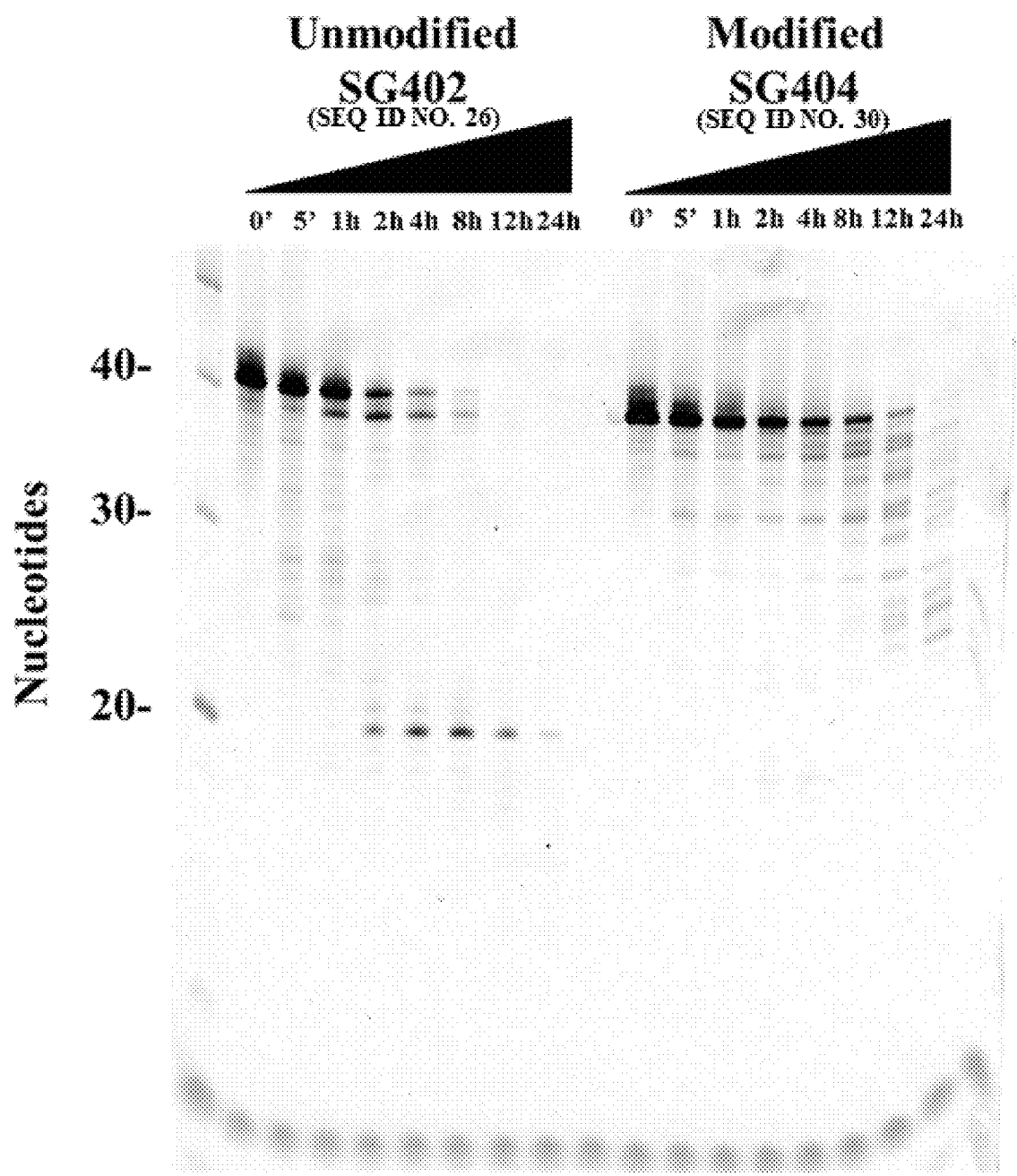
FIG. 6 illustrates stability of RNAi molecule in serum.

FIG. 6 shows serum stability assays for unmodified sshRNAs (SG402, SEQ ID NO. 26) and modified shRNAs (SG404, SEQ ID NO. 30). 3.35 micrograms (μg) of SG404 (SEQ ID NO. 30) and SG402 (SEQ ID NO. 26) were incubated with 10% human serum (Sigma-Aldrich, St Louis, Mo.) in phosphate-buffered saline at 37° C. for various times (from 0 minutes (0') to 24 hours (24 h)). At each time point, an aliquot was taken out, mixed with 2× gel loading buffer (Ambion®, Austin, Tex.), and immediately stored in −80° C. The samples were analyzed by 12% denaturing polyacrylamide gel electrophoresis (12% polyacrylamide, 20% formamide, and 8M urea) and were stained with SYBR Gold (Invitrogen™, Carlsbad, Calif.). Bands at about 40 nucleotides correspond to the full-length sshRNA.

Example 6. Effect of Combining sshRNA with miRNA Antagonist

Figure 7A:
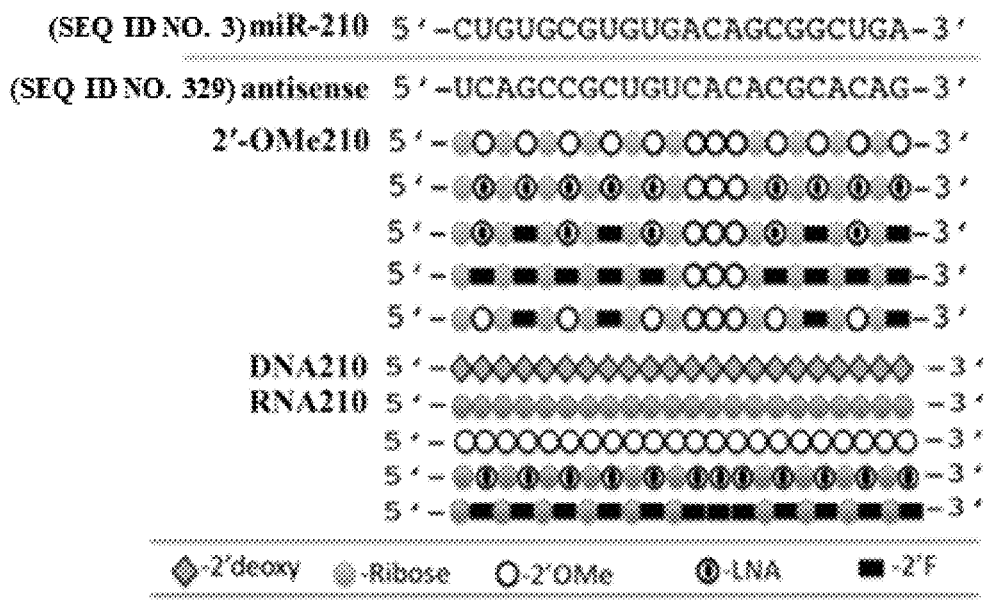
FIG. 7A-FIG. 7J illustrate designs for a miRNA antagonist, expression of PHD2 transcript, expression of miR-210 microRNA (miRNA), and activity of a miR-210 reporter in response to treatment with an RNAi molecule or a miRNA antagonist.
Figure 7B:
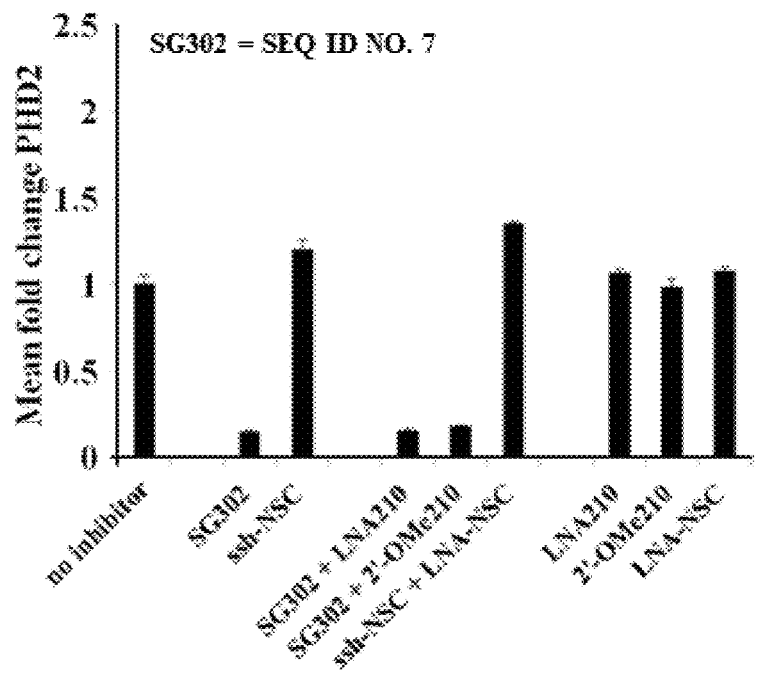
Figure 7C:
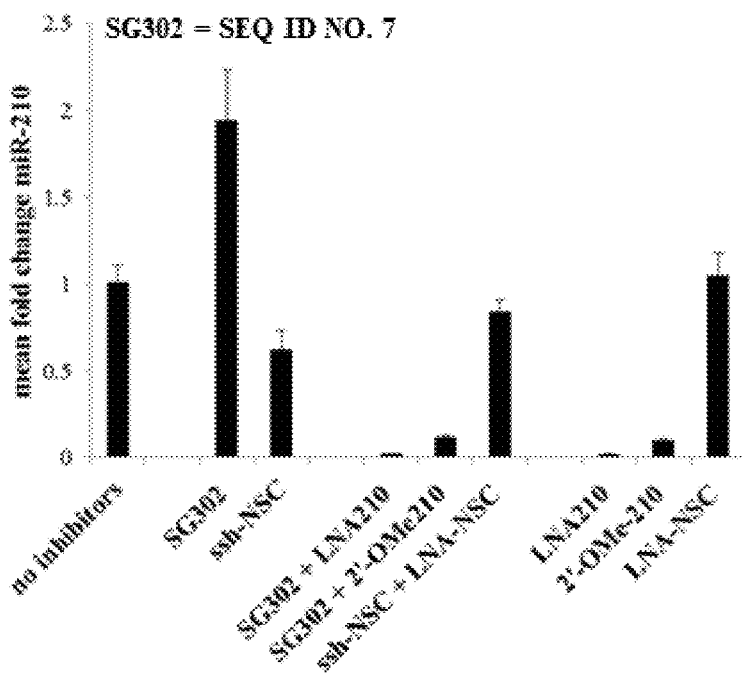
Figure 7D:
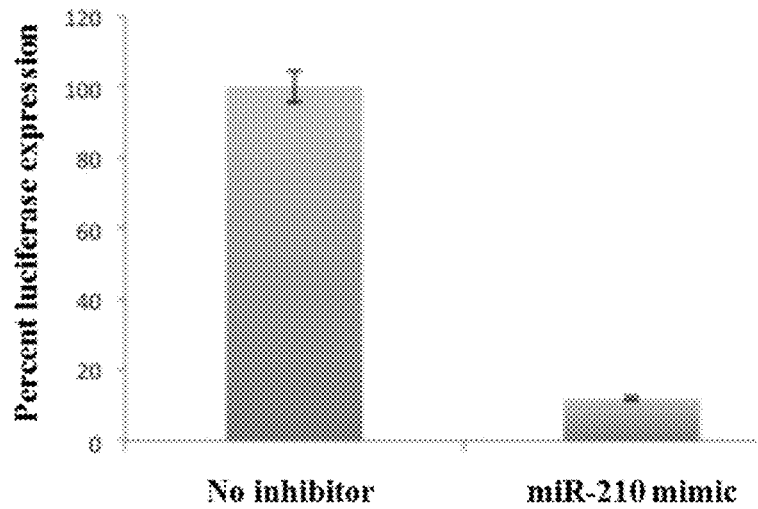
Figure 7E:
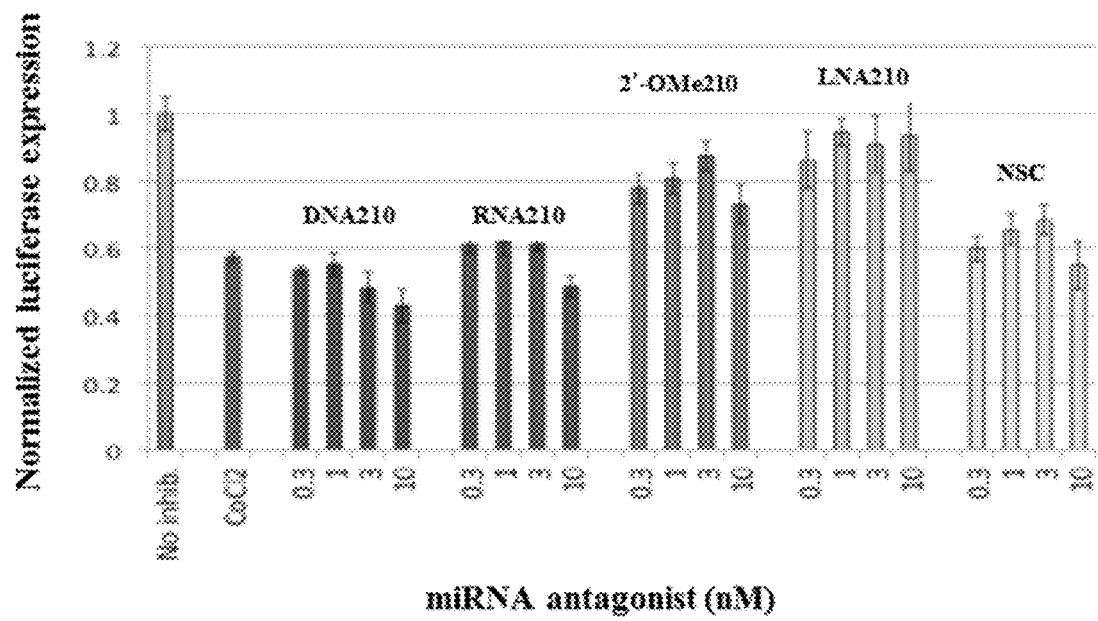
Figure 7F:
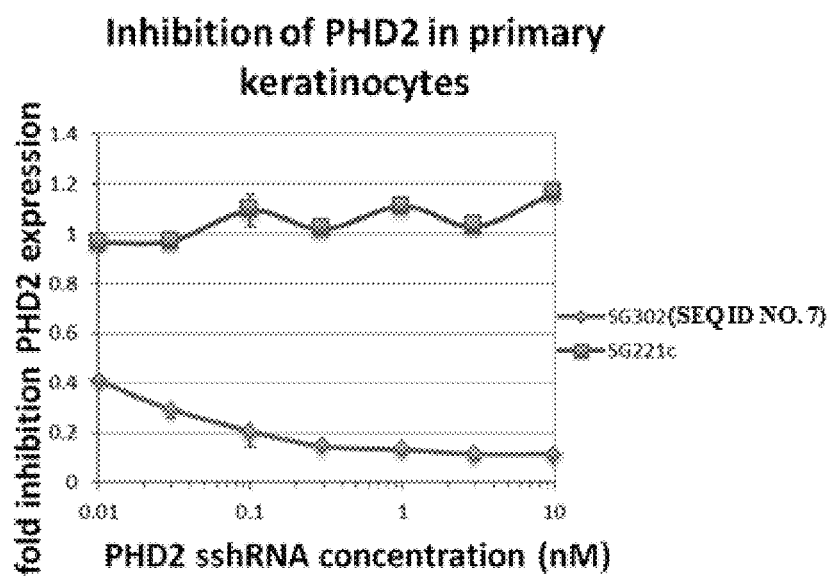
Figure 7G:
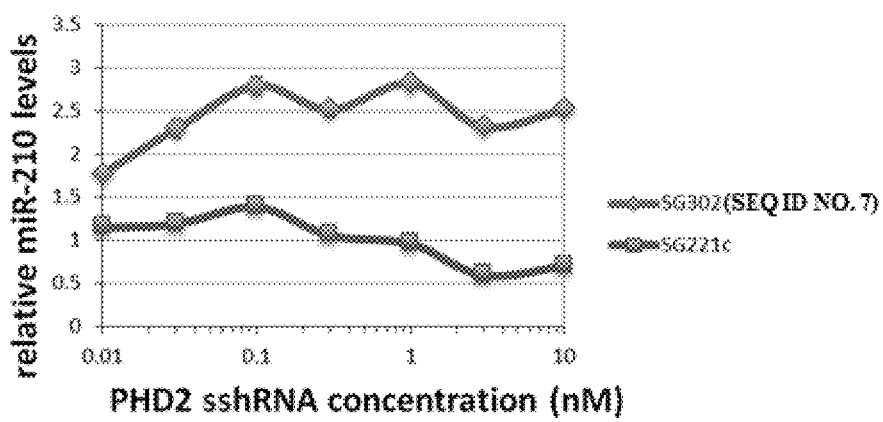
Figure 7H:
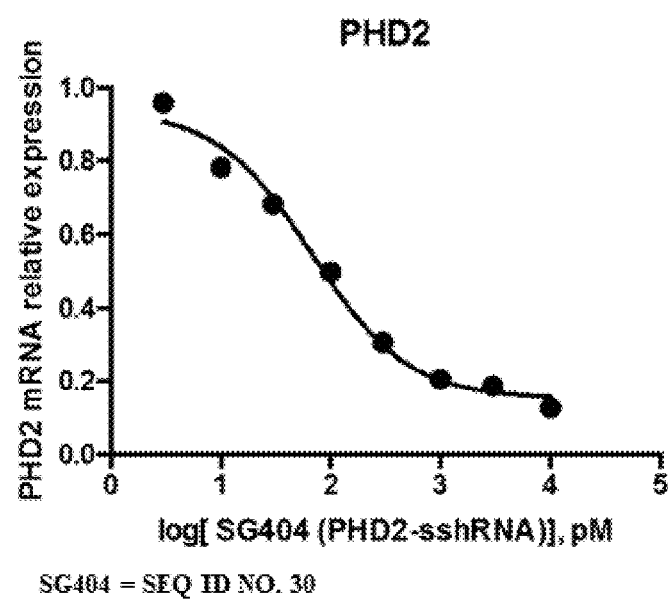
Figure 7I:
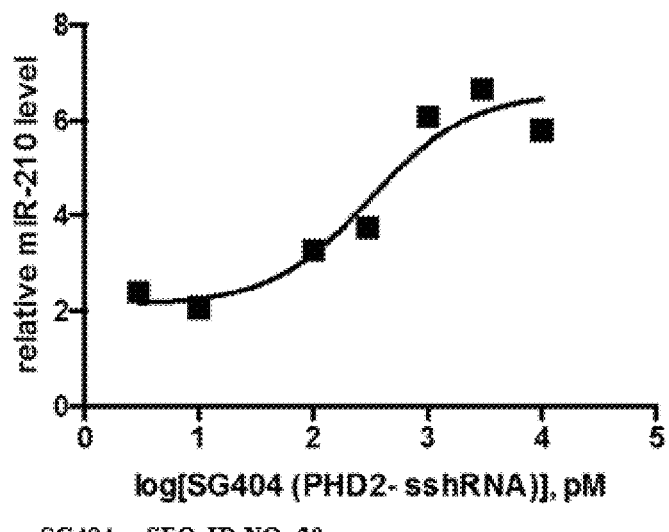
Figure 7J:
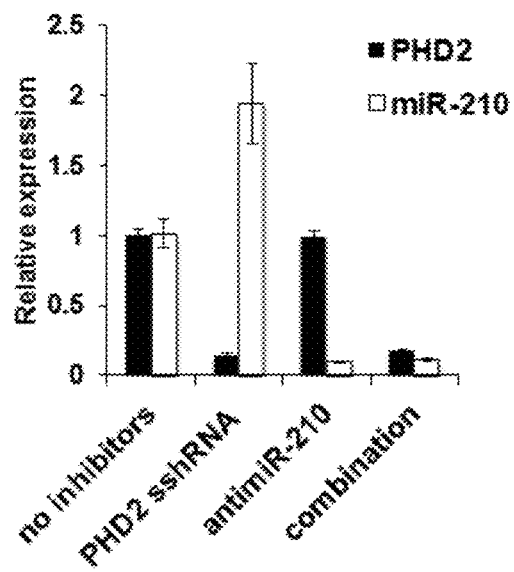

FIG. 7A shows possible modification patterns for a miR-210 miRNA antagonist. FIG. 7B shows qRT-PCR of human PHD2 transcript in human HaCaT keratinocytes transfected with the following: no inhibitor; an sshRNA targeting human PHD2 (SG302, SEQ ID NO. 7); a control sshRNA (ssh-NSC); SG302 (SEQ ID NO. 7) and a LNA-modified miR-210 (SEQ ID NO. 3) miRNA antagonist (SG302+LNA210); SG302 (SEQ ID NO. 7) and a 2'-O-methyl-modified miR-210 miRNA antagonist (SG302+2'-O-methyl 210); ssh-NSC and a LNA-modified control miRNA antagonist (ssh-NSC+LNA-NSC); LNA210; 2'-O-methyl 210; and LNA-NSC. Values are normalized relative to a control transcript (GAPDH) and to untransfected human HaCaT keratinocytes. FIG. 7C shows miRNA qRT-PCR (miR-qRT-PCR) of miR-210 miRNA in human HaCaT keratinocytes transfected with the following: no inhibitor; SG302; ssh-NSC; SG302+LNA210; SG302+2'-O-methyl 210; ssh-NSC+LNA-NSC; LNA210; 2'-O-methyl 210; and LNA-NSC. Values are normalized relative to a control small nucleolar RNA (RNU44) and to untransfected human HaCaT keratinocytes. FIG. 7D shows a luciferase assay with a miR-210 reporter in human HaCaT keratinocytes transfected with no inhibitor or a miR-210 mimic. The miR-210 reporter was generated by sub-cloning four tandem miR-210 binding sites derived from the target found in the 3' untranslated region (3' UTR) of E2F3, each separated by a 8 basepair (bp) sequence, into the 3' UTR of *Renilla* luciferase (r-Luc) of the psiCheck-2 dual luciferase reporter vector (Promega). This vector also contains constitutively expressed firefly luciferase (f-Luc) for transfection normalization. FIG. 7E shows a luciferase assay with a miR-210 reporter in human HaCaT keratinocytes treated with the following: no inhibitor (column 1); $CoCl_2$ (column 2); $CoCl_2$ and increasing concentrations of DNA modified miR-210 miRNA antagonist (DNA210; columns 3-6); $CoCl_2$ and increasing concentrations of miR-210 miRNA antagonist (RNA210; columns 7-10); $CoCl_2$ and increasing concentrations of 2'-O-methyl modified miR-210 miRNA antagonist (2'-O-methyl 210; columns 11-14); $CoCl_2$ and increasing concentrations of LNA modified miR-210 miRNA antagonist (LNA210; columns 15-18); and $CoCl_2$ and increasing concentrations of a control miRNA antagonist (NSC; columns 19-22). Values are normalized as in FIG. 7D. FIG. 7F shows qRT-PCR of human PHD2 transcript in human primary keratinocytes transfected with increasing amounts of an sshRNA targeting human PHD2 (SG302, SEQ ID NO. 7) and a control sshRNA (SG221c). Transcript levels were quantified using the $2^{\Delta\Delta Ct}$ method relative to cells not transfected with inhibitor and normalized to GAPDH transcript. FIG. 7G shows qRT-PCR of miR-210 in human primary keratinocytes transfected with increasing amounts of an sshRNA targeting human PHD2 (SG302, SEQ ID NO. 7) and a control sshRNA (SG221c). miRNA levels were quantified using the $2^{\Delta\Delta Ct}$ method relative to cells not transfected with inhibitor and normalized to RNU44 small nucleolar RNA. FIG. 7H shows qRT-PCR of mouse PHD2 transcript in NIH-3T3 cells transfected with increasing amounts of an sshRNA targeting mouse PHD2 (SG404, SEQ ID NO. 30). Transcript levels were quantified using the $2^{\Delta\Delta Ct}$ method relative to cells not transfected with inhibitor and normalized to GAPDH transcript. FIG. 7I shows qRT-PCR of miR-210 in NIH-3T3 cells transfected with increasing amounts of an sshRNA targeting mouse PHD2 (SG404, SEQ ID NO. 30). miRNA levels were quantified using the $2^{\Delta\Delta Ct}$ method relative to cells not transfected with inhibitor and normalized to sno-234 small nucleolar RNA. FIG. 7J shows relative expression of PHD2 and miR-210 both alone and in combination with PHD2-targeting SG302 sshRNA (SEQ ID NO. 7) and antimiR-210 (SG603, SEQ ID NO. 34) in HaCaT cells.

Example 7. Effect of miRNA Antagonists on Immunostimulatory Pathways

Figure 8A:
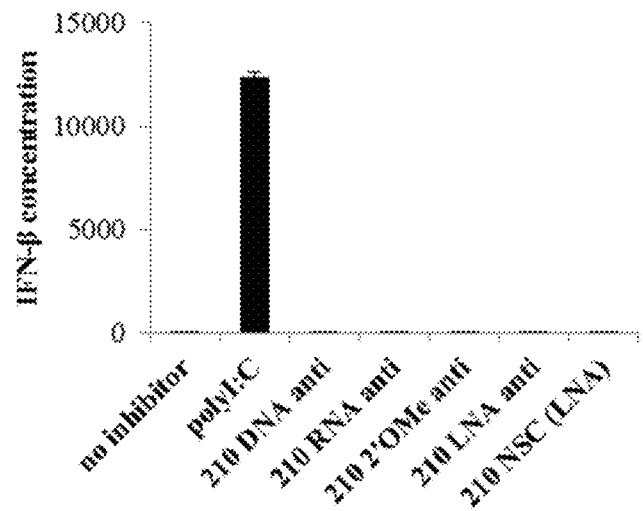
FIG. 8A-FIG. 8C illustrate cytokine levels in response to treatment with a miRNA antagonist.
Figure 8B:
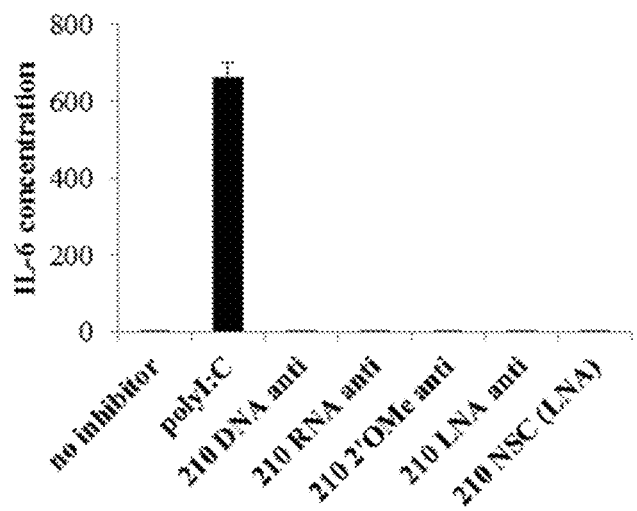
Figure 8C:
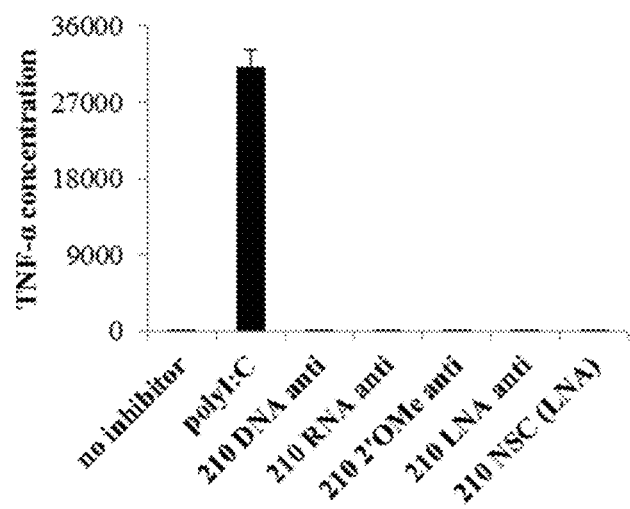

FIG. 8A shows qRT-PCR for IFN-β in MRC-5 lung fibroblasts treated with: no inhibitor; polyI:C; a DNA modified miR-210 miRNA antagonist (210 DNA anti (SG602, SEQ ID NO. 33)); a miR-210 miRNA antagonist (210 RNA anti (SG601, SEQ ID NO. 32)); a 2'-O-methyl modified miR-210 miRNA antagonist (210 2'-O-methyl anti (SG603, SEQ ID NO. 34)); a LNA modified miR-210 miRNA antagonist (210 LNA anti (SG604, SEQ ID NO. 35)); and a LNA modified control miRNA antagonist (210 NSC (LNA) (SG605, SEQ ID NO. 36)). FIG. 8B shows qRT-PCR for IL-6 in cells treated with: no inhibitor; polyI:C; 210 DNA anti; 210 RNA anti; 210 2'-O-methyl anti; 210 LNA anti; and 210 NSC (LNA). FIG. 8C shows qRT-PCR for TNF-α in cells treated with: no inhibitor; polyI:C; 210 DNA anti; 210 RNA anti; 210 2'-O-methyl anti; 210 LNA anti; and 210 NSC (LNA).

Example 8. Effect of fluorescent conjugate moiety on sshRNA activity

Figure 9:
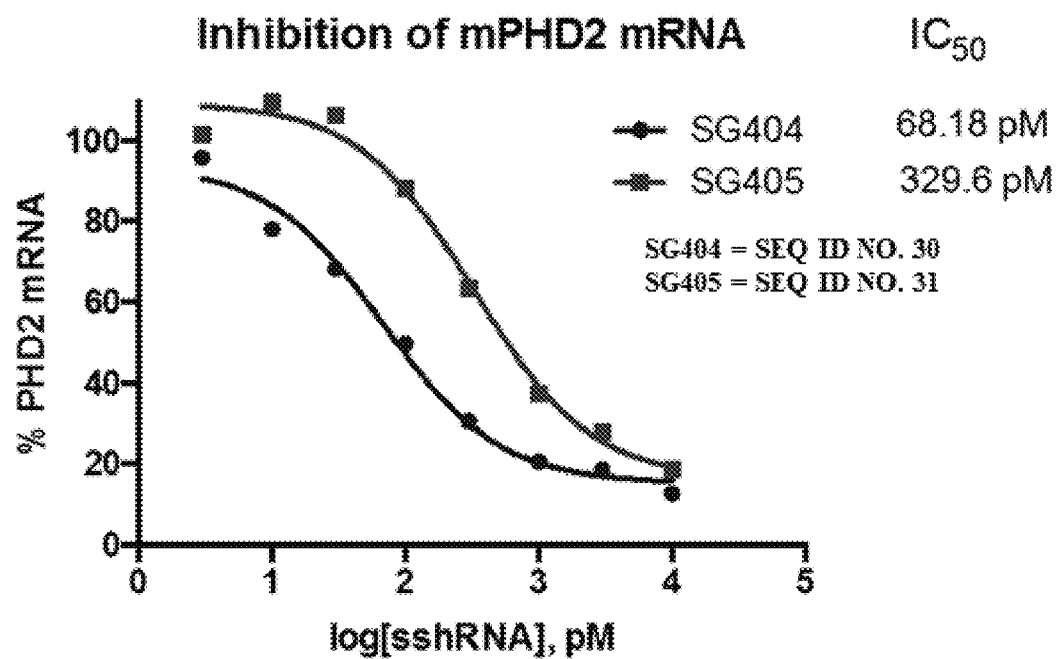
FIG. 9 illustrates expression of PHD2 transcript in response to treatment with an RNAi molecule.

FIG. 9 shows qRT-PCR of mouse PHD2 (mPHD2) transcript in mouse cells transfected with increasing amounts of an unmodified sshRNA targeting PHD2 (SG404, SEQ ID NO. 30) or a PHD2-targeting sshRNA modified to have a $C_6$-amine-TexasRed (AlexaFluor594) conjugated to the first nucleotide of the loop (SG405, SEQ ID NO. 31). Values are normalized relative to a control transcript (GAPDH) and to untransfected mouse cells by the $2^{-\Delta\Delta Ct}$ method.

Example 9. Effect of sshRNAs on diabetic wound healing

The leptin receptor deficient db/db type II diabetes mouse model was used as a model of diabetic wound healing. Males aged 8 to 12 weeks were used for the study. Isoflurane was administered as an anesthetic and full-thickness skin punch biopsies (6-mm in diameter) were created in pairs on the dorsa of db/db mice, equidistant from the midline. The skin and underlying panniculus was removed from the biopsy area. Following the punch biopsy, rubber donuts with a hole about 6 mm in diameter in their center was sutured in place around the wound to splint the wound open, preventing wound contracture and allowing healing to proceed through re-epithelialization The animals were returned to the housing facility after recovering from anesthesia. All procedures were performed using aseptic techniques. Sterile instruments were used, and animals were clipped and prepped with Betadine. The wounds were covered with a dressing to limit infection.

Figure 10A:
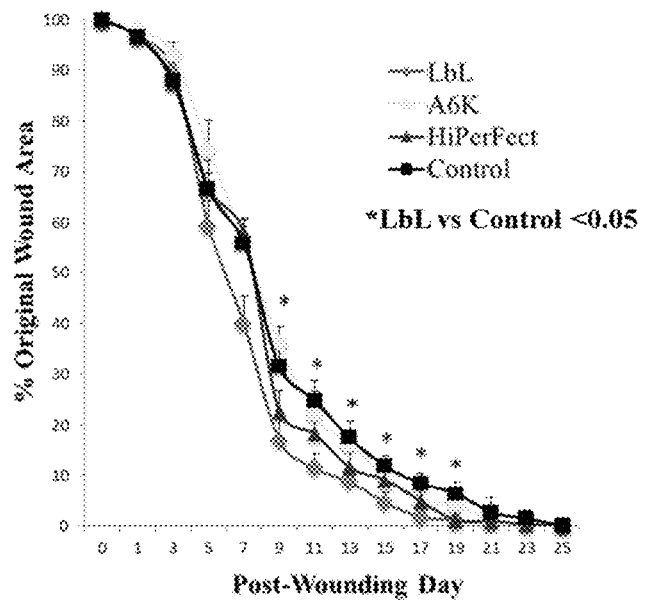
FIG. 10A-FIG. 10F illustrate wound closure over time in response to treatment with an RNAi molecule or a miRNA antagonist.
Figure 10B:
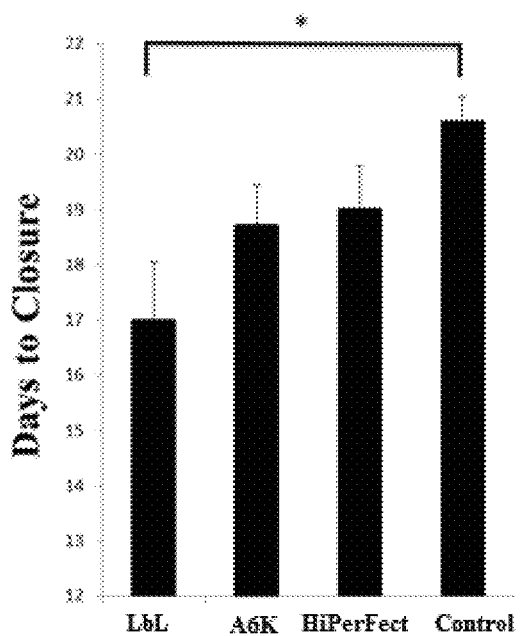

Oligonucleotide formulations were then applied to the animals the following day. Each treatment group had 4 animals with two wounds per animal (number of wounds=8/group). The Layer by Layer group (LbL) received topical treatment with the dressing on which a mesh comprising an sshRNA targeting mouse PHD2 (SG404) was printed. The A6K peptide group (A6K) was injected with 300 picomoles (pmol) of SG404 with the A6K peptide. The HiPerFect group (HiPerFect) was injected with 300 pmol SG404 with the HiPerFect reagent. The control group was injected with PBS as done for the A6K and HiPerFect groups. For the A6K, HiPerFect, and PBS groups, injections were intradermal, with four injections administered locally around the wound. Images of the wound were captured every other day to monitor progress of wound closure. The wound area was calculated digitally, and a time to closure curve was generated. FIG. 10A shows the percentage of original wound area over 25 days in the LbL, A6K, HiPerFect, and Control treatment groups. * over time points on the graph in FIG. 10A indicate p-values <0.05 between the SG404-LbL group (diamond marker) vs the control group (square marker). Treatment with an sshRNA targeting PHD2 (SG404) improves diabetic wound healing. FIG. 10B shows the days until the wound closed in the LbL, A6K, HiPerFect, and Control treatment groups. Average time to wound closure in SG404-LbL group was 17±1.05 days vs control group (20.6±0.45 days). * indicates p-value=0.01 between SG404 LbL group and control group with respect to days to wound closure. PHD2-targeting sshRNAs shows a therapeutically significant increase in rate of wound closure and reduction in time to wound closure in db/db mice.

Figure 10C:
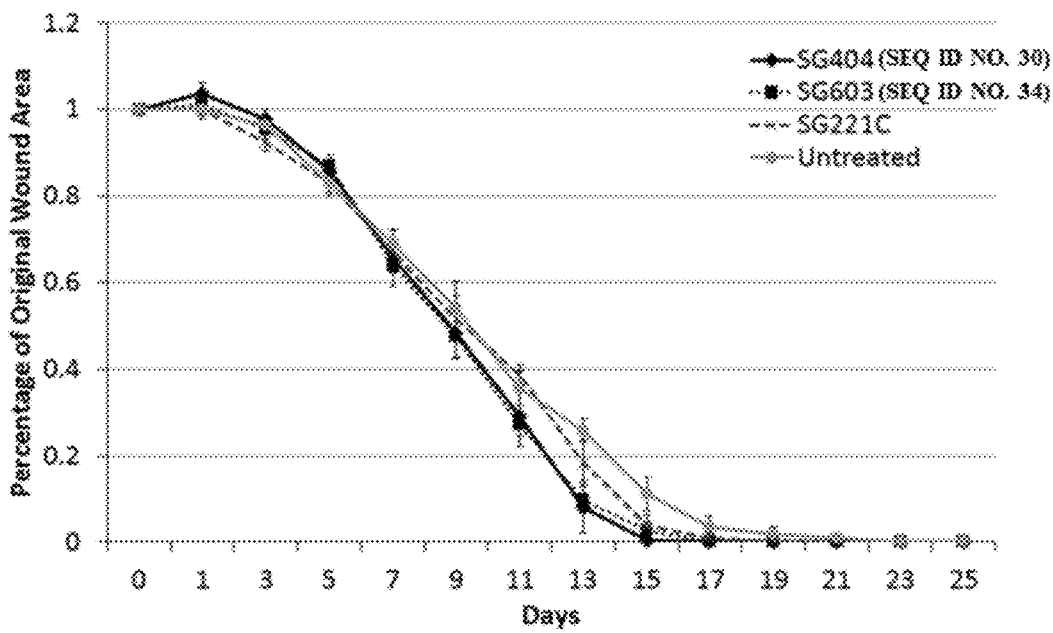
Figure 10D:
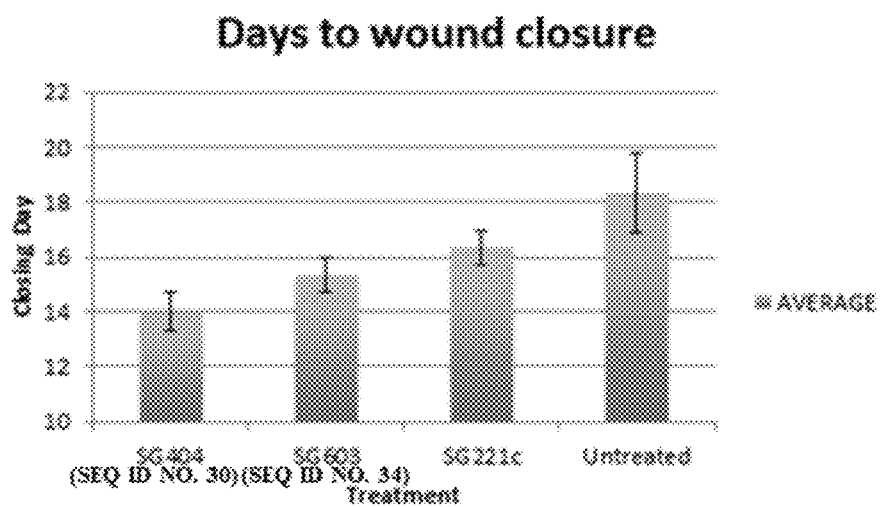

A further study was performed in which db/db mice were wounded as described above. Animals were then untreated or given a LbL topical treatment of a control sshRNA (SG221c), SG404, or a miR-210 antagonist (SG603). FIG. 10C shows the percentage of original wound area over 25 days in the Untreated, SG404, SG603, and SG221c treatment groups. FIG. 10D shows the days until the wound closed in each treatment group. Average days to wound closure ±SEM were as follows: SG404 (14.00±0.68 days), SG603 (15.33±0.61 days), SG221c control (16.33±0.07 days), untreated control (18.33±1.42 days). P-values for SG404 vs untreated and SG404 vs SG221c control sshRNAs were 0.021 and 0.034, respectively. P-value for SG603 vs untreated control was 0.08.

Figure 10E:
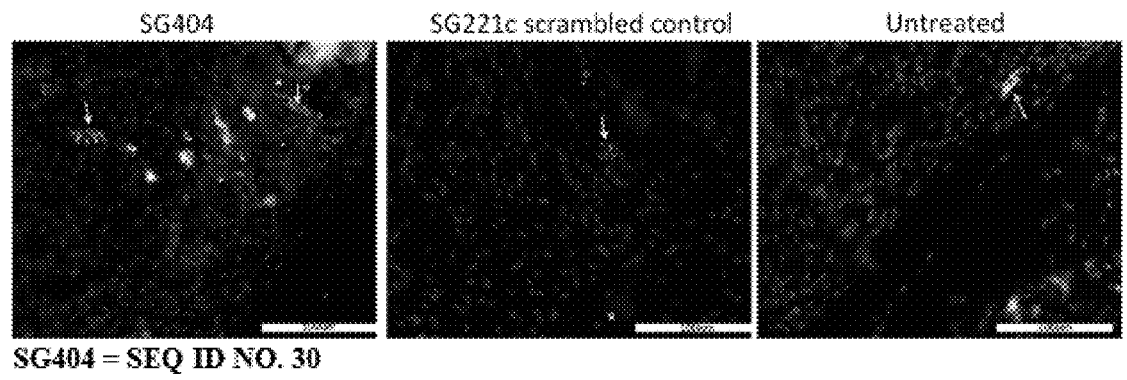
Figure 10F:
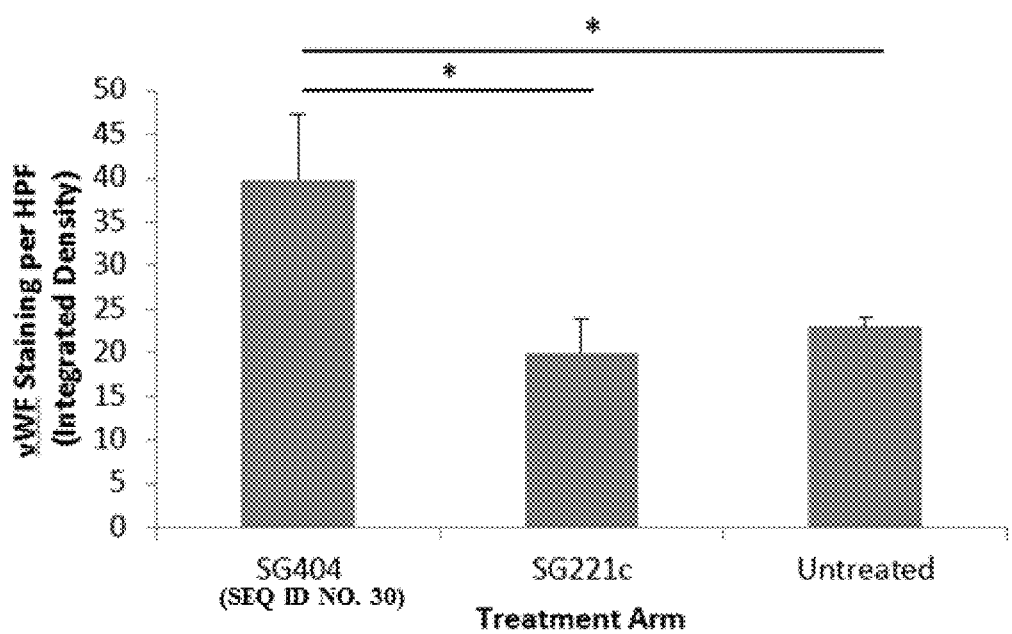

In a further study in which db/db mice were wounded as described above, histological analysis was performed to examine the effect of sshRNA treatment on neovascularization in the wound area. Animals were untreated or given a LbL topical treatment of control sshRNAs (SG221c) or SG404 sshRNA for a total of 6 wounds per treatment group. Animals were sacrificed at day 7 after wounding, and histology slides were prepared and stained with an antibody to von Willebrand Factor (vWF) (EMD Millipore). 3 images were captured per slide. A blinded analysis was performed with fluorescence intensity measured by Image J software. FIG. 10E shows representative images of fluorescence staining at day 7 for each treatment group. In FIG. 10F, computed values (integrated density) of vWF staining for each treatment group are plotted. Staining for vWF showed a significant increase in neovascularization in the wound area at Day 7 post wounding for SG404-treated wounds. * on the graph between treatment arms represent p-values <0.05.

Example 10. Development of sshRNAs Targeting Both Mouse PHD2 and Human PHD2

Figure 11A:
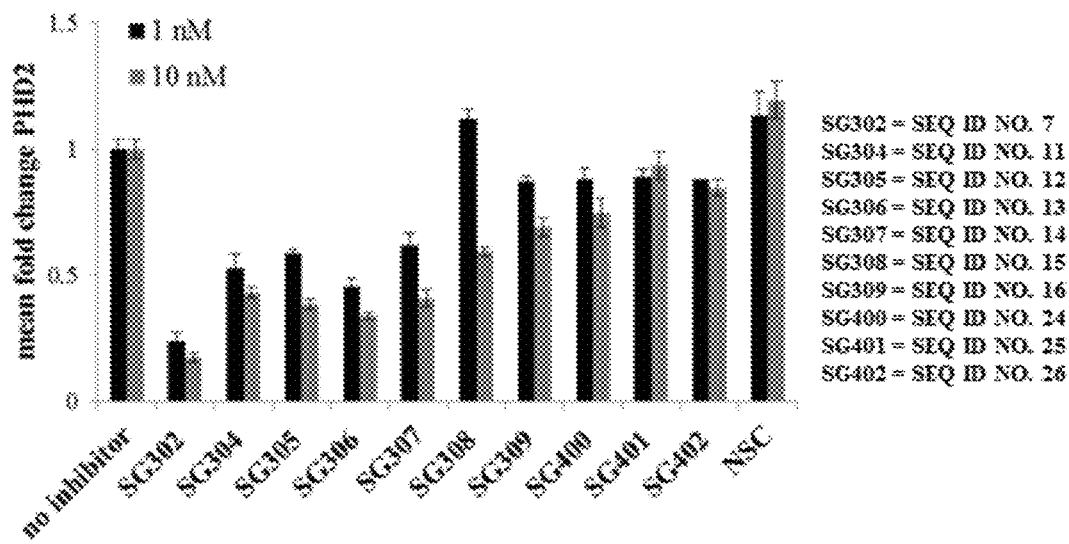
FIG. 11A-FIG. 11D illustrate expression of PHD2 transcript in response to treatment with an RNAi molecule.
Figure 11B:
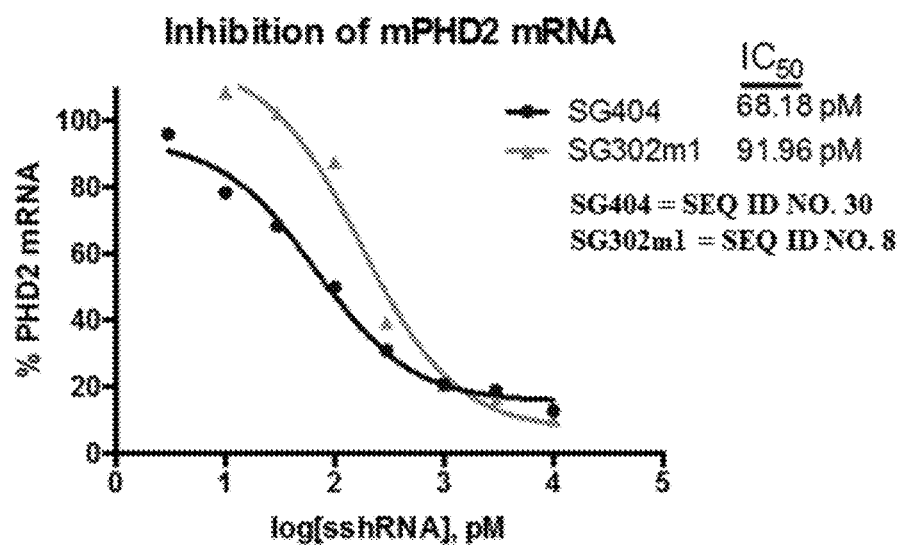
Figure 11C:
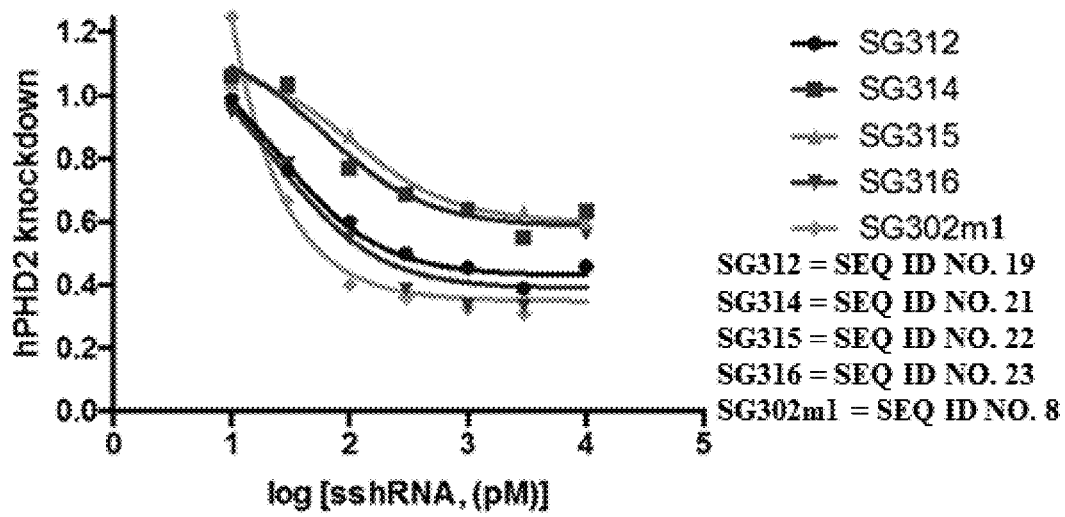

FIG. 11A shows qRT-PCR of human PHD2 transcript in human kidney 293FT cells transfected with either 1 nM or 10 nM of the following: no inhibitor; sshRNAs designed to target human PHD2 (SG302 (SEQ ID NO. 7), SG304-SG309 (SEQ ID NO. 11-SEQ ID NO. 16)); and sshRNAs designed to target mouse PHD2 (SG400-SG402, SEQ ID NO. 24-SEQ ID NO. 26); and a control sshRNA (NSC). Values are normalized relative to a control transcript (GAPDH) and to untransfected human HaCaT keratinocytes by the $2^{-\Delta\Delta Ct}$ method. FIG. 11B shows qRT-PCR of mouse PHD2 (mPHD2) transcript in mouse NIH3T3 fibroblasts transfected with increasing amounts of sshRNAs designed to target mouse PHD2 (SG404, SEQ ID NO. 30) or a modified sshRNA designed to target human PHD2 (SG302m1, SEQ ID NO. 8). Values are normalized relative to a control transcript (GAPDH) and to untransfected mouse NIH3T3 fibroblasts by the $2^{-\Delta\Delta Ct}$ method. FIG. 11C shows qRT-PCR of human PHD2 (hPHD2) transcript in human HaCaT keratinocytes transfected with increasing amounts of sshRNAs designed to target either human PHD2 or mouse PHD2

Figure 11D:
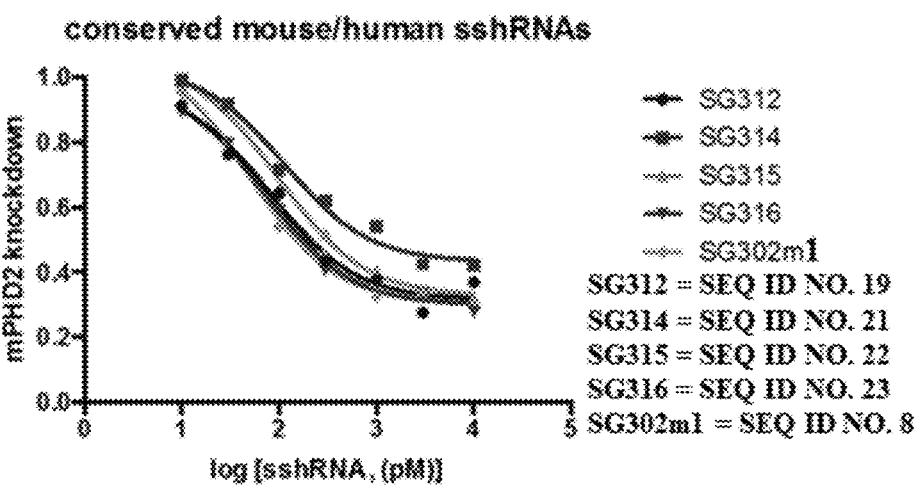

(SG312 (SEQ ID NO. 19), and SG314-SG316 (SEQ ID NO. 21-SEQ ID NO. 23)) or a modified sshRNA designed to target human PHD2 (SG302m1, SEQ ID NO. 8). Values are normalized relative to a control transcript (GAPDH) and to untransfected human HaCaT keratinocytes by the $2^{-\Delta\Delta Ct}$ method. FIG. 11D shows qRT-PCR of mouse Phd2 (mPHD2) transcript in mouse NIH3T3 fibroblasts transfected with increasing amounts of sshRNAs designed to target either human PHD2 or mouse Phd2 (SG312 (SEQ ID NO. 19), and SG314-SG316 (SEQ ID NO. 21-SEQ ID NO. 23)) or a modified sshRNA designed to target human PHD2 (SG302m1, SEQ ID NO. 8). Values are normalized relative to a control transcript (Gapdh) and to untransfected NIH3T3 fibroblasts.

Example 11. Effect of sshRNAs and miRNA Antagonists on Scratch Wound Closure

Figure 12A:
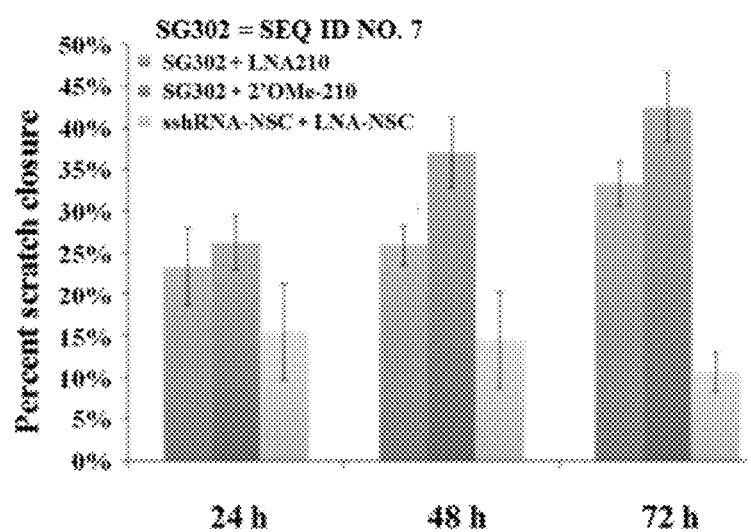
FIG. 12A-FIG. 12B illustrate cell scratch closure over time in response to treatment with an RNAi molecule and a miRNA antagonist.
Figure 12B:
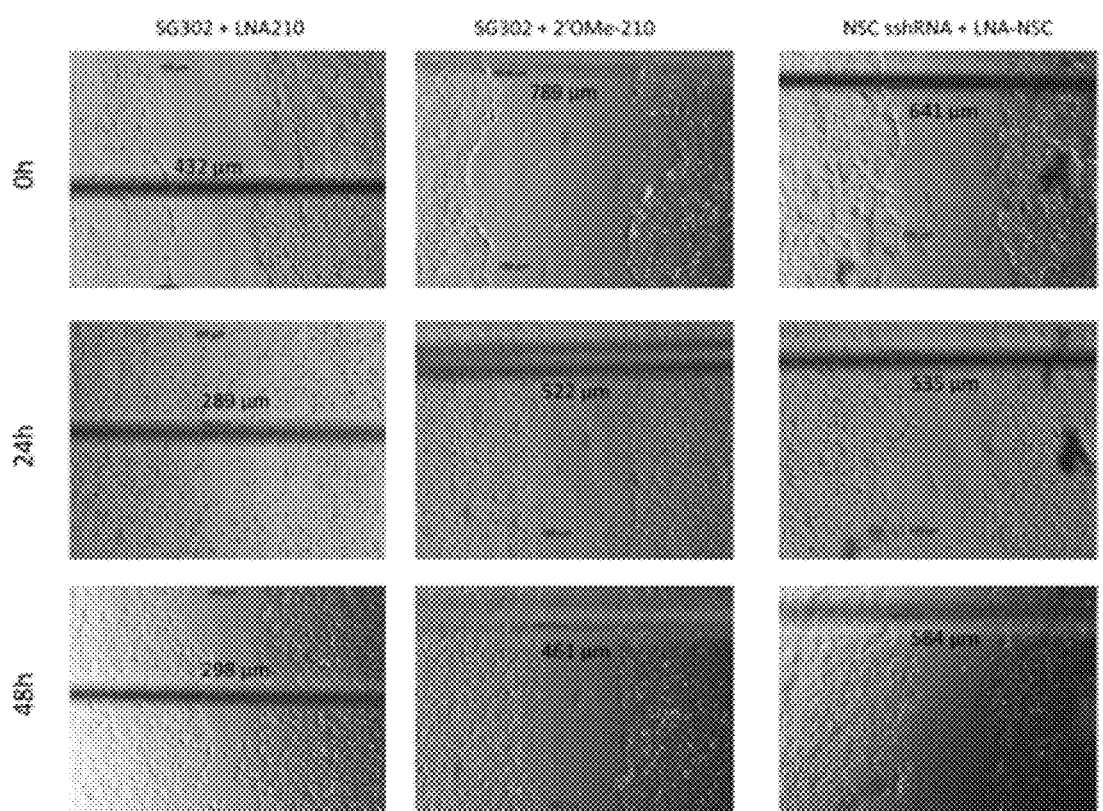

To measure cell migration, human HaCaT keratinocytes were plated at about 60% to about 70% confluence in 12-well plates and were transfected with sshRNAs and microRNA antagonists. When cells reached ~100% confluence, the medium was replaced with Dulbecco's Modified Eagle Medium containing 0.5% fetal bovine serum two hours before scratching with a 200 µL pipet tip. Photographs and measurements across the cell-free scratch were taken immediately after scratching and at the indicated time points at six marked places per transfection condition. The percent closure at each time point was calculated relative to the initial scratching width. FIG. 12A shows the percent scratch closure at 24 hours (24 h), 48 h, and 72 h of human HaCaT keratinocytes transfected with the following: an sshRNA targeting human PHD2 (SG302, SEQ ID NO. 7) and a LNA-modified miR-210 miRNA antagonist (SG302 (SEQ ID NO. 7)+LNA210); SG302 (SEQ ID NO. 7) and a 2'-O-methyl-modified miR-210 miRNA antagonist (SG302+2'-O-methyl 210); and a control sshRNA (ssh-NSC) and a LNA-modified control miRNA antagonist (ssh-NSC+LNA-NSC). FIG. 12B provides representative images of the scratch wounds at 0 hours (0 h), 24 h, and 48 h of human HaCaT keratinocytes transfected with SG302+LNA210, SG302+2'-O-methyl 210, and ssh-NSC+LNA-NSC. In bold is the scratch wound distance in microns (µm). The scale bar for all images is 100 µm.

Similar scratch wound studies were performed with normal human epidermal keratinocytes (NHEK) as described above. The results are shown in TABLE 2.

TABLE 2

| Inhibitors | Percent wound closure (10 h) |
| --- | --- |
| SG302 (SEQ ID NO. 7) + LNA210 | 33 ± 6% |
| SG302 (SEQ ID NO. 7) + 2'-O-methyl 210 | 41 ± 8% |
| NSC sshRNA + NSC 210 | 20 ± 5% |

Example 12. Designs and Efficacy of Pre-miRNA Mimics

FIG. 13A-E show designs for pre-miRNA mimics of miR-21. Mature miR-21 (SEQ ID NO. 4) is the sequence within the black boxes. Lines between nucleotides correspond to base-pairing interactions. Dots between nucleotides correspond to spaces opposite a bulged nucleotide. Modified nucleotides are underlined. FIG. 13F shows a luciferase assay with a miR-21 reporter in human 293FT cells transfected with no mimic or a miR-21 mimic. The miR-21 reporter was generated by sub-cloning four tandem miR-21 complementary binding sites, each separated by a 8 basepair (bp) sequence, into the 3' UTR of *Renilla* luciferase (r-Luc) of the psiCheck-2 dual luciferase reporter vector (Promega). This vector also contains constitutively expressed firefly luciferase (f-Luc) for transfection normalization. FIG. 13F shows a luciferase assay with a miR-21 reporter in human 293FT cells treated with increasing concentrations of the following: SG701, SEQ ID NO. 44 (FIG. 13A), SG702, SEQ ID NO. 45 (FIG. 13B), SG703, SEQ ID NO. 46 (FIG. 13C), SG703, SEQ ID NO. 46 (replicate 2) (FIG. 13C), SG704, SEQ ID NO. 47 (FIG. 13D), miRIDIAN miR-21 mimic (Dharmacon, positive control) and cel-67 mimic (Dharmacon, miRIDIAN miRNA mimic negative control #1). Values are computed relative to cells that were not transfected with a mimic as in FIG. 7D.

Example 13. Effect of Pre-miRNA Mimic Design

Figure 13A:
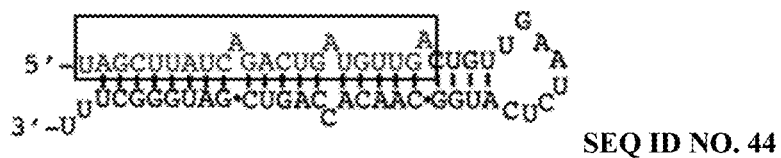
FIG. 13A-FIG. 13F illustrate designs for a pre-miRNA mimic.
Figure 13B:
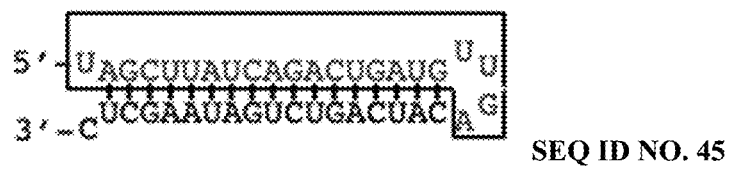
Figure 13C:
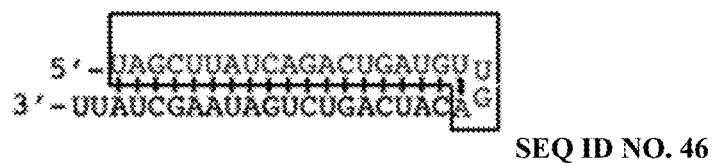
Figure 13D:
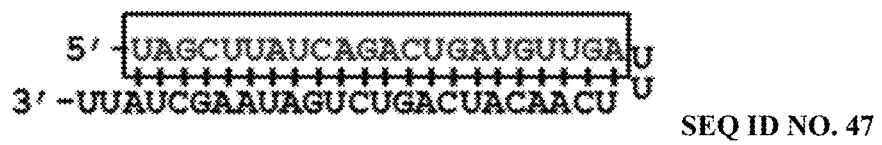
Figure 13E:
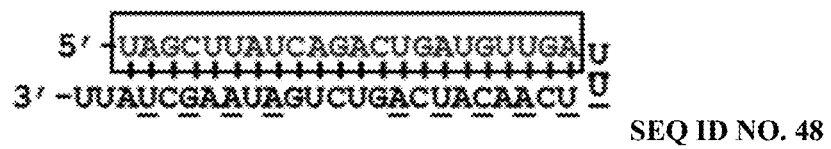
Figure 13F:
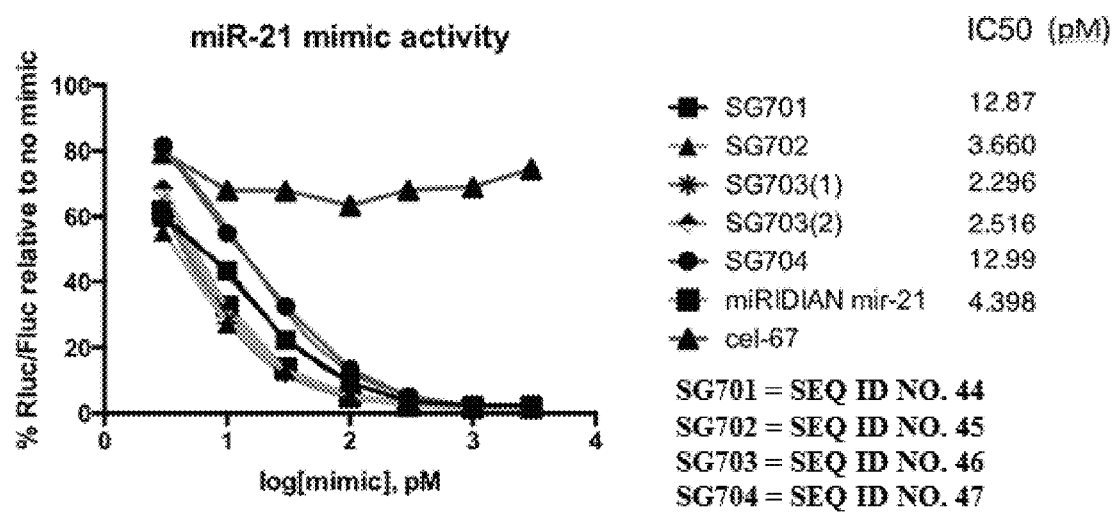
Figure 14A:
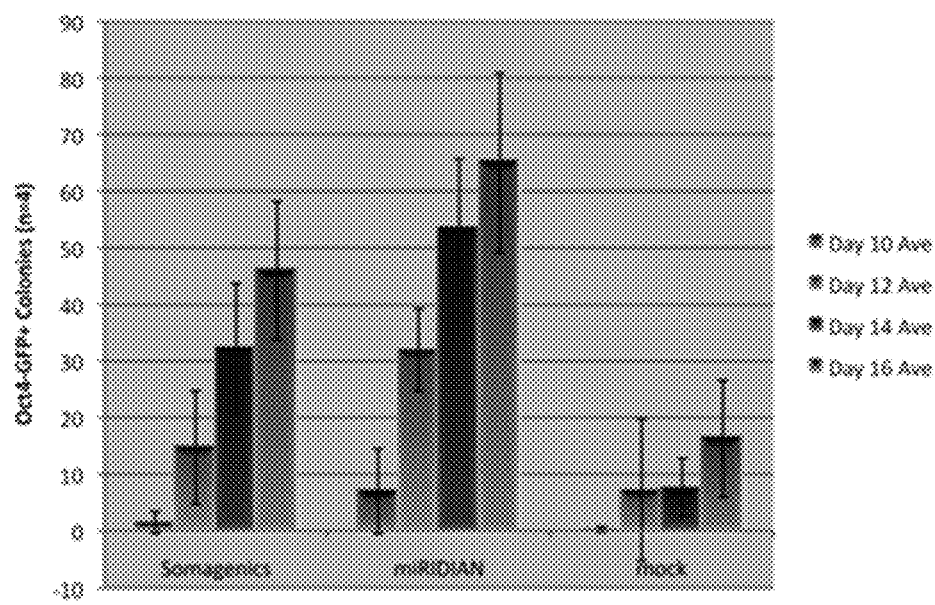
FIG. 14A-FIG. 14B illustrate GFP positive cell number in cells treated with a pre-miRNA mimic.
Figure 14B:
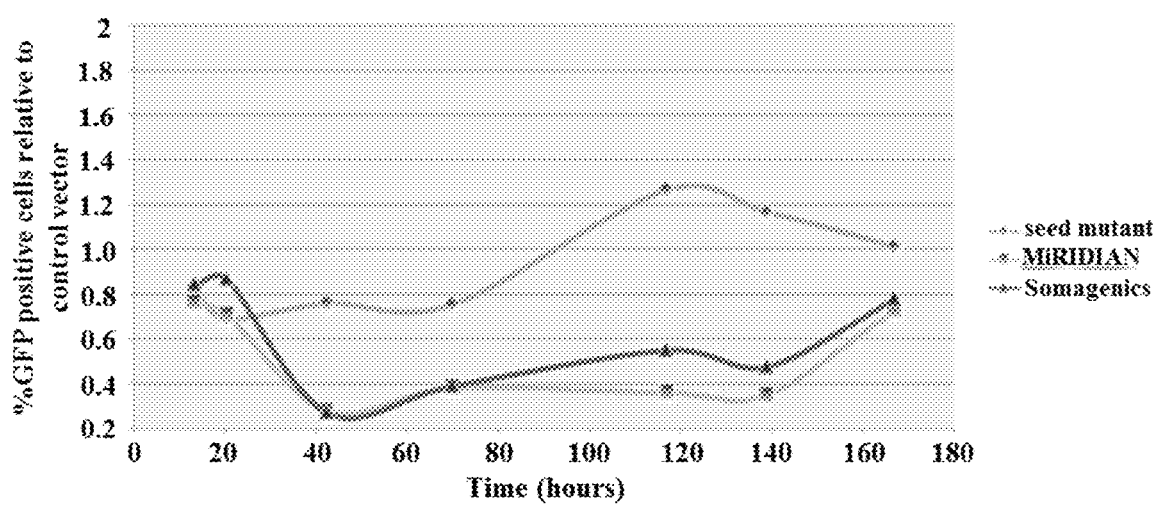

Mouse embryonic fibroblasts (MEFs) that express green fluorescent protein under the control of the Oct4 promoter (Oct4-GFP) were mock transfected, transfected with a standard miR-302b miRNA (miRIDIAN), with a miR-302b seed mutant, or a sshRNA-pre-miR-302b (Somagenics) comparable to the pre-miR-21 design in FIG. 13E. Two days later, these cells were transduced with a cocktail of retroviral vectors expressing Oct4, Klf4 and Sox2. FIG. 14A shows the average (Ave) number of Oct4-GFP-positive colonies in the mock, miRIDIAN, and Somagenics groups at 10, 12, 14, and 16 days after transfection. FIG. 14B shows a percentage of GFP-positive cells relative to cells transfected with a control vector over a time course in the seed mutant, MiRIDIAN, and Somagenics treatment groups.

Example 14. Combination Effect of a sshRNA, miRNA Antagonist, and miRNA Mimic in Diabetic Wound Healing Skin wounding of leptin receptor the deficient db/db type II diabetes mouse model is performed as described in Example 9.

Oligonucleotide formulations are then applied to the animals the following day. All formulations are given topically as an LbL mesh on a dressing on which the oligonucleotides are printed. In group 1, the oligonucleotide is SG404 (SEQ ID NO. 30). In group 2, the oligonucleotide is SG603 (SEQ ID NO. 34). In group 3, the oligonucleotide is a chemically-modified miR-21 pre-miRNA mimic presented in FIG. 13C (pre-miR-21). In group 4, the oligonucleotides are SG404 (SEQ ID NO. 30) and SG603 (SEQ ID NO. 34). In group 5, the oligonucleotides are SG404 (SEQ ID NO. 30) and pre-miR-21. In group 6, the oligonucleotides are SG603 (SEQ ID NO. 34) and pre-miR-21. In group 7, the oligonucleotides are SG404 (SEQ ID NO. 30), SG603 (SEQ ID NO. 34), and pre-miR-21. In group 8, the oligonucleotides are the sshRNA control SG221c, the miRNA antagonist control NSC, and a control scrambled version of pre-miR-21 (pre-miR-21-sc). Images of the wound are captured, the wound area is calculated, and the time to closure curve is generated as in Example 9. Comparisons are made between: each of groups 1-7 and group 8; group 4 and groups 1 and 2; group 5 and groups 1 and 3; group 6 and groups 2 and 3; and group 7 and groups 4, 5, and 6.

Example 15. Therapeutic Administration of Oligonucleotides to a Subject with Chronic Diabetic Wounds A subject in need thereof diagnosed with diabetes mellitus experiences chronic, non-healing, diabetic foot wounds. To treat these wounds, a dressing is applied to a foot wound of the subject. On the dressing is an LbL mesh on which is printed as layers an sshRNA targeting human PHD2, an LNA, 2'-O-methyl-modified miR-210 miRNA antagonist, and a 2'-O-methyl-modified pre-miR-21 pre-miRNA mimic. After cleaning the wound, the dressing is applied such that the mesh is in close physical contact with the wound. The dressing is maintained and, if necessary, exchanged for a fresh dressing with the LbL mesh containing the oligonucleotides. Treatment with the dressing is complete upon complete wound closure.

Example 16. Therapeutic Administration of a Polynucleotide Vector of a sshRNA to a Subject with Chronic Diabetic Wounds A subject in need thereof diagnosed with diabetes mellitus experiences chronic, non-healing, diabetic foot wounds. To treat these wounds, a dressing is applied to a foot wound of the subject. On the dressing is an LbL mesh on which is printed as layers a recombinant adeno-associated virus (rAAV) of a sshRNA targeting human PHD2 expressed from a EF1α promoter. The rAAV is of the AAV1 serotype and is generated to $10^{11}$ pfu. In producing the virus, the adenoviral genes that provide helper functions to AAV are supplied in trans to allow for production of the rAAV particles, so that the rAAV is generated through a three-plasmid system to decrease the probability of production of wild-type AAV. After cleaning the wound, the dressing is applied such that the mesh is in close physical contact with the wound. The dressing is maintained and, if necessary, exchanged for a fresh dressing with the LbL mesh containing the virus. Treatment with the dressing is complete upon complete wound closure.

Example 17. Uptake of LBL-PHD2 sshRNA in Db/Db Mice Measured by Fluorescence

Figure 15:
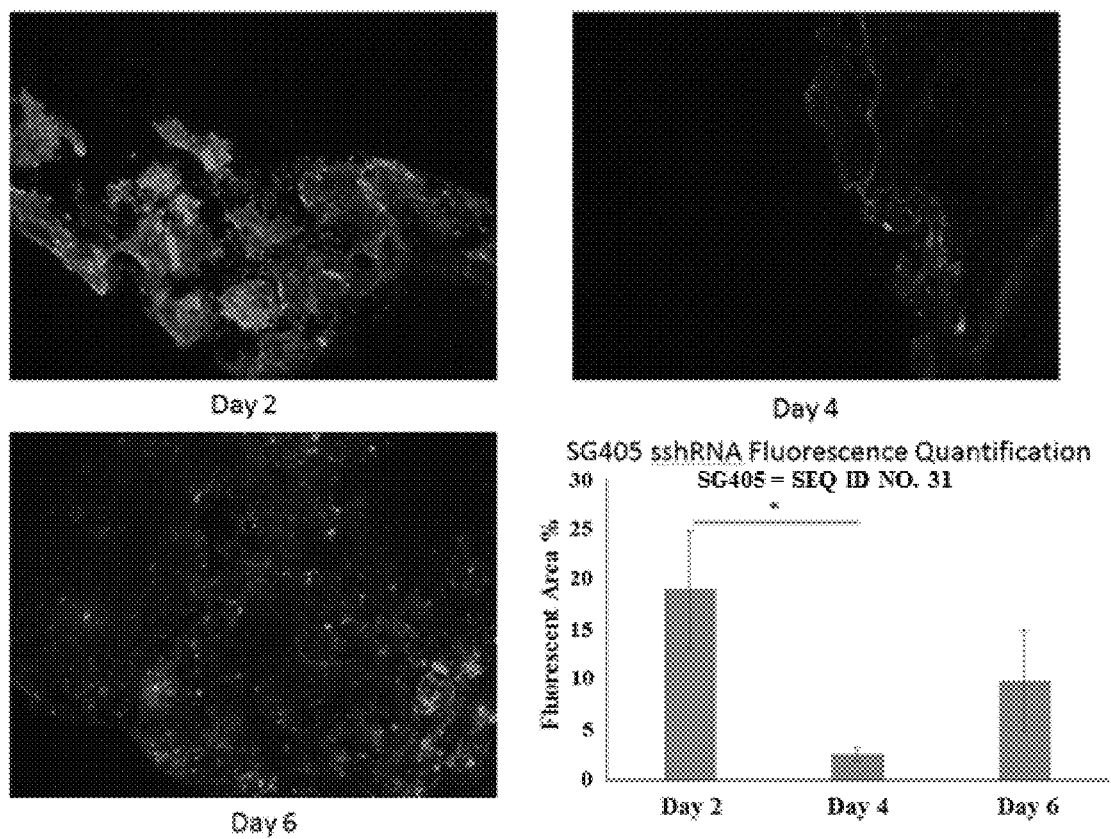
FIG. 15 illustrates uptake of LBL-PHD2 over time in response to treatment with an RNAi molecule.

Skin wounding of leptin receptor the deficient db/db type II diabetes mouse model was performed as described in Example 9. Oligonucleotide formulations LbL-SG405 (SEQ ID NO. 31) containing a Alexa Fluor 594 label was then applied to the animals the following day. Wounds were harvested at day 2, day 4, and day 6. Cryopreserved sections were prepared and imaged by fluorescence microscopy. FIG. 15 shows representative images at each of the time points showing that LbL-SG405 (SEQ ID NO. 31) has been taken up into cells in the wound area. 6 representative images of each time point were obtained and the area of fluorescence was quantified using Image J software. Results are plotted in FIG. 15. Uptake of SG405 (SEQ ID NO. 31) was observed at all time points.

What is claimed is:

1. A pharmaceutical composition comprising:
   a short small hairpin RNA (sshRNA) for inhibiting prolyl hydroxylase domain-containing protein 2 (PHD2) comprising:
   (a) an antisense sequence that is capable of hybridizing to an RNA transcript encoding prolyl hydroxylase domain-containing protein 2; and
   (b) a sense sequence, wherein the sense and antisense sequences form a stem having a length of less than or equal to 19 base pairs; and
   a microRNA (miRNA) antagonist comprising an antisense strand capable of hybridizing to and inhibiting miR-210.

2. The pharmaceutical composition of claim 1, wherein the RNA transcript is encoded by an Egl nine homolog 1 (EGLN1) gene, wherein the EGLN1 gene, minus introns, is represented by a sequence selected from SEQ ID NO. 1 and SEQ ID NO. 2.

3. The pharmaceutical composition of claim 1, wherein the sshRNA comprises a loop region connecting the antisense sequence and the sense sequence selected from a direct connection, 1 nucleotide and 2 nucleotides in length.

4. The pharmaceutical composition of claim 1, wherein the sshRNA consists of the antisense sequence, the sense sequence, a loop region, an optional overhang sequence, and an optional conjugate moiety.

5. The pharmaceutical composition of claim 4, wherein the loop region has a length of zero nucleotides, 1 nucleotide or 2 nucleotides.

6. The pharmaceutical composition of claim 5, wherein the loop region consists of 1 nucleotide or 2 nucleotides.

7. The pharmaceutical composition of claim 1, wherein the sshRNA consists of the antisense sequence, the sense sequence, an optional overhang sequence, and an optional conjugate moiety, wherein the sense sequence and the antisense sequence are directly connected.

8. The pharmaceutical composition of claim 1, wherein the antisense sequence is from about 80% complementary to 100% complementary to the PHD2 transcript.

9. The pharmaceutical composition of claim 1, wherein the sense sequence is from about 10 nucleotides to about 19 nucleotides in length.

10. The pharmaceutical composition of claim 1, wherein the sense sequence is from about 11 nucleotides to about 19 nucleotides in length.

11. The pharmaceutical composition of claim 1, wherein at least one nucleotide comprises a chemical modification.

12. The pharmaceutical composition of claim 11, wherein the chemical modification increases the stability of the shRNA in a biological fluid at least about 20%.

13. The pharmaceutical composition of claim 1, wherein the sshRNA is represented by a sequence selected from SEQ ID NOS: 11-18, 20-22, 25, 31 or 49-325.

14. The pharmaceutical composition of claim 1 comprising a pharmaceutically-acceptable substrate, carrier or salt.

15. The pharmaceutical composition of claim 14, wherein the pharmaceutically-acceptable substrate is a mesh or a dressing.

16. The pharmaceutical composition of claim 15, wherein the mesh is a layered mesh.

17. A method for treating a wound in a subject in need thereof comprising administering a therapeutically effective amount of the pharmaceutical composition of claim 14.

18. The pharmaceutical composition of claim 1, further comprising a pre-miRNA mimic for increasing a steady state level of a mature miR-21 comprising:
   i) a sense sequence;
   ii) an antisense sequence; and
   iii) a loop region, wherein the length of the loop region is the length of 2 nucleotides or less.

19. The pharmaceutical composition of claim 1, wherein at least one ribonucleotide of the sshRNA comprises a chemical modification.

20. The pharmaceutical composition of claim 1, wherein the miRNA antagonist is represented by a sequence selected from SEQ ID NOS: 32-43 or 326-328.

* * * * *